United States Patent
Zdeblick et al.

(10) Patent No.: US 11,476,952 B2
(45) Date of Patent: Oct. 18, 2022

(54) PHARMA-INFORMATICS SYSTEM

(71) Applicant: OTSUKA PHARMACEUTICAL CO., LTD., Tokyo (JP)

(72) Inventors: Mark Zdeblick, Portola Valley, CA (US); Andrew Thompson, Portola Valley, CA (US); Aleksandr Pikelny, Los Angeles, CA (US); Timothy L. Robertson, Belmont, CA (US); Hooman Hafezi, Redwood City, CA (US)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 17/062,897

(22) Filed: Oct. 5, 2020

(65) Prior Publication Data

US 2021/0273734 A1    Sep. 2, 2021

Related U.S. Application Data

(63) Continuation of application No. 16/793,374, filed on Feb. 18, 2020, now abandoned, which is a
(Continued)

(51) Int. Cl.
*H04B 13/00* (2006.01)
*A61B 5/00* (2006.01)
(Continued)

(52) U.S. Cl.
CPC ......... *H04B 13/005* (2013.01); *A61B 5/0028* (2013.01); *A61B 5/0031* (2013.01);
(Continued)

(58) Field of Classification Search
CPC ....... A61B 5/0028; A61B 5/0031; A61B 5/07; A61B 5/073; A61B 5/076; A61B 5/1473;
(Continued)

(56) References Cited

U.S. PATENT DOCUMENTS 1,548,459 A    8/1925  Hammer
2,587,158 A    2/1952  Hofberg
(Continued)

FOREIGN PATENT DOCUMENTS

CN    1588649    3/2005
CN    1650844    8/2005
(Continued)

OTHER PUBLICATIONS

AADE, "AADE 37th Annual Meeting San Antonio Aug. 4-7, 2010" American Association of Diabetes Educators (2010); http://www.diabeteseducator.org/annualmeeting/2010/index.html; 2 pp.
(Continued)

*Primary Examiner* — Brian A Zimmerman
(74) *Attorney, Agent, or Firm* — Pillsbury Winthrop Shaw Pittman, LLP

(57) ABSTRACT

An apparatus that includes a partial power source including a first material and a second material, the partial power source configured to generate, upon contact with a conducting medium, a potential difference between the first material and the second material to provide power to a control device, and generate, using the first material and the second material, a current flow within the conducting medium, the current flow including information encoded based on a variable conductance between the first material and the second material.

14 Claims, 28 Drawing Sheets

Related U.S. Application Data continuation of application No. 15/788,698, filed on Oct. 20, 2017, now Pat. No. 10,610,128, which is a continuation of application No. 14/699,681, filed on Apr. 29, 2015, now abandoned, which is a continuation of application No. 14/596,056, filed on Jan. 13, 2015, now Pat. No. 9,681,842, which is a continuation of application No. 12/949,720, filed on Nov. 18, 2010, now Pat. No. 9,119,554, which is a continuation of application No. 11/912,475, filed as application No. PCT/US2006/016370 on Apr. 28, 2006, now Pat. No. 8,847,766.

(60) Provisional application No. 60/790,335, filed on Apr. 7, 2006, provisional application No. 60/713,680, filed on Sep. 1, 2005, provisional application No. 60/694,078, filed on Jun. 24, 2005, provisional application No. 60/676,145, filed on Apr. 28, 2005.

(51) Int. Cl.
　　*H01Q 1/27*　　　(2006.01)
　　*G16H 20/10*　　(2018.01)
　　*H04W 4/80*　　 (2018.01)
　　*A61B 5/07*　　　(2006.01)
　　*A61J 3/00*　　　 (2006.01)
　　*G06K 7/10*　　　(2006.01)
　　*A61B 5/1473*　　(2006.01)

(52) U.S. Cl.
CPC ............... *A61B 5/07* (2013.01); *A61B 5/073* (2013.01); *A61B 5/076* (2013.01); *A61B 5/1473* (2013.01); *A61B 5/4833* (2013.01); *A61B 5/4839* (2013.01); *A61B 5/6861* (2013.01); *A61B 5/7282* (2013.01); *A61J 3/007* (2013.01); *G06K 7/10168* (2013.01); *G16H 20/10* (2018.01); *H01Q 1/273* (2013.01); *H04W 4/80* (2018.02); *A61B 2560/0214* (2013.01); *A61B 2560/0462* (2013.01); *A61B 2562/08* (2013.01); *A61B 2562/162* (2013.01); *G06K 7/10366* (2013.01); *Y10T 29/49117* (2015.01)

(58) Field of Classification Search
CPC ... A61B 5/4833; A61B 5/4839; A61B 5/6861; A61B 5/7282; A61B 2560/0214; A61B 2560/0462; A61B 2562/08; A61B 2562/162; A61B 5/681; A61J 3/007; G06K 7/10168; G06K 7/10366; G16H 20/10; H04B 13/005; H01Q 1/273; H04W 4/80; Y10T 29/49117
USPC ........................................ 600/302; 340/10.1
See application file for complete search history.

(56) References Cited

U.S. PATENT DOCUMENTS

| | | |
|---|---|---|
| 2,973,555 A | 3/1961 | Schwepke |
| 3,048,526 A | 8/1962 | Boswell |
| 3,079,824 A | 3/1963 | Schott |
| 3,096,248 A | 7/1963 | Rudzki |
| 3,176,399 A | 4/1965 | Marino et al. |
| 3,589,943 A | 6/1971 | Grubb et al. |
| 3,607,788 A | 9/1971 | Adolph |
| 3,642,008 A | 2/1972 | Bolduc |
| 3,679,480 A | 7/1972 | Brown et al. |
| 3,682,160 A * | 8/1972 | Murata ................. A61B 5/42 600/302 |
| 3,719,183 A | 3/1973 | Schwartz |
| 3,799,802 A | 3/1974 | Schneble, Jr. et al. |
| 3,828,766 A | 8/1974 | Krasnow |
| 3,837,339 A | 9/1974 | Aisenberg et al. |
| 3,849,041 A | 11/1974 | Knapp |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,750 A | 12/1977 | Butler |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,106,348 A | 8/1978 | Auphan |
| 4,129,125 A | 12/1978 | Lester |
| 4,139,589 A | 2/1979 | Beringer et al. |
| 4,143,770 A | 3/1979 | Grimmell et al. |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,559,950 A | 12/1985 | Vaughan |
| 4,564,363 A | 1/1986 | Bagnall et al. |
| 4,635,641 A | 1/1987 | Hoffman |
| 4,654,165 A | 3/1987 | Eisenber |
| 4,663,250 A | 5/1987 | Ong et al. |
| 4,669,479 A | 6/1987 | Dunseath |
| 4,687,660 A | 8/1987 | Baker et al. |
| 4,725,997 A | 2/1988 | Urquhart et al. |
| 4,749,575 A | 6/1988 | Rotman et al. |
| 4,763,659 A | 8/1988 | Dunseath |
| 4,767,627 A | 8/1988 | Caldwell et al. |
| 4,775,536 A | 10/1988 | Patell |
| 4,784,162 A | 11/1988 | Ricks |
| 4,793,825 A | 12/1988 | Benjamin et al. |
| 4,814,181 A | 3/1989 | Jordan et al. |
| 4,844,076 A | 7/1989 | Lesho |
| 4,847,090 A | 7/1989 | Della Posta et al. |
| 4,876,093 A | 10/1989 | Theeuwes et al. |
| 4,891,223 A | 1/1990 | Ambegaonakar et al. |
| 4,896,261 A | 1/1990 | Nolan |
| 4,900,552 A | 2/1990 | Sanvordeker et al. |
| 4,975,230 A | 12/1990 | Pinkhasov |
| 4,987,897 A | 1/1991 | Funke |
| 5,000,957 A | 3/1991 | Eckenhoff |
| 5,016,634 A | 5/1991 | Vock et al. |
| 5,018,335 A | 5/1991 | Yamamoto et al. |
| 5,079,006 A | 1/1992 | Urquhart |
| 5,110,441 A | 5/1992 | Kinlen et al. |
| 5,160,885 A | 11/1992 | Hannam et al. |
| 5,167,626 A | 12/1992 | Casper |
| 5,176,626 A | 1/1993 | Soehendra |
| 5,187,723 A | 2/1993 | Mueller |
| 5,213,738 A | 5/1993 | Hampton et al. |
| 5,218,343 A | 6/1993 | Stobbe et al. |
| 5,261,402 A | 11/1993 | DiSabito |
| 5,263,481 A | 11/1993 | Axelgaard et al. |
| 5,273,066 A | 12/1993 | Graham et al. |
| 5,279,607 A | 1/1994 | Schentag et al. |
| 5,281,287 A | 1/1994 | Lloyd |
| 5,283,136 A | 2/1994 | Peled et al. |
| 5,288,564 A | 2/1994 | Klein |
| 5,305,745 A | 4/1994 | Zacouto |
| 5,310,301 A | 5/1994 | Aono |
| 5,318,557 A | 6/1994 | Gross |
| 5,331,953 A | 7/1994 | Andersson et al. |
| 5,394,882 A | 3/1995 | Mawhinney |
| 5,395,366 A | 3/1995 | D'Andrea et al. |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |

(56) References Cited

U.S. PATENT DOCUMENTS

| | | | |
|---|---|---|---|
| 5,458,994 A | 10/1995 | Nesselbeck et al. | |
| 5,485,841 A | 1/1996 | Watkin et al. | |
| 5,506,248 A | 4/1996 | Nikfar et al. | |
| 5,551,020 A | 8/1996 | Flax et al. | |
| 5,567,210 A | 10/1996 | Bates et al. | |
| 5,596,302 A | 1/1997 | Mastrocola et al. | |
| 5,600,548 A | 2/1997 | Nguyen et al. | |
| 5,603,363 A | 2/1997 | Nelson | |
| 5,634,468 A | 6/1997 | Platt | |
| 5,645,063 A | 7/1997 | Straka et al. | |
| 5,659,247 A | 8/1997 | Clements | |
| 5,703,463 A | 12/1997 | Smith | |
| 5,705,189 A | 1/1998 | Lehmann et al. | |
| 5,724,432 A | 3/1998 | Bouvet et al. | |
| 5,738,708 A | 4/1998 | Peachey et al. | |
| 5,740,811 A | 4/1998 | Hedberg | |
| 5,757,326 A | 5/1998 | Koyama et al. | |
| 5,772,575 A | 6/1998 | Lesinski et al. | |
| 5,792,048 A | 8/1998 | Schaefer | |
| 5,796,827 A * | 8/1998 | Coppersmith | G06K 19/07758 713/182 |
| 5,802,467 A | 9/1998 | Salazar | |
| 5,833,716 A | 11/1998 | Bar-Or | |
| 5,842,324 A | 12/1998 | Grosskopf et al. | |
| 5,845,265 A | 12/1998 | Woolston | |
| 5,862,803 A | 1/1999 | Besson | |
| 5,868,136 A | 2/1999 | Fox | |
| 5,914,132 A | 6/1999 | Kelm et al. | |
| 5,914,701 A * | 6/1999 | Gersheneld | G06F 3/017 345/156 |
| 5,925,030 A | 7/1999 | Gross et al. | |
| 5,957,854 A | 9/1999 | Besson et al. | |
| 5,963,132 A | 10/1999 | Yoakum et al. | |
| 5,974,124 A | 10/1999 | Schlueter, Jr. et al. | |
| 5,981,166 A | 11/1999 | Mandecki | |
| 5,999,846 A | 12/1999 | Pardey et al. | |
| 6,018,229 A | 1/2000 | Mitchell et al. | |
| 6,038,464 A | 3/2000 | Axelgaard et al. | |
| 6,042,710 A | 3/2000 | Dubrow | |
| 6,047,203 A | 4/2000 | Sackner | |
| 6,068,465 A | 5/2000 | Wilson | |
| 6,068,589 A | 5/2000 | Neukermans | |
| 6,076,016 A * | 6/2000 | Feierbach | A61B 5/0028 128/903 |
| 6,081,734 A | 6/2000 | Batz | |
| 6,091,975 A | 7/2000 | Daddona et al. | |
| 6,095,985 A | 8/2000 | Raymond et al. | |
| 6,115,636 A * | 9/2000 | Ryan | A61N 1/37223 128/903 |
| 6,122,351 A | 9/2000 | Schlueter, Jr. et al. | |
| 6,141,592 A | 10/2000 | Pauly | |
| 6,149,940 A | 11/2000 | Maggi et al. | |
| 6,200,265 B1 | 3/2001 | Walsh et al. | |
| 6,206,702 B1 | 3/2001 | Hayden et al. | |
| 6,211,799 B1 * | 4/2001 | Post | H04L 12/10 341/33 |
| 6,217,744 B1 | 4/2001 | Crosby | |
| 6,231,593 B1 | 5/2001 | Meserol | |
| 6,245,057 B1 | 6/2001 | Sieben et al. | |
| 6,269,058 B1 | 7/2001 | Yamanoi et al. | |
| 6,285,897 B1 | 9/2001 | Kilcoyne et al. | |
| 6,287,252 B1 | 9/2001 | Lugo | |
| 6,288,629 B1 | 9/2001 | Cofino et al. | |
| 6,289,238 B1 | 9/2001 | Besson et al. | |
| 6,315,719 B1 | 11/2001 | Rode et al. | |
| 6,317,714 B1 | 11/2001 | Del Castillo | |
| 6,342,774 B1 | 1/2002 | Kreisinger et al. | |
| 6,344,824 B1 | 2/2002 | Takasugi et al. | |
| 6,358,202 B1 | 3/2002 | Arent | |
| 6,364,834 B1 | 4/2002 | Reuss | |
| 6,366,206 B1 | 4/2002 | Ishikawa et al. | |
| 6,371,927 B1 | 4/2002 | Brune | |
| 6,374,670 B1 | 4/2002 | Spelman | |
| 6,380,858 B1 | 4/2002 | Yarin et al. | |
| 6,390,088 B1 | 5/2002 | Noehl et al. | |
| 6,394,997 B1 | 5/2002 | Lemelson | |
| 6,426,863 B1 | 7/2002 | Munshi | |
| 6,432,292 B1 | 8/2002 | Pinto et al. | |
| 6,440,069 B1 | 8/2002 | Raymond et al. | |
| 6,441,747 B1 | 8/2002 | Khair | |
| 6,453,199 B1 | 9/2002 | Kobozev | |
| 6,477,424 B1 | 11/2002 | Thompson et al. | |
| 6,496,705 B1 | 12/2002 | Ng et al. | |
| 6,526,315 B1 | 2/2003 | Inagawa | |
| 6,531,026 B1 | 3/2003 | Takeichi et al. | |
| 6,544,174 B2 | 4/2003 | West | |
| 6,547,994 B1 | 4/2003 | Monkhouse | |
| 6,564,079 B1 | 5/2003 | Cory | |
| 6,567,685 B2 | 5/2003 | Takamori et al. | |
| 6,572,636 B1 | 6/2003 | Hagen et al. | |
| 6,577,893 B1 | 6/2003 | Besson et al. | |
| 6,579,231 B1 | 6/2003 | Phipps | |
| 6,535,929 B1 | 7/2003 | Stivoric | |
| 6,599,284 B2 | 7/2003 | Faour et al. | |
| 6,602,518 B2 | 8/2003 | Seielstad et al. | |
| 6,605,038 B1 | 8/2003 | Teller | |
| 6,609,018 B2 | 8/2003 | Cory | |
| 6,612,984 B1 | 9/2003 | Kerr | |
| 6,632,175 B1 | 10/2003 | Marshall | |
| 6,632,216 B2 | 10/2003 | Houzego et al. | |
| 6,635,279 B2 | 10/2003 | Kolter et al. | |
| 6,643,541 B2 | 11/2003 | Mok et al. | |
| 6,654,638 B1 | 11/2003 | Sweeney | |
| 6,663,846 B1 | 12/2003 | McCombs | |
| 6,673,474 B2 | 1/2004 | Yamamoto | |
| 6,680,923 B1 | 1/2004 | Leon | |
| 6,689,117 B2 | 2/2004 | Sweeney et al. | |
| 6,694,161 B2 | 2/2004 | Mehrotra | |
| 6,704,602 B2 | 3/2004 | Berg et al. | |
| 6,720,923 B1 | 4/2004 | Hayward et al. | |
| 6,738,671 B2 | 5/2004 | Christophersom et al. | |
| 6,740,033 B1 | 5/2004 | Olejniczak et al. | |
| 6,745,082 B2 | 6/2004 | Axelgaard et al. | |
| 6,755,783 B2 | 6/2004 | Cosentino | |
| 6,757,523 B2 | 6/2004 | Fry | |
| 6,759,968 B2 | 7/2004 | Zierolf | |
| 6,767,200 B2 | 7/2004 | Sowden et al. | |
| 6,773,429 B2 | 8/2004 | Sheppard et al. | |
| 6,800,060 B2 | 10/2004 | Marshall | |
| 6,801,137 B2 | 10/2004 | Eggers et al. | |
| 6,816,794 B2 | 11/2004 | Alvi | |
| 6,822,554 B2 | 11/2004 | Vrijens et al. | |
| 6,824,512 B2 | 11/2004 | Warkentin et al. | |
| 6,836,862 B1 | 12/2004 | Erekson et al. | |
| 6,839,659 B2 | 1/2005 | Tarassenko et al. | |
| 6,840,904 B2 | 1/2005 | Goldberg | |
| 6,842,636 B2 | 1/2005 | Perrault | |
| 6,845,272 B1 | 1/2005 | Thomsen | |
| 6,864,780 B2 | 3/2005 | Doi | |
| 6,879,810 B2 | 4/2005 | Bouet | |
| 6,888,337 B2 | 5/2005 | Sawyers | |
| 6,889,165 B2 | 5/2005 | Lind et al. | |
| 6,909,878 B2 | 6/2005 | Haller | |
| 6,922,592 B2 | 7/2005 | Thompson et al. | |
| 6,928,370 B2 | 8/2005 | Anuzis et al. | |
| 6,929,636 B1 | 8/2005 | Von Alten | |
| 6,937,150 B2 | 8/2005 | Medema | |
| 6,942,616 B2 | 9/2005 | Kerr | |
| 6,942,770 B2 | 9/2005 | Cai et al. | |
| 6,946,156 B2 | 9/2005 | Bunick | |
| 6,951,536 B2 | 10/2005 | Yokoi | |
| 6,957,107 B2 | 10/2005 | Rogers et al. | |
| 6,958,603 B2 | 10/2005 | Kondo | |
| 6,960,617 B2 | 11/2005 | Omidian et al. | |
| 6,968,153 B1 | 11/2005 | Heinonen | |
| 6,977,511 B1 | 12/2005 | Patel et al. | |
| 6,982,094 B2 | 1/2006 | Sowden | |
| 6,987,965 B2 | 1/2006 | Ng et al. | |
| 6,990,082 B1 | 1/2006 | Zehavi et al. | |
| 7,002,476 B2 | 2/2006 | Rapchak | |
| 7,004,395 B2 | 2/2006 | Koenck | |
| 7,009,634 B2 | 3/2006 | Iddan et al. | |
| 7,009,946 B1 | 3/2006 | Kardach | |

(56) References Cited

U.S. PATENT DOCUMENTS

| | | | |
|---|---|---|---|
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,061,236 B2 | 6/2006 | Britton |
| 7,083,578 B2 | 8/2006 | Lewkowicz |
| 7,116,252 B2 | 10/2006 | Teraguchi |
| 7,118,531 B2 | 10/2006 | Krill |
| 7,122,143 B2 | 10/2006 | Sowden et al. |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,164,942 B2 | 1/2007 | Awahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,199 B2 | 3/2007 | Leung et al. |
| 7,188,767 B2 | 3/2007 | Penuela |
| 7,194,038 B1 | 3/2007 | Inkinen |
| 7,196,495 B1 | 3/2007 | Burcham |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,311,665 B2 | 12/2007 | Hawthorne |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,733 B2 | 5/2008 | Robbins |
| 7,376,435 B2 | 5/2008 | McGowan |
| 7,382,247 B2 | 6/2008 | Welch et al. |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,442,164 B2 | 10/2008 | Berrang et al. |
| 7,443,290 B2 * | 10/2008 | Takiguchi ............ H04B 5/0062 340/539.1 |
| 7,458,887 B2 | 12/2008 | Kurosawa |
| 7,469,838 B2 | 12/2008 | Brooks et al. |
| 7,471,665 B2 | 12/2008 | Perlman |
| 7,471,992 B2 | 12/2008 | Schmidt et al. |
| 7,492,128 B2 | 2/2009 | Shen |
| 7,499,674 B2 | 3/2009 | Salokannel |
| 7,510,121 B2 | 3/2009 | Koenck |
| 7,512,448 B2 | 3/2009 | Malick |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,527,807 B2 | 5/2009 | Choi et al. |
| 7,537,590 B2 | 5/2009 | Santini, Jr. et al. |
| 7,539,533 B2 | 5/2009 | Tran |
| 7,542,878 B2 | 6/2009 | Nanikashvili |
| 7,547,278 B2 | 6/2009 | Miyazaki et al. |
| 7,551,590 B2 | 6/2009 | Haller |
| 7,554,452 B2 | 6/2009 | Cole |
| 7,558,620 B2 | 7/2009 | Ishibashi |
| 7,575,005 B2 | 8/2009 | Mumford |
| 7,616,111 B2 | 11/2009 | Covannon |
| 7,617,001 B2 | 11/2009 | Penner et al. |
| 7,626,387 B2 | 12/2009 | Adachi |
| 7,639,473 B2 | 12/2009 | Hsu et al. |
| 7,640,802 B2 | 1/2010 | King et al. |
| 7,645,262 B2 | 1/2010 | Greenberg et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,672,714 B2 | 3/2010 | Kuo |
| 7,673,679 B2 | 3/2010 | Harrison et al. |
| 7,678,043 B2 | 3/2010 | Gilad |
| 7,686,839 B2 | 3/2010 | Parker |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Cosentino |
| 7,756,587 B2 | 7/2010 | Penner et al. |
| 7,760,104 B2 | 7/2010 | Asp |
| 7,782,991 B2 | 8/2010 | Sobchak et al. |
| 7,796,043 B2 | 9/2010 | Euliano et al. |
| 7,797,033 B2 | 9/2010 | D'Andrea et al. |
| 7,809,399 B2 | 10/2010 | Lu |
| 7,844,341 B2 | 11/2010 | Von Arx et al. |
| 7,881,799 B2 | 2/2011 | Greenberg et al. |
| 7,875,587 B2 | 7/2011 | Schneider |
| 7,878,064 B2 | 7/2011 | Zdeblick et al. |
| 7,978,064 B2 | 7/2011 | Zdeblick et al. |
| 7,983,189 B2 | 7/2011 | Bugenhagen |
| 8,036,731 B2 | 10/2011 | Kimchy et al. |
| 8,036,748 B2 | 10/2011 | Zdeblick et al. |
| 8,054,047 B2 | 11/2011 | Chen et al. |
| 8,054,140 B2 | 11/2011 | Fleming et al. |
| 8,055,334 B2 | 11/2011 | Savage et al. |
| 8,082,919 B2 | 12/2011 | Brunnberg et al. |
| 8,119,045 B2 | 2/2012 | Schmidt et al. |
| 8,131,376 B1 | 3/2012 | Faraji et al. |
| 8,172,762 B2 * | 5/2012 | Robertson .......... A61B 5/14535 600/506 |
| 8,177,611 B2 | 5/2012 | Kang |
| 8,185,191 B1 | 5/2012 | Shapiro et al. |
| 8,185,646 B2 | 5/2012 | Headley |
| 8,200,320 B2 | 6/2012 | Kovacs |
| 8,207,731 B2 | 6/2012 | Moskalenko |
| 8,224,596 B2 | 7/2012 | Agrawal et al. |
| 8,253,586 B1 | 8/2012 | Matak |

(56) References Cited

U.S. PATENT DOCUMENTS

| | | | |
|---|---|---|---|
| 8,254,853 B2 | 8/2012 | Rofougaran | |
| 8,271,146 B2 | 9/2012 | Heber et al. | |
| 8,298,574 B2 | 10/2012 | Tsabari et al. | |
| 8,343,068 B2 | 1/2013 | Najafi et al. | |
| 8,374,698 B2 | 2/2013 | Ok et al. | |
| 8,389,003 B2 | 3/2013 | Mintchev et al. | |
| 8,404,275 B2 | 3/2013 | Habboushe | |
| 8,425,492 B2 | 4/2013 | Herbert et al. | |
| 8,443,214 B2 | 5/2013 | Lee et al. | |
| 8,454,528 B2 | 6/2013 | Yuen et al. | |
| 8,532,776 B2 | 9/2013 | Greenberg et al. | |
| 8,540,664 B2 | 9/2013 | Robertson et al. | |
| 8,545,402 B2 | 10/2013 | Hafezi et al. | |
| 8,547,248 B2 * | 10/2013 | Zdeblick | A61B 5/418 340/870.28 |
| 8,558,563 B2 | 10/2013 | Zdeblick | |
| 8,564,432 B2 | 10/2013 | Covannon et al. | |
| 8,597,186 B2 | 12/2013 | Hafezi et al. | |
| 8,634,838 B2 | 1/2014 | Hellwig et al. | |
| 8,647,358 B2 | 2/2014 | Brister et al. | |
| 8,660,645 B2 | 2/2014 | Stevenson et al. | |
| 8,668,643 B2 | 3/2014 | Kinast | |
| 8,685,451 B2 | 4/2014 | Toneguzzo et al. | |
| 8,697,057 B2 | 4/2014 | Van Epps et al. | |
| 8,698,006 B2 | 4/2014 | Bealka et al. | |
| 8,758,237 B2 | 6/2014 | Sherman et al. | |
| 8,816,847 B2 | 6/2014 | Zdeblick et al. | |
| 8,784,308 B2 | 7/2014 | Duck et al. | |
| 8,802,183 B2 | 8/2014 | Frank et al. | |
| 8,836,513 B2 | 9/2014 | Hafezi et al. | |
| 8,838,217 B2 | 9/2014 | Myr | |
| 8,858,432 B2 | 10/2014 | Robertson | |
| 8,908,943 B2 | 12/2014 | Berry et al. | |
| 8,912,908 B2 | 12/2014 | Berkman et al. | |
| 8,926,509 B2 | 1/2015 | Magar et al. | |
| 8,932,221 B2 | 1/2015 | Colliou et al. | |
| 8,945,005 B2 | 2/2015 | Hafezi et al. | |
| 8,951,234 B2 | 2/2015 | Hafezi et al. | |
| 8,989,837 B2 | 3/2015 | Weinstein et al. | |
| 9,031,658 B2 | 5/2015 | Chiao et al. | |
| 9,088,168 B2 | 7/2015 | Mach et al. | |
| 9,107,806 B2 | 8/2015 | Hafezi et al. | |
| 9,119,554 B2 | 9/2015 | Robertson et al. | |
| 9,119,918 B2 | 9/2015 | Robertson et al. | |
| 9,149,423 B2 | 10/2015 | Duck et al. | |
| 9,158,890 B2 | 10/2015 | Meredith et al. | |
| 9,161,707 B2 | 10/2015 | Hafezi et al. | |
| 9,189,941 B2 | 11/2015 | Eschelman et al. | |
| 9,226,663 B2 | 1/2016 | Fei | |
| 9,226,679 B2 | 1/2016 | Balda | |
| 9,268,909 B2 | 2/2016 | Jani et al. | |
| 9,270,025 B2 | 2/2016 | Robertson et al. | |
| 9,271,897 B2 | 3/2016 | Costello et al. | |
| 9,277,864 B2 | 3/2016 | Yang et al. | |
| 9,320,455 B2 | 4/2016 | Hafezi et al. | |
| 9,415,010 B2 | 6/2016 | Hafezi et al. | |
| 9,433,371 B2 | 9/2016 | Hafezi et al. | |
| 9,439,582 B2 | 9/2016 | Berkman et al. | |
| 9,439,599 B2 | 9/2016 | Thompson et al. | |
| 9,517,012 B2 | 12/2016 | Lane et al. | |
| 9,537,010 B2 | 3/2017 | Thompson et al. | |
| 9,597,487 B2 | 3/2017 | Robertson et al. | |
| 9,599,679 B2 | 3/2017 | Taylor et al. | |
| 9,649,066 B2 | 5/2017 | Zdeblick et al. | |
| 9,681,842 B2 | 6/2017 | Zdeblick et al. | |
| 9,741,975 B2 | 8/2017 | Laulicht et al. | |
| 9,756,874 B2 | 9/2017 | Arne et al. | |
| 9,968,284 B2 | 5/2018 | Vidalis et al. | |
| 2001/0027331 A1 | 10/2001 | Thompson | |
| 2001/0044588 A1 | 11/2001 | Mault | |
| 2001/0051766 A1 | 12/2001 | Gazdinski | |
| 2002/0002326 A1 | 1/2002 | Causey et al. | |
| 2002/0026111 A1 | 2/2002 | Ackerman | |
| 2002/0032384 A1 | 3/2002 | Raymond et al. | |
| 2002/0032385 A1 | 3/2002 | Raymond et al. | |
| 2002/0040278 A1 | 4/2002 | Anuzis et al. | |
| 2002/0077620 A1 | 6/2002 | Sweeney et al. | |
| 2002/0099423 A1 | 7/2002 | Berg et al. | |
| 2002/0128934 A1 | 9/2002 | Shaer | |
| 2002/0132226 A1 | 9/2002 | Nair | |
| 2002/0136744 A1 | 9/2002 | McGlynn et al. | |
| 2002/0179921 A1 | 12/2002 | Cohn | |
| 2002/0192159 A1 | 12/2002 | Reitberg | |
| 2002/0193669 A1 | 12/2002 | Giukhovsky | |
| 2002/0198470 A1 | 12/2002 | Imran et al. | |
| 2003/0017826 A1 | 1/2003 | Fishman et al. | |
| 2003/0023150 A1 | 1/2003 | Yokoi et al. | |
| 2003/0028226 A1 | 2/2003 | Thompson | |
| 2003/0062551 A1 | 4/2003 | Chen et al. | |
| 2003/0065536 A1 | 4/2003 | Hansen | |
| 2003/0076179 A1 | 4/2003 | Branch et al. | |
| 2003/0083559 A1 | 5/2003 | Thompson | |
| 2003/0091625 A1 | 5/2003 | Hariharan et al. | |
| 2003/0126593 A1 | 7/2003 | Mault | |
| 2003/0130714 A1 | 7/2003 | Nielsen et al. | |
| 2003/0135128 A1 | 7/2003 | Suffin et al. | |
| 2003/0135392 A1 | 7/2003 | Vrijens et al. | |
| 2003/0152622 A1 | 8/2003 | Louie-Heim et al. | |
| 2003/0158466 A1 | 8/2003 | Lynn et al. | |
| 2003/0158756 A1 | 8/2003 | Abramson | |
| 2003/0162556 A1 | 8/2003 | Libes | |
| 2003/0164401 A1 | 9/2003 | Andreasson et al. | |
| 2003/0167000 A1 | 9/2003 | Mullick et al. | |
| 2003/0171791 A1 | 9/2003 | KenKnight | |
| 2003/0171898 A1 | 9/2003 | Tarassenko et al. | |
| 2003/0181788 A1 | 9/2003 | Yokoi et al. | |
| 2003/0185286 A1 | 10/2003 | Yuen | |
| 2003/0187337 A1 | 10/2003 | Tarassenko et al. | |
| 2003/0187338 A1 | 10/2003 | Say | |
| 2003/0195403 A1 | 10/2003 | Berner et al. | |
| 2003/0213495 A1 | 11/2003 | Fujita et al. | |
| 2003/0214579 A1 | 11/2003 | Iddan | |
| 2003/0216622 A1 | 11/2003 | Meron et al. | |
| 2003/0216625 A1 | 11/2003 | Phipps | |
| 2003/0216666 A1 | 11/2003 | Ericson et al. | |
| 2003/0216729 A1 | 11/2003 | Marchitto | |
| 2003/0219484 A1 | 11/2003 | Sowden et al. | |
| 2003/0232895 A1 | 12/2003 | Omidian et al. | |
| 2004/0008123 A1 | 1/2004 | Carrender et al. | |
| 2004/0018476 A1 | 1/2004 | LaDue | |
| 2004/0034295 A1 | 2/2004 | Salganicoff | |
| 2004/0049245 A1 | 3/2004 | Gass | |
| 2004/0073095 A1 | 4/2004 | Causey et al. | |
| 2004/0073454 A1 | 4/2004 | Urquhart | |
| 2004/0077995 A1 | 4/2004 | Ferek-Petric | |
| 2004/0082982 A1 | 4/2004 | Gord et al. | |
| 2004/0067839 A1 | 5/2004 | Raymond et al. | |
| 2004/0092801 A1 | 5/2004 | Drakulic | |
| 2004/0106859 A1 | 6/2004 | Say et al. | |
| 2004/0115507 A1 | 6/2004 | Potter et al. | |
| 2004/0115517 A1 | 6/2004 | Fukada et al. | |
| 2004/0117062 A1 | 6/2004 | Bonney et al. | |
| 2004/0121015 A1 | 6/2004 | Chidlaw et al. | |
| 2004/0148140 A1 | 7/2004 | Tarassenko et al. | |
| 2004/0153007 A1 | 8/2004 | Harris | |
| 2004/0167226 A1 | 8/2004 | Serafini | |
| 2004/0167465 A1 | 8/2004 | Mihai et al. | |
| 2004/0167801 A1 | 8/2004 | Say et al. | |
| 2004/0193020 A1 | 9/2004 | Chiba | |
| 2004/0193029 A1 | 9/2004 | Gluhovsky | |
| 2004/0193446 A1 | 9/2004 | Mayer et al. | |
| 2004/0199222 A1 | 10/2004 | Sun et al. | |
| 2004/0215084 A1 | 10/2004 | Shimizu et al. | |
| 2004/0218683 A1 | 11/2004 | Batra | |
| 2004/0220643 A1 | 11/2004 | Schmidt | |
| 2004/0224644 A1 | 11/2004 | Wu | |
| 2004/0225199 A1 | 11/2004 | Evanyk | |
| 2004/0253304 A1 | 12/2004 | Gross et al. | |
| 2004/0258571 A1 | 12/2004 | Lee et al. | |
| 2004/0259899 A1 | 12/2004 | Sanghvi et al. | |
| 2004/0260154 A1 | 12/2004 | Sidelnik | |
| 2005/0003074 A1 | 1/2005 | Brown et al. | |
| 2005/0017841 A1 | 1/2005 | Doi et al. | |
| 2005/0020887 A1 | 1/2005 | Goldberg | |

(56) References Cited

U.S. PATENT DOCUMENTS

| | | |
|---|---|---|
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0075145 A1 | 4/2005 | Dvorak et al. |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0143623 A1 | 6/2005 | Kojima |
| 2005/0146594 A1 | 7/2005 | Nakatani et al. |
| 2005/0148883 A1 | 7/2005 | Boesen |
| 2005/0154428 A1* | 7/2005 | Bruinsma ............... A61N 1/40 607/60 |
| 2005/0156709 A1 | 7/2005 | Gilbert et al. |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0208251 A1 | 9/2005 | Aisenbrey |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0279054 A1 | 12/2005 | Mauze et al. |
| 2005/0280539 A1 | 12/2005 | Pettus |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1* | 3/2006 | Lovoi ............... A61K 9/2072 340/572.1 |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0077616 A1* | 4/2006 | Takiguchi ............ H04B 13/005 361/231 |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122494 A1 | 6/2006 | Bouchoucha |
| 2006/0122667 A1 | 6/2006 | Chavan et al. |
| 2006/0129060 A1 | 6/2006 | Lee et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Giukhovsky et al. |
| 2006/0155183 A1 | 7/2006 | Kroecker |
| 2006/0158820 A1* | 7/2006 | Takiguchi ............ H04B 13/005 361/231 |
| 2006/0161225 A1 | 7/2006 | Sormann et al. |
| 2006/0178109 A1* | 8/2006 | Takiguchi ............ H04B 13/005 455/41.1 |
| 2006/0179949 A1 | 8/2006 | Kim |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0029195 A1 | 2/2007 | Li et al. |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Femen et al. |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0173347 A1 | 8/2007 | Tarassenko et al. |
| 2007/0179371 A1 | 8/2007 | Peyser et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0000804 A1 | 1/2008 | Carey et al. |
| 2008/0014866 A1 | 1/2008 | Lipowshi |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |

(56) References Cited

U.S. PATENT DOCUMENTS

| | | |
|---|---|---|
| 2008/0033273 A1 | 2/2008 | Zhou |
| 2008/0038588 A1 | 2/2008 | Lee |
| 2008/0039700 A1 | 2/2008 | Drinan et al. |
| 2008/0044721 A1 | 2/2008 | Heller et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0058614 A1 | 3/2008 | Banet |
| 2008/0058630 A1* | 3/2008 | Robertson ............. A61B 5/026 600/368 |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0103440 A1 | 5/2008 | Ferren et al. |
| 2008/0112885 A1 | 5/2008 | Okunev et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Masholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBeouf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0284599 A1 | 11/2008 | Zdeblick et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1* | 12/2008 | Zdeblick ............. A61N 1/37217 600/302 |
| 2008/0306360 A1 | 12/2008 | Robertson et al. |
| 2008/0311852 A1 | 12/2008 | Hansen |
| 2008/0312522 A1 | 12/2008 | Rowlandson |
| 2008/0316020 A1 | 12/2008 | Robertson |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Jeso |
| 2009/0043171 A1 | 2/2009 | Rule |
| 2009/0047357 A1 | 2/2009 | Tomohira et al. |
| 2009/0048498 A1 | 2/2009 | Riskey |
| 2009/0062634 A1 | 3/2009 | Say et al. |
| 2009/0062670 A1 | 3/2009 | Sterling |
| 2009/0062730 A1 | 3/2009 | Woo |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0069724 A1 | 3/2009 | Otto et al. |
| 2009/0076343 A1 | 3/2009 | James et al. |
| 2009/0076350 A1 | 3/2009 | Bly et al. |
| 2009/0082645 A1 | 3/2009 | Hafezi et al. |
| 2009/0087483 A1 | 4/2009 | Sison |
| 2009/0088618 A1 | 4/2009 | Arneson |
| 2009/0099435 A1 | 4/2009 | Say et al. |
| 2009/0110148 A1 | 4/2009 | Zhang |
| 2009/0112626 A1 | 4/2009 | Talbot |
| 2009/0165561 A1 | 4/2009 | Boydon et al. |
| 2009/0124871 A1 | 5/2009 | Arshak |
| 2009/0124965 A1 | 5/2009 | Greenberg et al. |
| 2009/0131774 A1 | 5/2009 | Sweitzer |
| 2009/0135886 A1 | 5/2009 | Robertson et al. |
| 2009/0142853 A1 | 6/2009 | Warrington et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0171420 A1 | 7/2009 | Brown et al. |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0194747 A1 | 8/2009 | Zou et al. |
| 2009/0197068 A1 | 8/2009 | Yamaguchi et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |

(56) References Cited

U.S. PATENT DOCUMENTS

| | | |
|---|---|---|
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256732 A1 | 10/2009 | Robertson |
| 2009/0260212 A1 | 10/2009 | Schmett et al. |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0281539 A1 | 11/2009 | Selig |
| 2009/0287109 A1 | 11/2009 | Ferren et al. |
| 2009/0295548 A1 | 12/2009 | Ronkka et al. |
| 2009/0296677 A1 | 12/2009 | Mahany et al. |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0010330 A1 | 1/2010 | Rankers |
| 2010/0033324 A1 | 2/2010 | Shimizu et al. |
| 2010/0036269 A1 | 2/2010 | Ferren et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0139672 A1 | 6/2010 | Kroll et al. |
| 2010/0168659 A1 | 7/2010 | Say et al. |
| 2010/0179398 A1 | 7/2010 | Say et al. |
| 2010/0191073 A1 | 7/2010 | Tarassenko et al. |
| 2010/0210299 A1 | 8/2010 | Gorbachov |
| 2010/0222652 A1 | 9/2010 | Cho |
| 2010/0228113 A1 | 9/2010 | Soiosko |
| 2010/0233026 A1 | 9/2010 | Ismagilov et al. |
| 2010/0234706 A1 | 9/2010 | Giiland |
| 2010/0234715 A1 | 9/2010 | Shin |
| 2010/0234914 A1 | 9/2010 | Shen |
| 2010/0245091 A1 | 9/2010 | Singh |
| 2010/0249541 A1 | 9/2010 | Geva et al. |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0274111 A1 | 10/2010 | Say et al. |
| 2010/0238730 A1 | 11/2010 | Tarassenko et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0297640 A1 | 11/2010 | Kumar et al. |
| 2010/0298650 A1 | 11/2010 | Moon et al. |
| 2010/0298668 A1 | 11/2010 | Hafezi et al. |
| 2010/0312188 A1 | 12/2010 | Robertson et al. |
| 2010/0312580 A1 | 12/2010 | Tarassenko et al. |
| 2011/0009715 A1 | 1/2011 | O'Reilly et al. |
| 2011/0065983 A1 | 3/2011 | Hafezi et al. |
| 2011/0077660 A1 | 3/2011 | Janik et al. |
| 2011/0124983 A1 | 5/2011 | Kroll et al. |
| 2011/0134906 A1 | 6/2011 | Garudadri et al. |
| 2011/0160549 A1 | 6/2011 | Saroka et al. |
| 2011/0224912 A1 | 9/2011 | Bhavaraju et al. |
| 2011/0230732 A1 | 9/2011 | Edman et al. |
| 2011/0270135 A1 | 11/2011 | Dooley et al. |
| 2012/0004520 A1 | 1/2012 | Whitworth et al. |
| 2012/0011699 A1 | 1/2012 | Hafezi et al. |
| 2012/0016231 A1 | 1/2012 | Westmoreland |
| 2012/0032816 A1 | 2/2012 | Cho et al. |
| 2012/0062371 A1 | 3/2012 | Radivojevic et al. |
| 2012/0071743 A1 | 3/2012 | Todorov et al. |
| 2012/0109112 A1 | 5/2012 | Strand et al. |
| 2012/0179004 A1 | 7/2012 | Roesicke et al. |
| 2012/0245043 A1 | 9/2012 | England |
| 2012/0276451 A1 | 11/2012 | Lestriez et al. |
| 2012/0299723 A1 | 11/2012 | Hafezi et al. |
| 2013/0129869 A1 | 5/2013 | Hafezi et al. |
| 2013/0129872 A1 | 5/2013 | Kruger |
| 2013/0131283 A1 | 5/2013 | Wang et al. |
| 2013/0171536 A1 | 7/2013 | French |
| 2013/0172690 A1 | 7/2013 | Arne et al. |
| 2013/0185228 A1 | 7/2013 | Dresner |
| 2013/0196012 A1 | 8/2013 | Dill |
| 2013/0199662 A1 | 8/2013 | Gebbink |
| 2013/0209877 A1 | 8/2013 | Kren et al. |
| 2013/0223028 A1 | 8/2013 | Arne et al. |
| 2013/0275296 A1 | 10/2013 | Tietzen et al. |
| 2014/0051965 A1* | 2/2014 | Zdeblick ............ A61B 5/14535 600/407 |
| 2014/0066734 A1 | 6/2014 | Zdebiick |
| 2014/0179221 A1 | 6/2014 | Whitworth et al. |
| 2014/0180202 A1 | 6/2014 | Zdeblick et al. |
| 2014/0280125 A1 | 9/2014 | Bhardwaj et al. |
| 2014/0308930 A1 | 10/2014 | Tran |
| 2014/0349256 A1 | 11/2014 | Connor |
| 2014/0374276 A1 | 12/2014 | Guthrie et al. |
| 2015/0017486 A1 | 1/2015 | Lai |
| 2015/0059922 A1 | 3/2015 | Thompson et al. |
| 2015/0060678 A1 | 3/2015 | Frank et al. |
| 2015/0060679 A1 | 3/2015 | Frank et al. |
| 2015/0060680 A1 | 3/2015 | Zdeblick et al. |
| 2015/0112243 A1 | 4/2015 | Hafezi et al. |
| 2015/0127737 A1 | 5/2015 | Thompson et al. |
| 2015/0127738 A1 | 5/2015 | Thompson et al. |
| 2015/0149375 A1 | 5/2015 | Thompson et al. |
| 2015/0150480 A1 | 6/2015 | Zdeblick et al. |
| 2015/0164746 A1 | 6/2015 | Costello et al. |
| 2015/0230729 A1* | 8/2015 | Zdeblick ............ G06K 7/10168 600/302 |
| 2015/0248833 A1 | 9/2015 | Arne et al. |
| 2015/0352343 A1 | 12/2015 | Hafezi et al. |
| 2015/0361234 A1 | 12/2015 | Hafezi et al. |
| 2016/0033667 A1 | 2/2016 | Schmidt et al. |
| 2016/0345906 A1 | 12/2016 | Johnson et al. |
| 2016/0380708 A1 | 12/2016 | Dua et al. |
| 2017/0000179 A1 | 1/2017 | Cheng et al. |
| 2017/0014046 A1 | 1/2017 | Hafezi et al. |
| 2017/0020162 A1 | 1/2017 | Schmidt et al. |
| 2017/0216569 A1 | 8/2017 | Hafezi et al. |
| 2017/0265813 A1 | 9/2017 | Zdeblick et al. |
| 2017/0274194 A1 | 9/2017 | Robertson et al. |
| 2017/0296799 A1 | 10/2017 | Hafezi et al. |
| 2018/0026680 A1 | 1/2018 | Shirvani et al. |
| 2018/0110441 A1 | 4/2018 | Frank et al. |
| 2018/0184698 A1 | 7/2018 | Arne et al. |
| 2018/0229996 A1 | 8/2018 | Thompson |

(56) References Cited

U.S. PATENT DOCUMENTS

FOREIGN PATENT DOCUMENTS

| | | |
|---|---|---|
| CN | 101795202 | 8/2010 |
| DE | 10313005 | 10/2004 |
| EP | 0344939 | 12/1989 |
| EP | 0526166 | 2/1993 |
| EP | 0981152 | 2/2000 |
| EP | 1246356 | 10/2002 |
| EP | 1534054 | 5/2005 |
| EP | 1702553 | 9/2006 |
| EP | 1244308 | 12/2007 |
| EP | 2143369 | 1/2010 |
| GB | 827762 | 2/1960 |
| JP | 61072712 | 4/1986 |
| JP | H01285247 | 11/1989 |
| JP | 05228128 | 9/1993 |
| JP | H11195415 | 7/1999 |
| JP | 2000506410 | 5/2000 |
| JP | 2002282219 | 10/2002 |
| JP | 2003050867 | 2/2003 |
| JP | 2004313242 | 11/2004 |
| JP | 2005073886 | 3/2005 |
| JP | 2005087552 | 4/2005 |
| JP | 2005102959 | 4/2005 |
| JP | 2005124708 | 5/2005 |
| JP | 2005514966 | 5/2005 |
| JP | 2005304880 | 11/2005 |
| JP | 2005343515 | 12/2005 |
| JP | 20055332328 | 12/2005 |
| JP | 2006006377 | 1/2006 |
| JP | 2006509574 | 3/2006 |
| JP | 2007200739 | 8/2007 |
| JP | 2002263185 | 9/2007 |
| JP | 2007313340 | 12/2007 |
| JP | 2009514870 | 4/2009 |
| JP | 2009528909 | 8/2009 |
| KR | 200600977523 | 7/2006 |
| TW | 200406192 | 5/2004 |
| TW | 200916136 | 4/2009 |
| WO | WO1988002237 | 4/1988 |
| WO | WO1992021307 | 12/1992 |
| WO | WO1993008734 | 5/1993 |
| WO | WO1993019667 | 10/1993 |
| WO | WO1994001165 | 1/1994 |
| WO | WO1997039963 | 10/1997 |
| WO | WO1998043537 | 10/1998 |
| WO | WO1999037290 | 7/1999 |
| WO | WO1999059465 | 11/1999 |
| WO | WO2000032474 | 6/2000 |
| WO | WO2000033246 | 6/2000 |
| WO | WO2001000085 | 1/2001 |
| WO | WO2001047466 | 7/2001 |
| WO | 2001058236 | 8/2001 |
| WO | WO2001074011 | 10/2001 |
| WO | WO2001080731 | 11/2001 |
| WO | WO2002000920 | 1/2002 |
| WO | WO2002045489 | 6/2002 |
| WO | WO2002058330 | 7/2002 |
| WO | WO2002062276 | 8/2002 |
| WO | WO2002087681 | 11/2002 |
| WO | WO2002095351 | 11/2002 |
| WO | WO2003005877 | 1/2003 |
| WO | WO2003050643 | 6/2003 |
| WO | WO2003068061 | 8/2003 |
| WO | WO2004014225 | 2/2004 |
| WO | WO2004019172 | 3/2004 |
| WO | WO2004039256 | 5/2004 |
| WO | WO2004066833 | 8/2004 |
| WO | WO2004066834 | 8/2004 |
| WO | WO2004066903 | 8/2004 |
| WO | WO2004068881 | 8/2004 |
| WO | WO2004075032 | 9/2004 |
| WO | WO2004109316 | 12/2004 |
| WO | WO2005011237 | 2/2005 |
| WO | WO2005020023 | 3/2005 |
| WO | WO2005024687 | 3/2005 |
| WO | WO2005041438 | 5/2005 |
| WO | WO2005047837 | 5/2005 |
| WO | WO2005051166 | 6/2005 |
| WO | WO2005053517 | 6/2005 |
| WO | WO2005083621 | 9/2005 |
| WO | WO2005110238 | 11/2005 |
| WO | WO2005123569 | 12/2005 |
| WO | WO2006021932 | 3/2006 |
| WO | WO2006028347 | 3/2006 |
| WO | WO2008027586 | 3/2006 |
| WO | WO2006055892 | 5/2006 |
| WO | WO2006055956 | 5/2006 |
| WO | WO2006075016 | 7/2006 |
| WO | WO2006100620 | 9/2006 |
| WO | WO2006104843 | 10/2006 |
| WO | WO2006116718 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | WO2007127316 | 11/2007 |
| WO | WO2007127879 | 11/2007 |
| WO | WO2007128165 | 11/2007 |
| WO | WO2007130491 | 11/2007 |
| WO | WO2007143535 | 12/2007 |
| WO | WO2007149546 | 12/2007 |
| WO | WO2008008281 | 1/2008 |
| WO | WO2008012700 | 1/2008 |
| WO | WO2008030482 | 3/2008 |
| WO | WO2008052136 | 5/2008 |
| WO | WO2008063626 | 5/2008 |
| WO | WO2008066617 | 6/2008 |
| WO | WO2008076464 | 6/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009000447 | 12/2008 |
| WO | WO2009001108 | 12/2008 |
| WO | WO2009006615 | 1/2009 |
| WO | WO2009029453 | 3/2009 |
| WO | WO2009031149 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010080765 | 7/2010 |
| WO | WO2010080843 | 7/2010 |
| WO | WO2010107563 | 9/2010 |

(56) References Cited

FOREIGN PATENT DOCUMENTS

| WO | WO2010129288 | 11/2010 |
|---|---|---|
| WO | WO2010132331 | 11/2010 |
| WO | WO2010135516 | 11/2010 |
| WO | WO2011068963 | 6/2011 |
| WO | WO2011133799 | 10/2011 |
| WO | WO201115933 S | 12/2011 |
| WO | WO2011159337 | 12/2011 |
| WO | WO2011159338 | 12/2011 |
| WO | WO2011159339 | 12/2011 |
| WO | WO2012112561 | 8/2012 |
| WO | WO2015112603 | 7/2015 |
| WO | WO2015112604 | 7/2015 |
| WO | WO2015119911 | 8/2015 |

OTHER PUBLICATIONS

Arshak et al., A Review and Adaptation of Methods of Object Tracking to Telemetry Capsules IC-Med (2007) vol. 1, No. 1, Issue 1, 12pp.

"ASGE Technology Status Evaluation Report: wireless capsule endoscopy" American Soc. For Gastrointestinal Endoscopy (2006) vol. 63, No. 4; 7 pp.

Au-Yeung, K., et al., "A Networked System for Self-Management of Drug Therapy and Wellness", Wireless Health '10, Oct. 5-7, 2010, San Diego, 9 pages.

Aydin et al., "Design and implementation considerations for an advanced wireless interface in miniaturized integrated sensor Microsystems" Sch. of Eng. & Electron., Edinburgh Univ., UK; (2003); abstract (1 page).

Barrie, Heidelberg pH capsule gastric analysis. Texbook of Natural Medicine, (1992), Pizzomo, Murray & Barrie (4 pages).

Bohidar et al., "Dielectric. Behavior of Gelatin Solutions and Gels" Colloid Polym Sci (1998) 276:81-86.

Brock, "Smart Medicine: The Application of Auto-ID Technology to Healthcare" Auto-ID Labs (2002) http://www.autoidlabs.org/uploads/media/MIT-AUTOID-WH-010.pdf (14 pages).

Carlson et al., "Evaluation of a non-invasive respiratory monitoring system for sleeping subjects" Physiological Measurement (1999) 20(1): 53.

Coury, L. "Conductance Measurement Part 1: Theory"; Current Separations, 18:3 (1999) p. 91-96.

Delvaux et al., "Capsule endoscopy: Technique and indications" Clinical Gastroenterology (2008) vol. 22, Issue 5, pp. 813-837.

Description of ePatch Technology Platform for ECG and EMG, located it http://www.madebydelta.com/imported/images/DELTA_Web/documents/ME/ePatch_ECG_EMG.pd, Dated Sep. 2, 2010; 1 page.

Dhar et al.. "Electroless nickel plated contacts on porous silicon" Appl. Phys. Lett. 68 (10) pp. 1392-1393 (1996).

Eldek A., "Design of double dipole antenna with enhanced usable bandwidth for wideband phased array applications" Progress in Electromagnetics Research PIER 59, 1-15 (2006).

Fawaz et al., "Enhanced Telemetry System using CP-QFSK Band—Pass Modulation Technique Suitable for Smart Pill Medical Application" IFIP IEEE Dubai Conference (2008); http://www.asic.fh-offenburg.de/downioads/ePille/IFIP_IEEE_Dubai_Conference.pdf (5 pages).

Ferguson et al., "Dielectric Constant Studies III Aqueous Gelatin Solutions" J. Chem. Phys. 2, 94 (1934) p. 94-98.

Furse C. M., "Dipole Antennas" J. Webster (ed). Wiley Encyclopedia of Electrical and Electronics Engineering (1999) p. 575-581.

Gaglani S. "Put Your Phone, Or Skin, on Vibrate" MedGadget (2012) http://medgadget.com/2012/03/put-your-phone-or-skin-on-vibrate.html 8pp.

Gilson, D.R. "Molecular dynamics simulation of dipole interactions", Department of Physics, Hull University, Dec. (2002), p. 1-43.

Given Imaging, "Agile Patency Brochure" (2006) http://www.inclino.no/documents/AgilePatencyBrochure_Global_GMB-0118-01.pdf; 4pp.

Gonzalez-Guillaumin et al.. "Ingestible capsule for impedance and pH monitoring in the esophagus" IEEE Trans Biomed Eng. (2007) 54(12): 2231-6; abstract.

Greene, "Edible RFID microchip monitor can tell if you take your medicine" Bloomberg Businessweek (2010) 2 pp.; http://www.businessweek.com/idg/2010-03-31/edible-ifid-microchip-monitor-can-tell-if-you-take-your-medicine.html (1 page).

Heydari et al., "Analysis of the PLL jitter due to power/ground and substrate noise"; IEEE Transactions on Circuits and Systems (2004) 51(12): 2404-16.

Hoeksma, J. "New 'smart pill' to track adherence" E-Health-Insider (2010) http://www.e-health-insider.com/news/5910/new_'smart_pill'_monitors_medicines (1 page).

Hoover et al., "Rx for health: Engineers design pill that signals it has been swallowed" University of Florida News (2010) 2pp.; http://news.ufl.edu/2010/03/31/antenna-pill-2/.

Intromedic, MicroCam Innovative Capsule Endoscope Pamphlet. (2006) 8 pp (http://www.intromedic.com/en/product/productinfo.asp) (8 pages).

ISET—Ion Sensitive Field-Effect Transistor; Microsens S.A. pdf document. Office Action dated Jun. 13 (2011) for U.S. Appl. No. 12/238,345; 4pp.

Jung, S. "Dissolvable 'Transient Electronics' Will Be Good For Your Body and the Environment" MedGadget; Oct. 1 (2012); Online website: http://medgadget com/2012/10/dissolvable-transient-electronics-will-be-good-for-your-body-and-the-environment.html; downloaded Oct. 24, 2012; 4 pp.

Juvenile Diabetes Research Foundation International (JDRF), "Artificial Pancreas Project" (2010); http://www.artificialpancreasproject.com/; 3 pp.

Kamada K., "Electrophoretic deposition assisted by soluble anode" Materials Letters 57 (2003) 2348-2351.

Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. p. 1-6.

Kim et al., "A Semi-Interpenetrating Network System for a Polymer Membrane"; Eur. Polym. J. vol. 33 No. 7; pp. 1009-1014 (1997).

Li, P-Y, et al. "An electrochemical intraocular drug delivery device", Sensors and Actuators A 143 (2008) p. 41-48.

Lifescan, "OneTouch UltraLink™" http://www.lifescan.com/products/meters/ultralink (2010) 2 pp.

Mackay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.

Mackay et al., "Endoradiosonde" Nature, (1957) 1239-1240, 179 Nature Publishing Group.

McKenzie et al., "Validation of a new telemetric core temperature monitor" J. Therm. Biol. (2004) 29(7-8):605-11.

Medtronic, "CareLink Therapy Management Software for Diabetes" (2010); https://carelink.minimed.com/patient/entry.jsp?bhcp=1; 1 pp.

Medtronic, "Carelink™ USB" (2008) http://www.medtronicdiabetes.com/pdf/carelink._usb_factsheet.pdf 2pp.

Medtronic "The New MiniMed Paradigm® REAL-Time Revel™ System" (2010) http://www.medtronicdiabetes.com/products/index.html; 2 pp.

Medtronic, "Mini Med Paradigm ® Revel ™ Insulin Pump" (2010) http://www.medtronicdiabetes.com/products/insulinpumps/index.html; 2 pp.

Medtronic, Mini Med Paradigm™ Veo™ System: Factsheet (2010). http://www.medtronic-diabetes.com.au/downloads/Paradigm%20Veo%20Factsheet.pdf; 4 pp.

Melanson, "Walkers swallow RFID pills for science" Engadget (2008); http://www.engadget.com/2008/07/29/walkers-swallow-rfid-pills-for-science/ (1 page).

Minimitter Co. Inc. "Actiheart" Traditional 510(k) Summary Sep. 27 (2005) (8 pages).

Minimitter Co. Inc. Noninvasive technology to help your studies succeed. Mini Mitter.com Mar. 31 (2009) (4 pages).

(56) References Cited

OTHER PUBLICATIONS

Mini Mitter Co, Inc. 510(k) Premarket Notification Mini-Logger for Diagnostic Spirometer. 9-21 (1999) (9 pages).
Mini Mitter Co, Inc. 510(%) Premarket Notification for VitalSense Apr. 22, 2004 (11 pages).
Minimitter Co. Inc. VitalSense Integrated Physiological Monitoring System. Product Description. (2005) (4 pages).
Minimitter Co. Inc. VitalSense Wireless Vital Signs Monitoring. Temperatures.com Mar. 31, 2009 (3 pages).
Mojaverian et al., "Estimation of gastric residence time of the Heidelberg capsule in humans: effect of varying food composition" Gastroenterology (1985) 89:(2): 392-7.
O'Brien et al., "The Production and Characterization of Chemically Reactive Porous Coatings of Zirconium Via Unbalanced Magnetron Sputtering" Surface and Coatings Technology (1996) 86-87; 200-206.
Park, "Medtronic to Buy MiniMed for $3.7 Billion" (2001) HomeCare; http://homecaremag.com/mag/medical_medtronic_buy_minimed/; 2 pp.
Radio Antennae, http://www.erikdeman.de/html/sail018h.htm; (2008) 5 pages.
"RFID "pill" monitors marchers" RFID News (2008) http://www.rfidnews.org/2008/07/23/rfid-pill-monitors-marchers/ (4 pages).
Rolison et al., "Electrically conductive oxide aerogels: new materials in elechochemistry" J. Mater. Chem. (2001) 1, 963-980.
Roulstone, et al., "Studies on Polymer Latex Films: I. A study of latex film morphology" Polymer international 24 (1991) pp. 87-94.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Santini, J.T. et al., "Microchips as controlled drug delivery-devices". Agnew. Chem. Int. Ed. (2000), vol. 39, p. 2396-2407.
"SensiVida minimally invasive clinical systems" Investor Presentation Oct. (2009) 28pp; http://www.sensividamedtech.com/SensiVidaGeneralOctober09.pdf; pp. 1-28.
Shawgo, R.S. et al. "BioMEMS from drug delivery", Current Opinion in Solid State and Material Science (102), p. 329-334.
Shin et al., "A Simple Route to Metal Nanodots and Nanoporous Metal Films"; Nano Letters, vol. 2, No. 9 (2002) pp. 933-936.
Shirivas et al., "A New Platform for Bioelectronics-Electronic Pill", Cummins College, (2010).; http://www.cumminscollege.org/downloads/eledronics_and_telecommunication/Newsletters/Current%20Newsletters.pdf; First cited in third party client search condudted by Patent Eagle Search May 18, 2010 (2010); pp. 11-12.
"Smartlife awarded patent for knitted transducer" Innovation in Textiles News: http://www.innovationintextiles.com/articles/208.php; 2pp. (2003).
"The SmartPill Wireless Motility Capsule" SMARTPILL, The Measure of GI Health; (2010) http://www.smartpillcorp.com/index.cfm?pagepath=Products/The_SmartPill_Capsule&id=17814 (1 page).
Solanas et al., "RFID Technology for the Health Care Sector" Recent Patents on Electrical Engineerins (2008) 1, 22-31.

Soper, S.A. et al. "Bio-Mems Technologies and Applications", Chapter 12, "MEMS for Drug Delivery", p. 325-346 (2007).
Swedberg, "University Team Sees Ingestible RFID Tag as a Boon to Clinical Trials" RFID Journal (2010) Apr. 27; http://www.rfidjournal.com/article/view/7560/1 3pp.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Target Innovations, Tablet Metal Detector, https://web.arch ive.org/web/20 130215063351 /http://www. metaldetectorindia.com/lablet -metal-detector, html, Feb. 15, 2013.
TargetPharmaceutical Metal Detector, Feb. 15, 2013 downloaded from Target Innovations, Tablet Metal Detector, Feb. 15, 2013.
Tatbul et al., "Confidence-based data management for personal area sensor networks" ACM International Conference Proceeding Series (2004) 72; 3 pages.
Tierney, M.J. et al "Electroreleasing Composite Membranes for Delivery of Insulin and other Biomacromolecules" J. Electrochem. Soc., vol. 137, No. 6, Jun. (1990), p. 2005-2006.
Trutag Technologies, Inc., Spectral Microtags for Authentication and Anti-Counterfeiting; "Product Authentication and Brand Protection Solutions"; http://www.trutags.com/; downloaded Feb. 12, 2013; 1 pp.
Walkey, "MOSFET Structure and Processing"; 97.398* Physical Electronics Lecture 20; 24 pp.
Wang, X. et al "Resistance to Tracking and Erosion of Silicone Rubber Material under Various Types of Precipitation", Jpn. J. Appl. Phys. vol. 38 (1999) pp. 5170-5175.
Watson, et al., "Determination of the relationship between the pH and conductivity of gastric juice" Physiol Meas. 17 (1996) pp. 21-27.
Winter, J. et al. "The material properties of gelatin gels"; USA Ballistic Research Laboratories, March (1975), p. 1-157.
Wongmanerod et al., "Determination of pore size distribution and surface area of thin porous silicon layers by spectroscopic ellipsometry" Applied Surface Science 172 (2001) 117-125.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Yao et al. "Low Power Digital Communication in Implantable Devices Using vol. Conduction of Biological Tissues" Proceedings of the 28th IEEE, EMBS Annual International Conference, Aug. 30-Sep. 3 (2006): pp. 6249-6252.
Youtube video Pharmaceutical Metal Detector/Tablet Metal Detector/ Capsule Metal Detector/ Dry Fruits: https://www.youtube.com/watch?v=I0126txam_s, May 12, 2012.
Zimmerman, "Personal Area Networks: Near-field intrabody communication" IBM Systems Journal (1996) 35 (3-4):609-17.
Zworkin, "A Radio Pill" Nature, (1957) 898, 179 Nature Publishing Group.

* cited by examiner

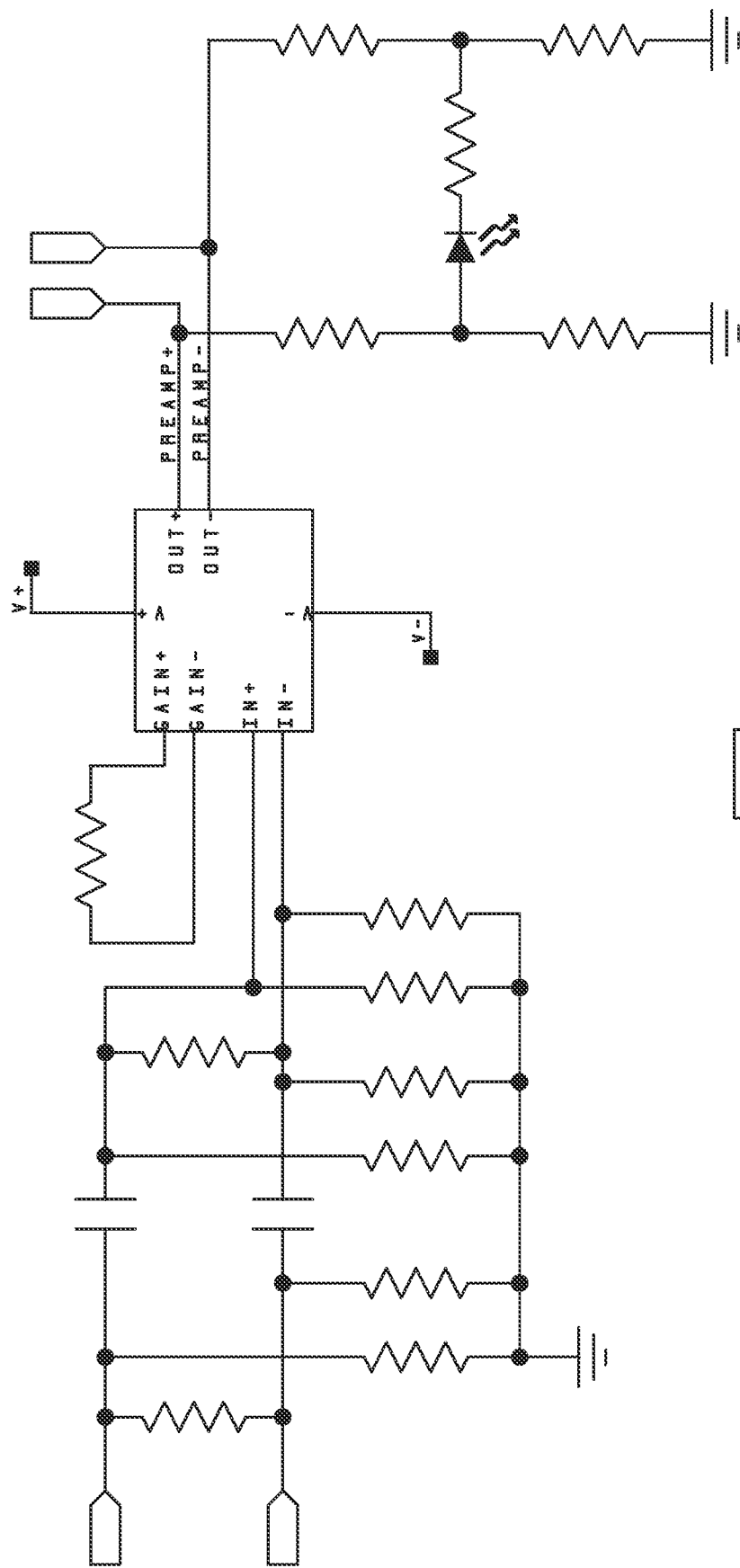
FIG. 18B1

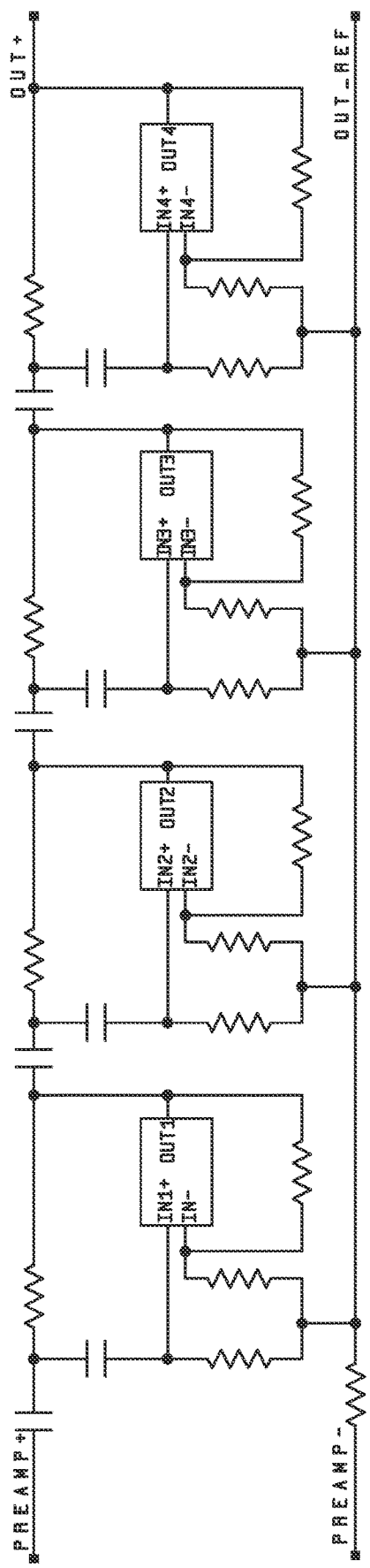
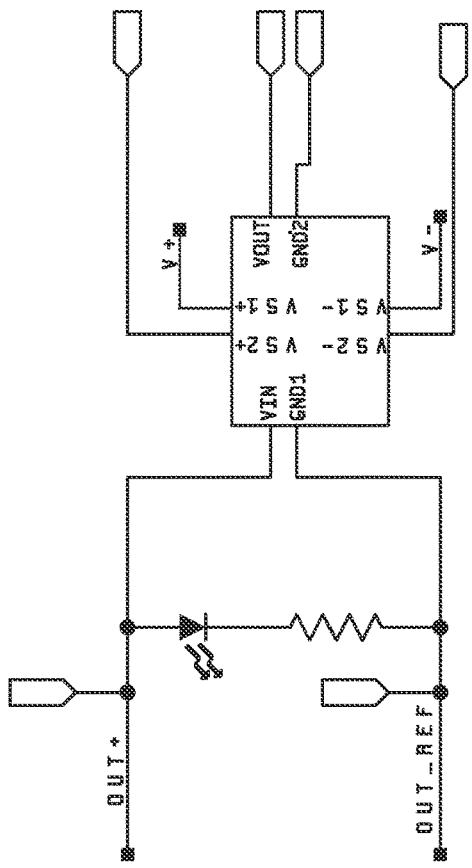
FIG. 18B2

PHARMA-INFORMATICS SYSTEM

CROSS-REFERENCE TO RELATED APPLICATIONS

This application is a continuation of U.S. application Ser. No. 16/793,374, filed on Feb. 18, 2020, which is a continuation of U.S. application Ser. No. 15/788,968, filed on Oct. 20, 2017, now U.S. Pat. No. 10,610,128, which is a continuation of U.S. application Ser. No. 14/699,681, filed on Apr. 29, 2015, which is a continuation of U.S. application Ser. No. 14/596,056, filed on Jan. 13, 2015, now U.S. Pat. No. 9,681,842, which is a continuation of U.S. application Ser. No. 12/949,720, filed on Nov. 18, 2010, now U.S. Pat. No. 9,119,554, which is a continuation of U.S. application Ser. No. 11/912,475, filed on Jun. 23, 2008, now U.S. Pat. No. 8,847,766, which is the U.S. National Stage entry of International Application No. PCT/US2006/016370, filed on Apr. 28, 2006, which, pursuant to 35 U.S.C. § 119(e), claims priority to the filing dates of: U.S. Provisional Patent Application Ser. No. 60/676,145 filed Apr. 28, 2005; U.S. Provisional Patent Application Ser. No. 60/694,078 filed Jun. 24, 2005; U.S. Provisional Patent Application Ser. No. 60/713,680 filed Sep. 1, 2005, and U.S. Provisional Patent Application Ser. No. 60/790,335 filed Apr. 7, 2006 and entitled "Pharma-Informatics System"; the disclosures of which are herein incorporated by reference.

BACKGROUND

The present Invention relates generally to medical apparatus and methods. More specifically, the present invention relates to apparatus and methods for automatic identification of ingestion or other actual, physical administration of a pharmaceutical material.

Prescription medications are effective remedies for many patients when taken properly, e.g., according to instructions. However, studies have shown that, on average, about 50% of patients do not comply with prescribed medication regimens. A low rate of compliance with medication regimens results in a large number of hospitalizations and admissions to nursing homes every year. In the United States alone, it has recently been estimated that the cost to the resulting from patient non-compliance is reaching $100 billion annually.

Consequently, various methods and apparatus have been made available to improve patient compliance with prescribed regimens in efforts to improve patient health. To date, many different types of "smart" packaging devices have been developed. In some cases, such devices automatically dispense the appropriate pill. In other cases, there are electronic controls that detect and record when the pill is taken out of the box.

While devices and protocols have been developed for improving patient compliance, there is continued interest in the development of new ways of monitoring patient compliance.

SUMMARY

The present invention allows, for the first time, the specific identification of pharmaceutical pills and other types of pharmaceutical delivery systems, such as skin diffusion patches, so that the actual, physical delivery of the pharmaceutical into the body can be automatically detected and this information stored. Because the inventive automatic reporting of physical drug administration does not require patient or clinician input, it avoids many of the inaccuracies which introduce uncertainty in current drug administration monitoring systems. These inventive features are particularly critical when a patient's compliance or mental capacity is a consideration, such as in the administration of psychotropic drugs. The present invention also allows for the identification of sources of illicit drugs for law enforcement purposes.

The present invention allows, for the first time, the specific identification of pharmaceutical pills and other types of pharmaceutical delivery systems, such as skin diffusion patches, so that the actual, physical delivery of the pharmaceutical into the body can be automatically detected and this information stored. Because the inventive automatic reporting of physical drug administration does not require patient or clinician input, it avoids many of the inaccuracies which introduce uncertainty in current drug administration monitoring systems. These inventive features are particularly critical when a patient's compliance or mental capacity is a consideration, such as in the administration of psychotropic drugs. The present invention also allows for the identification of sources of illicit drugs for law enforcement purposes.

Embodiments of the invention include compositions having: an active agent; an identifier and a pharmaceutically acceptable carrier. In one embodiment of the present invention, an ingestible pill is made identifiable by providing an electronic microchip as part of the pill structure. In some aspects, the electronic microchip is completely encased within the pill. In this embodiment, the pill broadcasts a signal when it is dissolved in an ionic solution such as stomach fluids. The broadcasted signal is received by another device, e.g., a receiver, either inside or near the body. In turn, the receiver then records that the pill has in fact reached the stomach and is in the process of being dissolved.

In certain of these embodiments, the signal is an oscillating signal which is picked up by an implanted or topically applied receiver. The implant has one or two electrode(s) that sense the varying signal. The implant is configured so that it can identify the code and record that a specific pill has been ingested at a specific time.

BRIEF DESCRIPTION OF THE FIGURES

FIG. 18B1-18B2 provides an exemplary schematic diagram of a receiver circuit, in accordance with one embodiment of the present invention.

DETAILED DESCRIPTION

Figure 1:
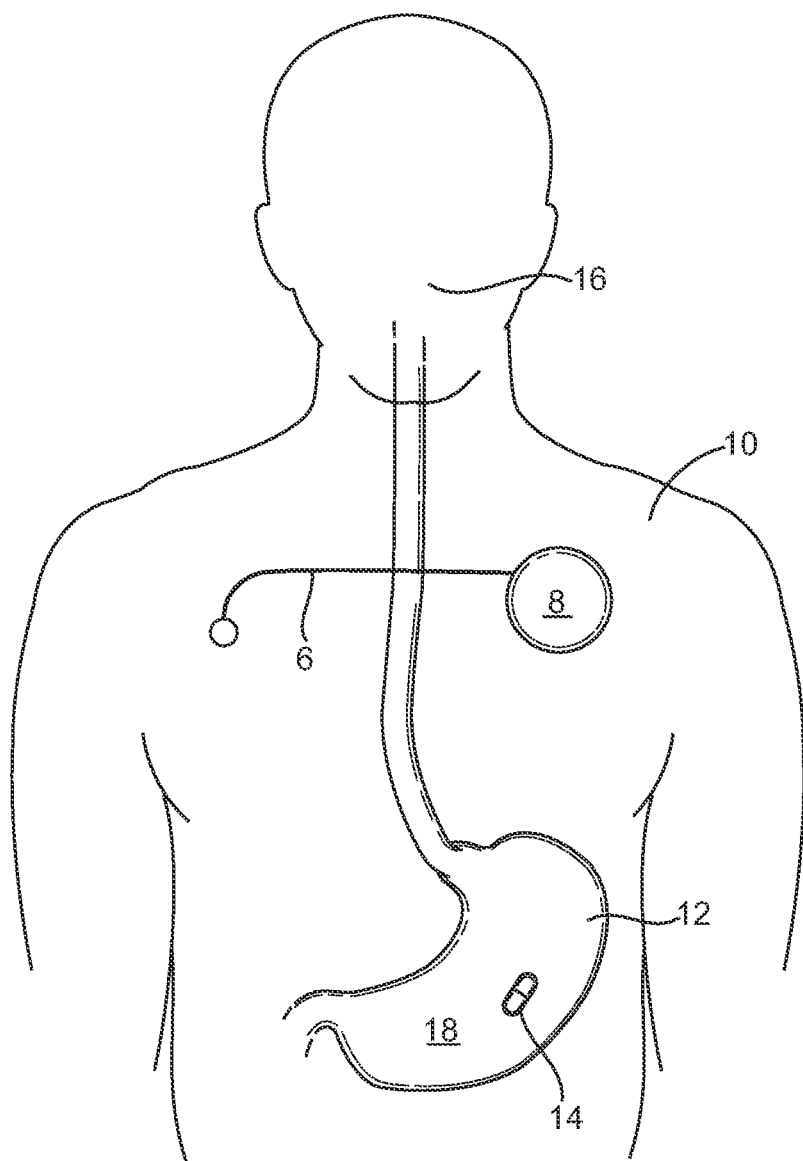
FIG. 1 provides a diagrammatic, exemplary representation of the pill embodiment of the present invention.

The present invention provides the clinician an important new tool in their therapeutic armamentarium: automatic detection and identification of pharmaceutical agents actually delivered into the body. The applications of this new information device and system are multi-fold. By example, when used in concert with other medical sensing devices, correlation between drug delivery, batch and dosage can be correlated to a physiological response. In this manner, optimal pharma-therapeutic regimens may be formulated by the clinician. By example, cardiac stimulating drugs can be titrated to the most appropriate dosages, minimizing side effects such as cardiac muscle exhaustion and rebound effects among others, and optimizing both dosage and timing for each, individual patient.

Assessment of a range of alternate medications is made possible by the present invention without resort to awaiting overt clinical sequel of treatment, many of which can be seriously adverse. By example, positive effects would be quickly ascertainable without being obscured by more random factors. Negative responses, such as changes in blood pressure, would become clearly evident as drug related or independent above background physiologic variation.

The ability to document the ingestion of a drug or other actual exposure of the body to a medication has many important clinical applications. In the simplest form, this technique provides accurate data of when a pill has been taken and which pill has been taken. This allows the precise determination of which pill was taken at a specific point in time. Such monitoring capability assures patients are taking the prescribed medication correctly. This information avoids the potential for over prescription of medications that are not actually being taken. By example, if pain killers are intended to be administered to a patient, it is possible to verify that the patient did in fact take those pain killers in a certain period of time. This is an important tool in limiting the illicit sale of unconsumed drugs to an unintended party. In the case of cardio vascular pills, the clinician or care giver is able to verify that the amount of the drug was taken has been taken at approximately the right point and time. Thus, the true efficacy of the drug can be accurately evaluated. Proper administration and patient compliance is especially critical in Alzheimer's, psychiatric, and alcohol aversion drugs, and in the treatment of rest home residents. In the case of accidental and other overdoses situations, the intervening clinician will be able to discern how far the ingestion has proceeded, and how many pills are involved.

In one clinical arena, the present invention allows, in concert with other sensing device developed by some of the present inventors, the measurement and assessment of the cardiac response to those medications. These co-employed sensing devices can be those enumerated below, among others. Other sensing technology developed by some of the present inventors allows measurement of heart health and cardiac efficiency. Using these tools in concert with the present inventive device, the clinician will be able to compare the response of the heart and body to the administered pharmaceutical.

The data provided by the present invention can optionally be recorded over time. The recording system records synchrony or conduction velocity of a signal going through cardiac tissue and how that is mediated by the presence of a certain medication. This unique data is made possible by the present invention since it can determine electronically exactly when the pill or other medication was being absorbed into the body.

From this innovative data, the present invention provides the clinician an accurate dose response curve showing the response to that medication and the timing of the digestion of the pill. Such innovative data has many applications. For instance, the clinician now has the ability to determine which patients have no response to the medicine in the pill. In a study situation, such patients can be removed from a study or a test of the clinical utility of a certain medication. This provides that only people who have a beneficial response to a certain medication are retained in the trail. This feature will improve the efficacy of medications and to reduce the amount of medications that people take that are not being useful. It may also be used in trials to determine which patients actually consumed the medicine, and which did not.

In more standard clinical environments, this unique data allows careful selection and titration of drug administration without resort to more overt physical symptoms to ascertain contraindications, efficacy, and optimal dosage levels.

The present invention provides a record for emergency room technicians or doctors when a patient is admitted to a hospital so that the patient's status can be accurately ascertained. Dosage events within the last hour or day prior to admission, and the identity of the last medication, will be immediately available.

The clinician obtains this information through simple interrogation of the implanted or portable device. This device would tell them without any uncertainty what pills have been taken. As the inventive technology becomes more wide spread, this data will become more regularly available. The present inventive microchips described below are sufficiently inexpensive when put into standard production that most or all pharmaceuticals will be fitted with them as a matter of course.

In other embodiments of the inventive microchips, the chips can be fitted with coils, susceptible of interrogation without being dissolved in the body. This is accomplished by transmitting RF energy into the coil in such a way that the inquirer will be apprised of the presence and identity of a pill before it is ingested.

In an additional embodiment of the present invention, a "smart box" is provided that can interrogate each pill and ascertain its address. The box can write a distinctive product number or product code so that every single pill ever made is provided with a unique identifier. Fuses, for example, may be selectively destroyed so the addresses may be detected electrically or optically. Particularly in the case of controlled substances, such as a narcotic, this will be important in limiting the illegal used of previously legitimate medicines. The present invention makes it possible to identify precisely who bought such a pill from the authorized pharmacist. This use of the present invention will rein in the number of illicit uses of controlled substances on the market place.

In further describing the invention in greater detail, embodiments of the compositions are reviewed first, followed by a discussion of systems including the subject compositions, methods of using the subject compositions and systems and various illustrative applications in which the compositions and methods find use. Also reviewed in greater detail below are kits that include the subject compositions.

Compositions

Embodiments of the invention include active agent compositions having an identifier stably associated therewith. In certain embodiments, the compositions are disrupted upon administration to a subject. As such, in certain embodiments, the compositions are physically broken, e.g., dissolved, degraded, eroded, etc., following delivery to a body, e.g., via ingestion, injection, etc. The compositions of these embodiments are distinguished from devices that are configured to be ingested and survive transit through the gastrointestinal tract substantially, if not completely, intact. While the compositions of these embodiments are themselves disrupted upon administration, components of the composition, e.g., the identifier, may survive transit of the gastrointestinal tract, e.g., as described in greater detail below.

In certain embodiments, the compositions include an active agent/carrier component and an identifier. Each of these different components is reviewed separately in greater detail below.

Active Agent/Carrier Component

The subject compositions include an active agent/carrier component. By "active agent/carrier component" is meant a composition, which may be a solid or fluid (e.g., liquid), which has an amount of active agent, e.g., a dosage, present in a pharmaceutically acceptable carrier. The active agent/carrier component may be referred to as a "dosage formulation."

Active Agent

"Active agent" includes any compound or mixture of compounds which produces a physiological result, e.g., a beneficial or useful result, upon contact with a living organism, e.g., a mammal, such as a human. Active agents are distinguishable from such components as vehicles, carriers, diluents, lubricants, binders and other formulating aids, and encapsulating or otherwise protective components. The active agent may be any molecule, as well as binding portion or fragment thereof, that is capable of modulating a biological process in a living subject. In certain embodiments, the active agent may be a substance used in the diagnosis, treatment, or prevention of a disease or as a component of a medication. In certain embodiments, the active agent may be a chemical substance, such as a narcotic or hallucinogen, which affects the central nervous system and causes changes in behavior.

The active agent (i.e., drug) is capable of interacting with a target in a living subject. The target may be a number of different types of naturally occurring structures, where targets of interest include both intracellular and extracellular targets. Such targets may be proteins, phospholipids, nucleic acids and the like, where proteins are of particular interest. Specific proteinaceous targets of interest include, without limitation, enzymes, e.g. kinases, phosphatases, reductases, cyclooxygenases, proteases and the like, targets comprising domains involved in protein-protein interactions, such as the SH2, SH3, PTB and PDZ domains, structural proteins, e.g. actin, tubulin, etc., membrane receptors, immunoglobulins, e.g. IgE, cell adhesion receptors, such as integrins, etc., ion channels, transmembrane pumps, transcription factors, signaling proteins, and the like.

The active agent (i.e., drug) may include one or more functional groups necessary for structural interaction with the target, e.g., groups necessary for hydrophobic, hydrophilic, electrostatic or even covalent interactions, depending on the particular drug and its intended target. Where the target is a protein, the drug moiety may include functional groups necessary for structural interaction with proteins, such as hydrogen bonding, hydrophobic-hydrophobic interactions, electrostatic interactions, etc., and may include at least an amine, amide, sulfhydryl, carbonyl, hydroxyl or carboxyl group, such as at least two of the functional chemical groups.

Drugs of interest may include cyclical carbon or heterocyclic structures and/or aromatic or polyaromatic structures substituted with one or more of the above functional groups. Also of interest as drug moieties are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The drugs may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As such, the drug may be obtained from a library of naturally occurring or synthetic molecules, including a library of compounds produced through combinatorial means, i.e., a compound diversity combinatorial library. When obtained from such libraries, the drug moiety employed will have demonstrated some desirable activity in an appropriate screening assay for the activity. Combinatorial libraries, as well as methods for producing and screening such libraries, are known in the art and described in: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Broad categories of active agents of interest include, but are not limited to: cardiovascular agents; pain-relief agents, e.g., analgesics, anesthetics, anti-inflammatory agents, etc.; nerve-acting agents; chemotherapeutic (e.g., anti-neoplastic) agents; etc.

In certain embodiments, the active agent is a cardiovascular agent, i.e., an agent employed in the treatment of cardiovascular or heart conditions. In certain embodiments, the active agent is a cardiovascular agent, i.e., an agent employed in the treatment of cardiovascular or heart conditions. Cardiovascular agents of interest include, but are not limited to: cardioprotective agents, e.g., Zinecard (dexrazoxane); blood modifiers, including anticoagulants (e.g., coumadin (warfarin sodium), fragmin (dalteparin sodium), heparin, innohep (tinzaparin sodium), lovenox (enoxaparin sodium), orgaran (danaparoid sodium)) antiplatelet agents (e.g., aggrasta (tirofiban hydrochloride), aggrenox (aspirin/extended release dipyridamole), agrylin (anagrelide hydrochloride), ecotrin (acetylsalicylic acid), folan (epoprostenol sodium), halfprin (enteric coated aspirin), integrlilin (eptifibatide), persantine (dipyridamole USP), plavix (clopidogrel bisulfate), pletal (cilostazol), reopro (abciximab), ticlid (ticlopidine hydrochloride)), thrombolytic agents (activase (alteplase), retavase (reteplase), streptase (streptokinase)); adrenergic blockers, such as cardura (doxazosin mesylate), dibenzyline (phenoxybenzamine hydrochloride), hytrin (terazosin hydrochloride), minipress (prazosin hydrochloride), minizide (prazosin hydrochloride/polythiazide); adrenergic stimulants, such as aldoclor (methyldopa—chlorothiazide), aldomet (methyldopa, methyldopate HCl), aldoril (methyldopa—hydrochlorothiazide), catapres (clonidine hydrochloride USP, clonidine), clorpres (clonidine hydrochloride and chlorthalidone), combipres (clonidine hydrochloride/chlorthalidone), tenex (guanfacine hydrochloride); alpha/bet adrenergic blockers, such as coreg (carvedilol), normodyne (labetalol hydrochloride); angiotensin converting enzyme (ACE) inhibitors, such as accupril (quinapril hydrochloride), aceon (perindopril erbumine), altace (ramipril), captopril, lotensin (benazepril hydrochloride), mavik (trandolapril), monopril (fosinopril sodium tablets), prinivil (lisinopril), univasc (moexipril hydrochloride), vasotec (enalaprilat, enalapril maleate), zestril (lisinopril); angiotensin converting enzyme (ACE) inhibitors with calcium channel blockers, such as lexxel (enalapril maleate—felodipine ER), lotrel (amlodipine and benazepril hydrochloride), tarka (trandolapril/verapamil hydrochloride ER); angiotensin converting enzyme (ACE) inhibitors with diuretics, such as accuretic (quinapril HCl/hydroclorothiazide), lotensin (benazepril hydrochloride and hydrochlorothiazide USP), prinizide (lisinopril-hydrochlorothiazide), uniretic (moexipril hydrochloride/hydrochlorothiazide), vaseretic (enalapril maleate—hydrochlorothiazide), zestoretic (lisinopril and hydrochlorothiazide); angiotensin II receptor antagonists, such as atacand (candesartan cilexetil), avapro (irbesartan), cozaar (losartan potassium), diovan (valsartan), micardis (telmisartan), teveten (eprosartan mesylate); angiotensin II receptor antagonists with diuretics, such as avalide (irbesartan—hydrochlorothiazide), diovan (valsartan and hydrochlorothiazide), hyzaar (losartan potassium—hydrochlorothiazide); antiarrhythmics, such as Group I (e.g., mexitil (mexiletine hydrochloride, USP), norpace (disopyramide phosphate), procanbid (procainamide hydrochloride), quinaglute (quinidine gluconate), quinidex (quinidine sulfate), quinidine (quinidine gluconate injection, USP), rythmol (propafenone hydrochloride), tambocor (flecainide acetate), tonocard (tocainide HCl)), Group II (e.g., betapace (sotalol HCl), brevibloc (esmolol hydrochloride), inderal (propranolol hydrochloride), sectral (acebutolol hydrochloride)), Group III (e.g., betapace (sotalol HCl), cordarone (amiodarone hydrochloride), corvert (ibutilide fumarate injection), pacerone (amiodarone HCl), tikosyn (dofetilide)), Group IV (e.g., calan (verapamil hydrochloride), cardizem (diltiazem HCl), as well as adenocard (adenosine), lanoxicaps (digoxin), lanoxin (digoxin)); antilipemic acids, including bile acid sequestrants (e.g., colestid (micronized colestipol hydrochloride), welchol (colesevelam hydrochloride)), fibric acid derivatives (e.g., atromid (clofibrate), lopid (gemfibrozal tablets, USP), tricor (fenofibrate capsules)), HMG-CoA reductase inhibitors (e.g., baycol (cerivastatin sodium tablets), lescol (fluvastatin sodium), lipitor (atorvastatin calcium), mevacor (lovastatin), pravachol (pravastatin sodium), zocor (simvastatin)), Nicotinic Acid (e.g., Niaspan (niacin extended release tablets)); beta adrenergic blocking agents, e.g., betapace (sotalol HCl), blocadren (timolol maleate), brevibloc (esmolol hydrochloride), cartrol (carteolol hydrochloride), inderal (propranolol hydrochloride), kerlone (betaxolol hydrochloride), nadolol, sectral (acebutolol hydrochloride), tenormin (atenolol), toprol (metoprolol succinate), zebeta (bisoprolol fumarate); beta adrenergic blocking agents with diuretics, e.g., corzide (nadolol and bendroflumethiazide tablets), inderide (propranolol hydrochloride and hydroclorothiazide), tenoretic (atenolol and chlorthalidone), timolide (timolol maleate—hydrochlorothiazide), ziac (bisoprolol fumarate and hydrochloro-thiazide); calcium channel blockers, e.g., adalat (nifedipine), calan (verapamil hydrochloride), cardene (nicardipine hydrochloride), cardizem (diltiazem HCl), covera (verapamil hydrochloride), isoptin (verapamil hydrochloride), nimotop (nimodipine), norvasc (amlodipine besylate), plendil (felodipine), procardia (nifedipine), sular (nisoldipine), tiazac (diltiazem hydrochloride), vascor (bepridil hydrochloride), verelan (verapamil hydrochloride); diuretics, including carbonic anhydrase inhibitors (e.g., daranide (dichlorphenamide)), combination diuretics (e.g., aldactazide (spironolactone with hydrochlorothiazide), dyazide (triamterene and hydrochlorothiazide), maxzide (triamterene and hydrochlorothiazide), moduretic (amiloride HCl—hydrochlorothiazide)), loop diuretics (demadex (torsemide), edecrin (ethacrynic acid, ethacrynate sodium), furosemide), potassium-sparing diuretics (aldactone (spironolactone), dyrenium (triamterene), midamor (amiloride HCl)), thiazides & related diuretics (e.g., diucardin (hydroflumethiazide), diuril (chlorothiazide, chlorothiazide sodium), enduron (methyclothiazide), hydrodiuril hydrochlorothiazide), indapamide, microzide (hydrochlorothiazide) mykrox (metolazone tablets), renese (polythi-azide), thalitone (chlorthalidone, USP), zaroxolyn (metolazone)); inotropic agents, e.g., digitek (digoxin), dobutrex (dobutamine), lanoxicaps (digoxin), lanoxin (digoxin), primacor (milrinone lactate); activase (alteplase recombinant); adrenaline chloride (epinephrine injection, USP); demser (metyrosine), inversine (mecamylamine HCl), reopro (abciximab), retavase (reteplase), streptase (streptokinase), tnkase (tenecteplase); vasodilators, including coronary vasodilators (e.g., imdur (isosorbide mononitrate), ismo (isosorbide mononitrate), isordil (isosorbide dinitrate), nitrodur (nitroglycerin), nitrolingual (nitroglycerin lingual spray), nitrostat (nitroglycerin tablets, USP), sorbitrate (isosorbide dinitrate)), peripheral vasodilators & combinations (e.g., corlopam (fenoldopam mesylate), fiolan (epoprostenol sodium), primacor (milrinone lactate)), vasopressors, e.g., aramine (metaraminol bitartrate), epipen (EpiPen 0.3 mg brand of epinephrine auto injector, EpiPen Jr. 0.15 mg brand of epinephrine auto injector), proamatine (midodrine hydrochloride); etc.

In certain embodiments, specific drugs of interest include, but are not limited to: psychopharmacological agents, such as (1) central nervous system depressants, e.g. general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines, etc.), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs, etc.), analgesics (morphine and derivatives, oripavine derivatives, morphinan derivatives, phenylpiperidines, 2,6-methane-3-benzazocaine derivatives, diphenylpropylamines and isosteres, salicylates, p-aminophenol derivatives, 5-pyrazolone derivatives, arylacetic acid derivatives, fenamates and isosteres, etc.) and antiemetics (anticholinergics, antihistamines, antidopaminergics, etc.), (2) central nervous system stimulants, e.g. analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics, (3) psychopharmacologicals, e.g. anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives, etc.), antidepressants (tricyclic compounds, MAO inhibitors, etc.), (4) respiratory tract drugs, e.g. central antitussives (opium alkaloids and their derivatives);

pharmacodynamic agents, such as (1) peripheral nervous system drugs, e.g. local anesthetics (ester derivatives, amide derivatives), (2) drugs acting at synaptic or neuroeffector junctional sites, e.g. cholinergic agents, cholinergic blocking agents, neuromuscular blocking agents, adrenergic agents, antiadrenergic agents, (3) smooth muscle active drugs, e.g. spasmolytics (anticholinergics, musculotropic spasmolytics), vasodilators, smooth muscle stimulants, (4) histamines and antihistamines, e.g. histamine and derivative thereof (betazole), antihistamines (H1-antagonists, H2-antagonists), histamine metabolism drugs, (5) cardiovascular drugs, e.g. cardiotonics (plant extracts, butenolides, pentadienolids, alkaloids from erythrophleum species, ionophores,—adrenoceptor stimulants, etc), antiarrhythmic drugs, antihypertensive agents, antilipidemic agents (clofibric acid derivatives, nicotinic acid derivatives, hormones and analogs, antibiotics, salicylic acid and derivatives), antivaricose drugs, hemostyptics, (6) blood and hemopoietic system drugs, e.g. antianemia drugs, blood coagulation drugs (hemostatics, anticoagulants, antithrombotics, thrombolytics, blood proteins and their fractions), (7) gastrointestinal tract drugs, e.g. digestants (stomachics, choleretics), antiulcer drugs, antidiarrheal agents, (8) locally acting drugs;

chemotherapeutic agents, such as (1) anti-infective agents, e.g. ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, etc., and (2) cytostatics, i.e. antineoplastic agents or cytotoxic drugs, such as alkylating agents, e.g. Mechlorethamine hydrochloride (Nitrogen Mustard, Mustargen, HN2), Cyclophosphamide (Cytovan, Endoxana), Ifosfamide (IFEX), Chlorambucil (Leukeran), Melphalan (Phenylalanine Mustard, L-sarcolysin, Alkeran, L-PAM), Busulfan (Myleran), Thiotepa (Triethylenethiophosphoramide), Carmustine (BiCNU, BCNU), Lomustine (CeeNU, CCNU), Streptozocin (Zanosar) and the like; plant alkaloids, e.g. Vincristine (Oncovin), Vinblastine (Velban, Velbe), Paclitaxel (Taxol), and the like; antimetabolites, e.g. Methotrexate (MTX), Mercaptopurine (Purinethol, 6-MP), Thioguanine (6-TG), Fluorouracil (5-FU), Cytarabine (Cytosar-U, Ara-C), Azacitidine (Mylosar, 5-AZA) and the like; antibiotics, e.g. Dactinomycin (Actinomycin D, Cosmegen), Doxorubicin (Adriamycin), Daunorubicin (duanomycin, Cerubidine), Idarubicin (Idamycin), Bleomycin (Blenoxane), Picamycin (Mithramycin, Mithracin), Mitomycin (Mutamycin) and the like, and other anticellular proliferative agents, e.g. Hydroxyurea (Hydrea), Procarbazine (Mutalane), Dacarbazine (DTIC-Dome), Cisplatin (Platinol) Carboplatin (Paraplatin), Asparaginase (Elspar) Etoposide (VePesid, VP-16-213), Amsarcrine (AMSA, m-AMSA), Mitotane (Lysodren), Mitoxantrone (Novatrone), and the like;

antibiotics, such as: aminoglycosides, e.g. amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g. azidamfenicol, chloramphenicol, florfenicol, and theimaphenicol; ansamycins, e.g. rifamide, rifampin, rifamycin, rifapentine, rifaximin; b-lactams, e.g. carbacephems, carbapenems, cephalosporins, cehpamycins, monobactams, oxaphems, penicillins; lincosamides, e.g. clinamycin, lincomycin; macrolides, e.g. clarithromycin, dirthromycin, erythromycin, etc.; polypeptides, e.g. amphomycin, bacitracin, capreomycin, etc.; tetracyclines, e.g. apicycline, chlortetracycline, clomocycline, etc.; synthetic antibacterial agents, such as 2,4-diaminopyrimidines, nitrofurans, quinolones and analogs thereof, sulfonamides, sulfones;

antifungal agents, such as: polyenes, e.g. amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g. butenafine, naftifine, terbinafine; imidazoles, e.g. bifonazole, butoconazole, chlordantoin, chlormidazole, etc., thiocarbamates, e.g. tolciclate, triazoles, e.g. fluconazole, itraconazole, terconazole;

anthelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, diethylcarbamazine, etc.;

antimalarials, such as: acedapsone, amodiaquin, arteether, artemether, artemisinin, artesunate, atovaquone, bebeerine, berberine, chirata, chlorguanide, chloroquine, chlorproguanil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinidine, quinine, quinocide, quinoline, dibasic sodium arsenate;

antiprotozoan agents, such as: acranil, tinidazole, ipronidazole, ethylstibamine, pentamidine, acetarsone, aminitrozole, anisomycin, nifuratel, tinidazole, benzidazole, suramin, and the like.

Name brand drugs of interest include, but are not limited to: RezulinÔ, Lovastatin™, Enalapril™, Prozac™, Prilosec™, Lipotor™, Claritin™, Zocor™, Ciprofloxacin™, Viagra™, Crixivan™, Ritalin™, and the like.

Drug compounds of interest are also listed in: Goodman & Gilman's, The Pharmacological Basis of Therapeutics (9th Ed) (Goodman et al. eds) (McGraw-Hill) (1996); and 2001 Physician's Desk Reference.

Specific compounds of interest also include, but are not limited to:

Antineoplastic agents, as disclosed in U.S. Pat. Nos. 5,880,161, 5,877,206, 5,786,344, 5,760,041, 5,753,668, 5,698,529, 5,684,004, 5,665,715, 5,654,484, 5,624,924, 5,618,813, 5,610,292, 5,597,831, 5,530,026, 5,525,633, 5,525,606, 5,512,678, 5,508,277, 5,463,181, 5,409,893, 5,358,952, 5,318,965, 5,223,503, 5,214,068, 5,196,424, 5,109,024, 5,106,960, 5,101,072, 5,077,404, 5,071,848, 5,066,493, 5,019,390, 4,996,229, 4,996,206, 4,970,318, 4,968,800, 4,962,114, 4,927,828, 4,892,887, 4,889,859, 4,886,790, 4,882,334, 4,882,333, 4,871,746, 4,863,955, 4,849,563, 4,845,216, 4,833,145, 4,824,955, 4,785,085, 476, 925, 4,684,747, 4,618,685, 4,611,066, 4,550,187, 4,550,186, 4,544,501, 4,541,956, 4,532,327, 4,490,540, 4,399,283, 4,391,982, 4,383,994, 4,294,763, 4,283,394, 4,246,411, 4,214,089, 4,150,231, 4,147,798, 4,056,673, 4,029,661, 4,012,448;

psychopharmacological/psychotropic agents, as disclosed in U.S. Pat. Nos. 5,192,799, 5,036,070, 4,778,800, 4,753, 951, 4,590,180, 4,690,930, 4,645,773, 4,427,694, 4,424,202, 4,440,781, 5,686,482, 5,478,828, 5,461,062, 5,387,593, 5,387,586, 5,256,664, 5,192,799, 5,120,733, 5,036,070, 4,977,167, 4,904,663, 4,788,188, 4,778,800, 4,753,951, 4,690,930, 4,645,773, 4,631,285, 4,617,314, 4,613,600, 4,590,180, 4,560,684, 4,548,938, 4,529,727, 4,459,306, 4,443,451, 4,440,781, 4,427,694, 4,424,202, 4,397,853, 4,358,451, 4,324,787, 4,314,081, 4,313,896, 4,294,828, 4,277,476, 4,267,328, 4,264,499, 4,231,930, 4,194,009, 4,188,388, 4,148,796, 4,128,717, 4,062,858, 4,031,226, 4,020,072, 4,018,895, 4,018,779, 4,013,672, 3,994,898, 3,968,125, 3,939,152, 3,928,356, 3,880,834, 3,668,210;

cardiovascular agents, as disclosed in U.S. Pat. Nos. 4,966,967, 5,661,129, 5,552,411, 5,332,737, 5,389,675, 5,198,449, 5,079,247, 4,966,967, 4,874,760, 4,954,526, 5,051,423, 4,888,335, 4,853,391, 4,906,634, 4,775,757, 4,727,072, 4,542,160, 4,522,949, 4,524,151, 4,525,479, 4,474,804, 4,520,026, 4,520,026, 5,869,478, 5,859,239, 5,837,702, 5,807,889, 5,731,322, 5,726,171, 5,723,457, 5,705,523, 5,696,111, 5,691,332, 5,679,672, 5,661,129, 5,654,294, 5,646,276, 5,637,586, 5,631,251, 5,612,370, 5,612,323, 5,574,037, 5,563,170, 5,552,411, 5,552,397, 5,547,966, 5,482,925, 5,457,118, 5,414,017, 5,414,013, 5,401,758, 5,393,771, 5,362,902, 5,332,737, 5,310,731, 5,260,444, 5,223,516, 5,217,958, 5,208,245, 5,202,330, 5,198,449, 5,189,036, 5,185,362, 5,140,031, 5,128,349, 5,116,861, 5,079,247, 5,070,099, 5,061,813, 5,055,466, 5,051,423, 5,036,065, 5,026,712, 5,011,931, 5,006,542, 4,981,843, 4,977,144, 4,971,984, 4,966,967, 4,959,383, 4,954,526, 4,952,692, 4,939,137, 4,906,634, 4,889,866, 4,888,335, 4,883,872, 4,883,811, 4,847,379, 4,835,157, 4,824,831, 4,780,538, 4,775,757, 4,774,239, 4,771,047, 4,769,371, 4,767,756, 4,762,837, 4,753,946, 4,752,616, 4,749,715, 4,738,978, 4,735,962, 4,734,426, 4,734,425, 4,734,424, 4,730,052, 4,727,072, 4,721,796, 4,707,550, 4,704,382, 4,703,120, 4,681,970, 4,681,882, 4,670,560, 4,670,453, 4,668,787, 4,663,337, 4,663,336, 4,661,506, 4,656,267, 4,656,185, 4,654,357, 4,654,356, 4,654,355, 4,654,335, 4,652,578, 4,652,576, 4,650,874, 4,650,797, 4,649,139, 4,647,585, 4,647,573, 4,647,565, 4,647,561, 4,645,836, 4,639,461, 4,638,012, 4,638,011, 4,632,931, 4,631,283, 4,628,095, 4,626,548, 4,614,825, 4,611,007, 4,611,006, 4,611,005, 4,609,671, 4,608,386, 4,607,049, 4,607,048, 4,595,692, 4,593,042, 4,593,029, 4,591,603, 4,588,743, 4,588,742, 4,588,741, 4,582,854, 4,575,512, 4,568,762, 4,560,698, 4,556,739, 4,556,675, 4,555,571, 4,555,570, 4,555,523, 4,550,120, 4,542,160, 4,542,157, 4,542,156, 4,542,155, 4,542,151, 4,537,981, 4,537,904, 4,536,514, 4,536,513, 4,533,673, 4,526,901, 4,526,900, 4,525,479, 4,524,151, 4,522,949, 4,521,539, 4,520,026, 4,517,188, 4,482,562, 4,474,804, 4,474,803, 4,472,411, 4,466,979, 4,463,015, 4,456,617, 4,456,616, 4,456,615, 4,418,076, 4,416,896, 4,252,815, 4,220,594, 4,190,587, 4,177,280, 4,164,586, 4,151,297, 4,145,443, 4,143,054, 4,123,550, 4,083,968, 4,076,834, 4,064,259, 4,064,258, 4,064,257, 4,058,620, 4,001,421, 3,993,639, 3,991,057, 3,982,010, 3,980,652, 3,968,117, 3,959,296, 3,951,950, 3,933,834, 3,925,369, 3,923,818, 3,898,210, 3,897,442, 3,897,441, 3,886,157, 3,883,540, 3,873,715, 3,867,383, 3,873,715, 3,867,383, 3,691,216, 3,624,126;

antimicrobial agents as disclosed in U.S. Pat. Nos. 5,902, 594, 5,874,476, 5,874,436, 5,859,027, 5,856,320, 5,854,242, 5,811,091, 5,786,350, 5,783,177, 5,773,469, 5,762,919, 5,753,715, 5,741,526, 5,709,870, 5,707,990, 5,696,117, 5,684,042, 5,683,709, 5,656,591, 5,643,971, 5,643,950, 5,610,196, 5,608,056, 5,604,262, 5,595,742, 5,576,341, 5,554,373, 5,541,233, 5,534,546, 5,534,508, 5,514,715, 5,508,417, 5,464,832, 5,428,073, 5,428,016, 5,424,396, 5,399,553, 5,391,544, 5,385,902, 5,359,066, 5,356,803, 5,354,862, 5,346,913, 5,302,592, 5,288,693, 5,266,567, 5,254,685, 5,252,745, 5,209,930, 5,196,441, 5,190,961, 5,175,160, 5,157,051, 5,096,700, 5,093,342, 5,089,251, 5,073,570, 5,061,702, 5,037,809, 5,036,077, 5,010,109, 4,970,226, 4,916,156, 4,888,434, 4,870,093, 4,855,318, 4,784,991, 4,479,953, 4,260,634, 4,055,655, 3,915,889, 4,746,504, 4,686,221, 4,599,228, 4,552,882, 4,492,700, 4,489,098, 4,489,085, 4,487,776, 4,477,448, 4,474,807, 4,470,994, 4,370,484, 4,337,199, 4,311,709, 4,308,283, 4,304,910, 4,233,311, 4,215,131, 4,166,122, 4,141,981, 4,130,664, 4,089,977, 4,089,900, 4,069,341, 4,049,665, 4,044,139, 4,002,775, 3,991,201, 3,966,968, 3,954,868, 3,936,393, 3,917,476, 3,867,548, 3,865,748, 3,867,548, 3,865,748, 3,783,160, 3,764,676, 3,764,677;

anti-inflammatory agents as disclosed in U.S. Pat. Nos. 5,872,109, 5,837,735, 5,827,837, 5,821,250, 5,814,648, 5,780,026, 5,776,946, 5,760,002, 5,750,543, 5,741,798, 5,739,279, 5,733,939, 5,723,481, 5,716,967, 5,688,949, 5,686,488, 5,686,471, 5,686,434, 5,684,204, 5,684,041, 5,684,031, 5,684,002, 5,677,318, 5,674,891, 5,672,620 5,665,752, 5,656,661, 5,635,516, 5,631,283, 5,622,948, 5,618,835, 5,607,959, 5,593,980, 5,593,960, 5,580,888, 5,552,424, 5,552,422 5,516,764, 5,510,361, 5,508,026, 5,500,417, 5,498,405, 5,494,927: 5,476,876 5,472,973 5,470,885, 5,470,842, 5,464,856, 5,464,849 5,462,952, 5,459,151, 5,451,686, 5,444,043 5,436,265, 5,432,181, RE034,918, 5,393,756, 5,380,738, 5,376,670, 5,360,811, 5,354,768, 5,348,957, 5,347,029, 5,340,815, 5,338,753, 5,324,648, 5,319,099, 5,318,971, 5,312,821, 5,302,597, 5,298,633, 5,298,522, 5,298,498, 5,290,800, 5,290,788, 5,284,949, 5,280,045, 5,270,319, 5,266,562, 5,256,680, 5,250,700, 5,250,552, 5,248,682, 5,244,917, 5,240,929, 5,234,939, 5,234,937, 5,232,939, 5,225,571, 5,225,418, 5,220,025, 5,212,189, 5,212,172, 5,208,250, 5,204,365, 5,202,350, 5,196,431, 5,191,084, 5,187,175, 5,185,326, 5,183,906, 5,177,079, 5,171,864, 5,169,963, 5,155,122, 5,143,929, 5,143,928, 5,143,927, 5,124,455, 5,124,347, 5,114,958, 5,112,846, 5,104,656, 5,098,613, 5,095,037, 5,095,019, 5,086,064, 5,081,261, 5,081,147, 5,081,126, 5,075,330, 5,066,668, 5,059,602, 5,043,457, 5,037,835, 5,037,811, 5,036,088, 5,013,850, 5,013,751, 5,013,736, 500,654, 4,992,448, 4,992,447, 4,988,733, 4,988,728, 4,981,865, 4,962,119, 4,959,378, 4,954,519, 4,945,099, 4,942,236, 4,931,457, 4,927,835, 4,912,248, 4,910,192, 4,904,786, 4,904,685, 4,904,674, 4,904,671, 4,897,397, 4,895,953, 4,891,370, 4,870,210, 4,859,686, 4,857,644, 4,853,392, 4,851,412, 4,847,303, 4,847,290, 4,845,242, 4,835,166, 4,826,990, 4,803,216, 4,801,598, 4,791,129, 4,788,205, 4,778,818, 4,775,679, 4,772,703, 4,767,776, 4,764,525, 4,760,051, 4,748,153, 4,725,616, 4,721,712, 4,713,393, 4,708,966, 4,695,571, 4,686,235, 4,686,224, 4,680,298, 4,678,802, 4,652,564, 4,644,005, 4,632,923, 4,629,793, 4,614,741, 4,599,360, 4,596,828, 4,595,694, 4,595,686, 4,594,357, 4,585,755, 4,579,866, 4,578,390, 4,569,942, 4,567,201, 4,563,476, 4,559,348, 4,558,067, 4,556,672, 4,556,669, 4,539,326, 4,537,903, 4,536,503, 4,518,608, 4,514,415, 4,512,990, 4,501,755, 4,495,197, 4,493,839, 4,465,687, 4,440,779, 4,440,763, 4,435,420, 4,412,995, 4,400,534, 4,355,034, 4,335,141, 4,322,420, 4,275,064, 4,244,963, 4,235,908, 4,234,593, 4,226,887, 4,201,778, 4,181,720, 4,173,650, 4,173,634, 4,145,444, 4,128,664, 4,125,612, 4,124,726, 4,124,707, 4,117,135, 4,027,031, 4,024,284, 4,021,553, 4,021,550, 4,018,923, 4,012,527, 4,011,326, 3,998,970, 3,998,954, 3,993,763, 3,991,212, 3,984,405, 3,978,227, 3,978,219, 3,978,202, 3,975,543, 3,968,224, 3,959,368, 3,949,082, 3,949,081, 3,947,475, 3,936,450, 3,934,018, 3,930,005, 3,857,955, 3,856,962, 3,821,377, 3,821,401, 3,789,121, 3,789,123, 3,726,978, 3,694,471, 3,691,214, 3,678,169, 3,624,216;

immunosuppressive agents, as disclosed in U.S. Pat. Nos. 4,450,159, 4,450,159, 5,905,085, 5,883,119, 5,880,280, 5,877,184, 5,874,594, 5,843,452, 5,817,672, 5,817,661, 5,817,660, 5,801,193, 5,776,974, 5,763,478, 5,739,169, 5,723,466, 5,719,176, 5,696,156, 5,695,753, 5,693,648, 5,693,645, 5,691,346, 5,686,469, 5,686,424, 5,679,705, 5,679,640, 5,670,504, 5,665,774, 5,665,772, 5,648,376, 5,639,455, 5,633,277, 5,624,930, 5,622,970, 5,605,903, 5,604,229, 5,574,041, 5,565,560, 5,550,233, 5,545,734, 5,540,931, 5,532,248, 5,527,820, 5,516,797, 5,514,688, 5,512,687, 5,506,233, 5,506,228, 5,494,895, 5,484,788, 5,470,857, 5,464,615, 5,432,183, 5,431,896, 5,385,918, 5,349,061, 5,344,925, 5,330,993, 5,308,837, 5,290,783, 5,290,772, 5,284,877, 5,284,840, 5,273,979, 5,262,533, 5,260,300, 5,252,732, 5,250,678, 5,247,076, 5,244,896, 5,238,689, 5,219,884, 5,208,241, 5,208,228, 5,202,332, 5,192,773, 5,189,042, 5,169,851, 5,162,334, 5,151,413, 5,149,701, 5,147,877, 5,143,918, 5,138,051, 5,093,338, 5,091,389, 5,068,323, 5,068,247, 5,064,835, 5,061,728, 5,055,290, 4,981,792, 4,810,692, 4,410,696, 4,346,096, 4,342,769, 4,317,825, 4,256,766, 4,180,588, 4,000,275, 3,759,921;

analgesic agents, as disclosed in U.S. Pat. Nos. 5,292,736, 5,688,825, 5,554,789, 5,455,230, 5,292,736, 5,298,522, 5,216,165, 5,438,064, 5,204,365, 5,017,578, 4,906,655, 4,906,655, 4,994,450, 4,749,792, 4,980,365, 4,794,110, 4,670,541, 4,737,493, 4,622,326, 4,536,512, 4,719,231, 4,533,671, 4,552,866, 4,539,312, 4,569,942, 4,681,879, 4,511,724, 4,556,672, 4,721,712, 4,474,806, 4,595,686, 4,440,779, 4,434,175, 4,608,374, 4,395,402, 4,400,534, 4,374,139, 4,361,583, 4,252,816, 4,251,530, 5,874,459, 5,688,825, 5,554,789, 5,455,230, 5,438,064, 5,298,522, 5,216,165, 5,204,365, 5,030,639, 5,017,578, 5,008,264, 4,994,450, 4,980,365, 4,906,655, 4,847,290, 4,844,907, 4,794,110, 4,791,129, 4,774,256, 4,749,792, 4,737,493, 4,721,712, 4,719,231, 4,681,879, 4,670,541, 4,667,039, 4,658,037, 4,634,708, 4,623,648, 4,622,326, 4,608,374, 4,595,686, 4,594,188, 4,569,942, 4,556,672, 4,552,866, 4,539,312, 4,536,512, 4,533,671, 4,511,724, 4,440,779, 4,434,175, 4,400,534, 4,395,402, 4,391,827, 4,374,139, 4,361,583, 4,322,420, 4,306,097, 4,252,816, 4,251,530, 4,244,955, 4,232,018, 4,209,520, 4,164,514 4,147,872, 4,133,819, 4,124,713, 4,117,012, 4,064,272, 4,022,836, 3,966,944;

cholinergic agents, as disclosed in U.S. Pat. Nos. 5,219,872, 5,219,873, 5,073,560, 5,073,560, 5,346,911, 5,424,301, 5,073,560, 5,219,872, 4,900,748, 4,786,648, 4,798,841, 4,782,071, 4,710,508, 5,482,938, 5,464,842, 5,378,723, 5,346,911, 5,318,978, 5,219,873, 5,219,872, 5,084,281, 5,073,560, 5,002,955, 4,988,710, 4,900,748, 4,798,841, 4,786,648, 4,782,071, 4,745,123, 4,710,508;

adrenergic agents, as disclosed in U.S. Pat. Nos. 5,091,528, 5,091,528, 4,835,157, 5,708,015, 5,594,027, 5,580,892, 5,576,332, 5,510,376, 5,482,961, 5,334,601, 5,202,347, 5,135,926, 5,116,867, 5,091,528, 5,017,618, 4,835,157, 4,829,086, 4,579,867, 4,568,679, 4,469,690, 4,395,559, 4,381,309, 4,363,808, 4,343,800, 4,329,289, 4,314,943, 4,311,708, 4,304,721, 4,296,117, 4,285,873, 4,281,189, 4,278,608, 4,247,710, 4,145,550, 4,145,425, 4,139,535, 4,082,843, 4,011,321, 4,001,421, 3,982,010, 3,940,407, 3,852,468, 3,832,470;

antihistamine agents, as disclosed in U.S. Pat. Nos. 5,874,479, 5,863,938, 5,856,364, 5,770,612, 5,702,688, 5,674,912, 5,663,208, 5,658,957, 5,652,274, 5,648,380, 5,646,190, 5,641,814, 3,946,022, 5,633,285, 5,614,561, 5,602,183, 4,923,892, 4,782,058, 4,393,210, 4,180,583, 3,965,257, 3,931,197;

steroidal agents, as disclosed in U.S. Pat. Nos. 5,863,538, 5,855,907, 5,855,866, 5,780,592, 5,776,427, 5,651,987, 5,346,887, 5,256,408, 5,252,319, 5,209,926, 4,996,335, 4,927,807, 4,910,192, 4,710,495, 4,049,805, 4,004,005, 3,670,079, 3,608,076, 5,892,028, 5,888,995, 5,883,087, 5,880,115, 5,869,475, 5,866,558, 5,861,390, 5,861,388, 5,854,235, 5,837,698, 5,834,452, 5,830,886, 5,792,758, 5,792,757, 5,763,361, 5,744,462, 5,741,787, 5,741,786, 5,733,899, 5,731,345, 5,723,638, 5,721,226, 5,712,264, 5,712,263, 5,710,144, 5,707,984, 5,705,494, 5,700,793, 5,698,720, 5,698,545, 5,696,106, 5,677,293, 5,674,861, 5,661,141, 5,656,621, 5,646,136, 5,637,691, 5,616,574, 5,614,514, 5,604,215, 5,604,213, 5,599,807, 5,585,482, 5,565,588, 5,563,259, 5,563,131, 5,561,124, 5,556,845, 5,547,949, 5,536,714, 5,527,806, 5,506,354, 5,506,221, 5,494,907, 5,491,136, 5,478,956, 5,426,179, 5,422,262, 5,391,776, 5,382,661, 5,380,841, 5,380,840, 5,380,839, 5,373,095, 5,371,078, 5,352,809, 5,344,827, 5,344,826, 5,338,837, 5,336,686, 5,292,906, 5,292,878, 5,281,587, 5,272,140, 5,244,886, 5,236,912, 5,232,915, 5,219,879, 5,218,109, 5,215,972, 5,212,166, 5,206,415, 5,194,602, 5,166,201, 5,166,055, 5,126,488, 5,116,829, 5,108,996, 5,099,037, 5,096,892, 5,093,502, 5,086,047, 5,084,450, 5,082,835, 5,081,114, 5,053,404, 5,041,433, 5,041,432, 5,034,548, 5,032,586, 5,026,882, 4,996,335, 4,975,537, 4,970,205, 4,954,446, 4,950,428, 4,946,834, 4,937,237, 4,921,846, 4,920,099, 4,910,226, 4,900,725, 4,892,867, 4,888,336, 4,885,280, 4,882,322, 4,882,319, 4,882,315, 4,874,855, 4,868,167, 4,865,767, 4,861,875, 4,861,765, 4,861,763, 4,847,014, 4,774,236, 4,753,932, 4,711,856, 4,710,495, 4,701,450, 4,701,449, 4,689,410, 4,680,290, 4,670,551, 4,664,850, 4,659,516, 4,647,410, 4,634,695, 4,634,693, 4,588,530, 4,567,000, 4,560,557, 4,558,041, 4,552,871, 4,552,868, 4,541,956, 4,519,946, 4,515,787, 4,512,986, 4,502,989, 4,495,102; the disclosures of which are herein incorporated by reference.

Also of interest are analogs of the above compounds.

For all of the above active agents, the active agents may be present as pharmaceutically acceptable salts.

As indicated above, the active agent of the compositions are typically present in a pharmaceutically acceptable vehicle or carrier, e.g., as described below. In certain embodiments, the active agent is present in an amount of from about 0.1% to about 90% by weight, e.g., from about 1% to about 30% by weight of the active compound.

Pharmaceutically Acceptable Carrier

As summarized above, the compositions of the invention further include a pharmaceutically acceptable vehicle (i.e., carrier). Common carriers and excipients, such as corn starch or gelatin, lactose, dextrose, sucrose, microcrystalline cellulose, kaolin, mannitol, dicalcium phosphate, sodium chloride, and alginic acid are of interest. Disintegrators commonly used in the formulations of the invention include croscarmellose, microcrystalline cellulose, corn starch, sodium starch glycolate and alginic acid.

A liquid composition may comprise a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder. For example, a powder containing active compound, suspending agent, sucrose and a sweetener can be reconstituted with water to form a suspension; and a syrup can be prepared from a powder containing active ingredient, sucrose and a sweetener.

A composition in the form of a tablet or pill can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

"Controlled release", "sustained release", and similar terms are used to denote a mode of active agent delivery that occurs when the active agent is released from the delivery vehicle at an ascertainable and controllable rate over a period of time, rather than dispersed immediately upon application or injection. Controlled or sustained release may extend for hours, days or months, and may vary as a function of numerous factors. For the pharmaceutical composition of the present invention, the rate of release will depend on the type of the excipient selected and the concentration of the excipient in the composition. Another determinant of the rate of release is the rate of hydrolysis of the linkages between and within the units of the polyorthoester. The rate of hydrolysis in turn may be controlled by the composition of the polyorthoester and the number of hydrolysable bonds in the polyorthoester. Other factors determining the rate of release of an active agent from the present pharmaceutical composition include particle size, acidity of the medium (either internal or external to the matrix) and physical and chemical properties of the active agent in the matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example, liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methyl-cellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration.

A typical composition for intramuscular or intrathecal administration will be of a suspension or solution of active ingredient in an oil, for example, *Arachis* oil or sesame oil. A typical composition for intravenous or intrathecal administration will be a sterile isotonic aqueous solution containing, for example, active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol, a chelating agent, for example, ethylenediamine tetraacetic acid, and an anti-oxidant, for example, sodium metabisulphite may be included in the formulation. Alternatively, the solution can be freeze dried and then reconstituted with a suitable solvent just prior to administration.

The compounds of the invention and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. For example, see U.S. Pat. No. 5,023,252, herein incorporated by reference in its entirety. Such patches may be constructed for continuous, pulsatile, or on demand delivery of pharmaceutical agents.

Optionally, the pharmaceutical composition may contain other pharmaceutically acceptable components, such a buffers, surfactants, antioxidants, viscosity modifying agents, preservatives and the like. Each of these components is well-known in the art. For example, see U.S. Pat. No. 5,985,310, the disclosure of which is herein incorporated by reference.

Other components suitable for use in the formulations of the present invention can be found in Remington's Pharmaceutical Sciences, Mace Publishing Company, Philadelphia, Pa., 17th ed. (1985).

Identifiers

Also present in the subject compositions is an identifier. The identifier may vary depending on the particular embodiment and intended application of the composition. In certain embodiments, the identifier is a component that emits a signal upon activation by a stimulus, e.g., by interrogation, upon contact with a target physiological location, etc. As such, the identifier may be an identifier that emits a signal when it contacts a target body (i.e., physiological) site. In addition or alternatively, the identifier may be an identifier that emits a signal when interrogated.

In yet other embodiments, the identifier is an inert, but identifiable marker, e.g., an engraved identifier (such as one that is fabricated from a material or materials that survive digestion). This marker may then be identified, for example, following an autopsy or forensic examination. It is possible to provide a more internal device within a pill to determine both that its surface has partially been subject to digestion, but also that the inner pill material has also been digested. This application is particularly useful in experimental pharmacological settings. The identifier of these embodiments is one that does not necessarily emit a signal, but which can be optically inspected, e.g., visually or machine read, to obtain information about the composition with which it was associated prior to administration.

While the identifier may be an identifier that does not emit a signal, in certain embodiments (as summarized above) the identifier is one that does emit a signal. Depending on the needs of a particular application, the signal may be a generic signal, e.g., a signal that merely identifies that the composition has contacted the target site, or a unique signal, e.g., a signal which in some way uniquely identifies that a particular composition from a group or plurality of different compositions in a batch has contacted a target physiological site. As such, the identifier may be one that, when employed in a batch of unit dosages, e.g., a batch of tablets, emits a signal which cannot be distinguished from the signal emitted by the identifier of any other unit dosage member of the batch. In yet other embodiments, the identifier emits a signal that uniquely identifies a given unit dosage, even from other identical unit dosages in a given batch. Accordingly, in certain embodiments the identifier emits a unique signal that distinguishes a given type of unit dosage from other types of unit dosages, e.g., a given medication from other types of medications. In certain embodiments, the identifier emits a unique signal that distinguishes a given unit dosage from other unit dosages of a defined population of unit dosages, e.g., a prescription, a batch or a lifetime production run of dosage formulations. In certain embodiments, the identifier emits a signal that is unique, i.e., distinguishable, from a signal emitted by any other dosage formulation ever produced, where such a signal may be viewed as a universally unique signal (e.g., analogous to a human fingerprint which is distinct from any other fingerprint of any other individual and therefore uniquely identifies an individual on a universal level). In one embodiment, the signal may either directly convey information about the composition, or provide an identifying code, which may be used to retrieve information about the composition from a database, i.e., a database linking identifying codes with compositions.

The identifier may be any component or device that is capable of generating a detectable signal following activation in response to a stimulus. In certain embodiments, the stimulus activates the identifier to emit a signal once the composition comes into contact with a physiological target site, e.g., as summarized above. For example, a patient may ingest a pill that upon contact with the stomach fluids, generates a detectable signal. Depending on the embodiment, the target physiological site or location may vary, where representative target physiological sites of interest include, but are not limited to: a location in the gastrointestinal tract (such as the mouth, esophagus, stomach, small intestine, large intestine, etc.); another location inside the body, such as a parental location, vascular location, etc.; or a topical location; etc.

In certain embodiments the stimulus that activates the identifier is an interrogation signal, such as a scan or other type of interrogation. In these embodiments, the stimulus activates the identifier, thereby emitting a signal which is then received and processed, e.g., to identify the composition in some manner. In certain of these embodiments, the identifier may include a power source that transduces broadcast power and a signal generating element that modulates the amount of transduced power, such that a signal is not emitted from the identifier but instead the amount of broadcast power transduced by the identifier is detected and employed as the "signal." Such embodiments are useful in a variety of applications, such as applications where the history of a given composition is of interest, e.g., as reviewed in greater detail below.

In certain embodiments, the identifier is dimensioned to be complexed with the active agent/pharmaceutically acceptable carrier component of the composition so as to produce a composition that can be readily administered to a subject in need thereof. As such, in certain embodiments, the identifier element is dimensioned to have a width ranging from about 0.05 mm to about 1 mm, such as from about 0.1 mm to about 0.2 mm; a length ranging from about 0.05 mm to about 1 mm, such as from about 0.1 mm to about 0.2 mm and a height ranging from about 0.1 mm to about 1 mm, such as from about 0.05 mm to about 0.3 mm, including from about 0.1 mm to about 0.2 mm. In certain embodiments the identifier is 1 mm3 or smaller, such as 0.1 $mm^3$ or smaller, including 0.2 $mm^3$ or smaller. The identifier element may take a variety of different configurations, such as but not limited to: a chip configuration, a cylinder configuration, a spherical configuration, a disc configuration, etc., where a particular configuration may be selected based on intended application, method of manufacture, etc.

The identifier may generate a variety of different types of signals, including but not limited, RF, magnetic, conductive (near field), acoustic, etc.

As is known in the art (see, e.g., J. D. Jackson, *Classical Electrodynamics*, 2nd Edition, pp. 394-396 (1975)), the electric (E) and magnetic (B) fields for radiation of an oscillating electric dipole antenna with an angular frequency ω and corresponding wave number k (where k=ω/c, with c being the speed of light in the relevant medium) are given by the equations:

$$B = k^2 (n \times p) \frac{e^{ikr}}{r} \left(1 - \frac{1}{ikr}\right); \text{ and} \qquad (1)$$

$$E = k^2(n \times p) \times n \frac{e^{ikr}}{r} + [3n(n \cdot p) - p]\left(\frac{1}{r^3} - \frac{ik}{r^2}\right)e^{ikr}, \quad (2)$$

where n is a unit vector in the direction from the center of the dipole source to a location x at a distance r from the source, and p is a space-integrated density of electric charge given by (p=∫x'ρ(x')d³x')

As can be seen from Eqs. (1) and (2), in the "far field" region, where r>>λ (where the wavelength λ=2π/k), the electric and magnetic fields are dominated by terms that decrease with distance as 1/r. In this region, mutually perpendicular electric and magnetic fields feed off one another to propagate the signal through space. Where λ~r, the 1/r² ("induction") terms in Eqs. (1) and (2) become significant, and where λ>>r, an additional quasi-electrostatic term that varies as 1/r³ also becomes significant.

Conventional RF communication takes place at distances r~λ to r>>λ. For instance, implantable medical devices such as pacemakers typically communicate in the 405-MHz frequency band, corresponding to wavelengths of 0.75 meters, somewhat smaller than the scale of a human body. As is known in the art, higher frequencies are advantageously not used because structures within the body begin to absorb radiation, leading to undesirable signal loss; substantially lower frequencies (longer wavelengths) are generally regarded as undesirable because much of the energy is redirected into the induction and/or quasi-static field components rather than the far-field component that can be sensed using conventional antennas. It should also be noted that RFID applications with a transponder and a base unit typically use wavelengths such that r~λ and generally rely on magnetic induction to transmit power from the transponder to the base unit. In certain embodiments, these RF signals are employed.

In contrast to these approaches, certain embodiments of the present invention advantageously operate at wavelengths much larger than the human body (λ>>1 meter) to communicate information within the patient's body, e.g., as described in U.S. Provisional Application Ser. No. 60/713,680; the disclosure of which is herein incorporated by reference. For instance, in some embodiments, frequencies on the order of 100 kHz, corresponding to wavelengths of around 3 km (in air), are advantageously used. At distances r that are short as compared to the wavelength λ, the quasi-static electric field term in Eqs. (1) and (2) dominates, and thus the propagating signal is predominantly electrical rather than electromagnetic. Such signals readily propagate in a conductive medium such as the human body. For instance, at a frequency of 100 kHz and distances on the order of 1-2 meters, the quasi-static (1/r³) component of Eq. (2) is estimated to be on the order of $10^6$ times stronger than the far-field (1/r) component. Thus, long-wavelength signaling using near-field coupling is efficient. Further, because the signals are required to travel relatively short distances (typically 2 meters or less), detectable signals can be transmitted using very small antennas.

A wide range of frequencies may be used for transmission of signals. In some embodiments, the transmission frequency is within the "LF" band (low frequency, defined as 30-300 kHz) of the RF spectrum, below the frequency range of AM radio (around 500 to 1700 kHz). Within the LF band, the range from 160-190 kHz has been designated by the FCC for experimental use, with specified upper limits on external signal strength. In embodiments of the present invention where the signals are largely confined within the patient's body as described below, this experimental band can be used.

However, the invention is not limited to the 160-190 kHz band or to the LF (30-300 kHz band). Lower bands may also be used; for instance, in the VLF band (3-30 kHz, wavelengths of 10-100 km in air), signals can penetrate water to a distance of 10-40 meters. Since the electrical properties of the human body are similar to those of salt water, it is expected that signals in this band would also readily propagate through the body. Thus, any frequency band corresponding to a wavelength that is at least an order of magnitude larger than the human body—e.g., λ~10 m or longer, or frequencies on the order of 30 MHz or below—can be used.

While there is no necessary lower limit on the frequency of signals used, several practical considerations may affect the choice of frequency. For instance, it is well known that the human body carries low-level oscillating signals induced by nearby AC-powered devices, which operate at 60 Hz (US) or similar frequencies in other parts of the world. To avoid interference caused by AC electrical power systems, frequencies near 60 Hz are advantageously not used. In addition, as is known in the art, longer wavelengths correlate with lower information transfer rates, and the information-transfer capacity at long wavelengths (e.g., below the 3 kHz-30 kHz VLF band) may be too small for the amount of information that is to be transferred in a particular system. Further, longer wavelengths generally require longer dipole antennas to produce a detectable signal, and at some point the antenna size may become a limiting factor in frequency selection.

According to some embodiments of the invention, given a suitable choice of frequency, a signal strong enough to travel to a receiver within the body can be generated using a very small antenna. For instance, 100 kHz signals generated by a dipole antenna just a few millimeters long can be propagated to a receiver antenna placed 1-2 meters away. This quasi-electrostatic transmission is believed to be aided by the fact that the implanted antenna is directly in contact with a conductive medium, for example, the patient's tissues. For purposes of analyzing electrical properties, human tissue can be approximated as an electrolyte solution with electrical properties comparable to those of salt water. Thus, as in an electrolyte bath, the quasi-electrostatic field created by an oscillating dipole antenna induces an oscillating current in the body. As a result of the inherent electrical resistivity of the body (comparable to salt water), the oscillating current creates oscillating potential variations within the body that can be sensed using a suitable receiver. (See, e.g., L. D. Landau et al. *Electro-dynamics of Continuous Media*, Ch. 3 (1960)). Examples of suitable receivers include the leads of a pacemaker, which create a dipole with an axis of about 20 cm or any other implanted wires with length from 10-100 cm.

It should be noted that these currents are undesirable in the context of conventional RF communication, in which current flow in the near field leads to power loss in the far-field. In fact, many RF transmitters include devices designed to minimize near-field current leakage. In near-field transmitters of these embodiments of the present invention, maximizing such currents is desirable.

Further, for quasi-electrostatic signals, the patient's skin advantageously acts as a conductive barrier, confining the signals within the patient's body. This confines the signals within the body and also makes it difficult for stray external signals to penetrate the body and create noise or interference in the transmitted signals. Confinement of the signals can mitigate, to some extent, the $1/r^3$ falloff of the near-field signal, further reducing power requirements. Such effects have been observed in the laboratory, e.g., in a salt water bath, in which the water/air interface acting as a conductive barrier. Similar effects have been observed in communicating with submarines via RF transmission in the ELF (3-30 Hz) and SLF (30-300 Hz) bands. These effects have also been observed in sonar communications; although sonar uses acoustic, rather than electrical or electromagnetic, fields to transmit information, the surface of the water acts as a conductive barrier for acoustic energy and mitigates the fall-off of signal intensity with distance.

As a result of these phenomena, a transmitter with a very small antenna and a small power source are sufficient to create a near-field signal that is detectable within the patient's body. For instance, the antenna can be formed by a pair of electrodes a few millimeters or less in length, spaced apart by a few millimeters, with oscillating voltages of opposite phase applied to create an oscillating electric dipole. Such antennas can be disposed almost anywhere within the body.

Further, in some embodiments, the frequency, transmitter antenna length, and receiver antenna length are selected such that only microwatts of power are required to produce a detectable signal, where conventional RF communication (e.g., at around 405 MHz) would require at least milliwatts. Accordingly, very compact power supplies that produce only small amounts of power can be used; examples are described in Section IV below.

As such, depending on the particular embodiment of interest, the frequency may range from about 0.1 Hz or lower to about 100 mHz or higher, e.g., from about 1 kHz to about 70 mHz, including from about 5 kHz to about 200 kHz.

In certain embodiment, the signal that is emitted by the identifier is an acoustic signal. In these embodiments, any convenient acoustic signal generation element may be present in the identifier, e.g., a piezoelectric element, etc.

The transmission time of the identifier may vary, where in certain embodiments the transmission time may range from about 0.1 μsec to about 4 hours or longer, such as from about 1 sec to about 4 hours. Depending on the given embodiment, the identifier may transmit a signal once or transmit a signal two or more times, such that the signal may be viewed as a redundant signal.

In certain embodiments, the identifier may be one that is programmable following manufacture, in the sense that the signal generated by the identifier may be determined after the identifier is produced, where the identifier may be field programmable, mass programmable, fuse programmable, and even reprogrammable. Such embodiments are of interest where uncoded identifiers are first produced and following incorporation into a composition are then coded to emit an identifying signal for that composition. Any convenient programming technology may be employed. In certain embodiments, the programming technology employed is RFID technology. RFID smart tag technology of interest that may be employed in the subject identifiers includes, but is not limited to: that described in U.S. Pat. Nos. 7,035,877; 7,035,818; 7,032,822; 7,031,946, as well as published application no. 20050131281, and the like, the disclosures of which are herein incorporated by reference. With RFID or other smart tag technology, a manufacturer/vendor may associate a unique ID code with a given identifier, even after the identifier has been incorporated into the composition. In certain embodiments, each individual or entity involved in the handling of the composition prior to use may introduce information into the identifier, e.g., in the form of programming with respect to the signal emitted by the identifier, e.g., as described in U.S. Pat. No. 7,031,946 the disclosure of which is herein incorporated by reference.

The identifier of certain embodiments includes a memory element, where the memory element may vary with respect to its capacity. In certain embodiments, the memory element has a capacity ranging from about 1 bit to 1 gigabyte or more, such as 1 bit to 1 megabyte, including from about 1 bit to about 128 bit. The particular capacity employed may vary depending on the application, e.g., whether the signal is a generic signal or coded signal, and where the signal may or may not be annotated with some additional information, e.g., name of active agent, etc.

Identifier components of embodiments of the invention have: (a) an activation component and (b) a signal generation component, where the signal generation component is activated by the activation component to produce an identifying signal, e.g., as described above.

Activation Component

The activation component is a component that activates the signal generation element to emit a signal upon experience of a stimulus, e.g., contact of the composition with a target physiological site of interest, such as the stomach. The activation component may be configured to be activated in a number of different ways. The following sections detail certain different ways in which the identifier may be activated. As can be seen from the following review, the activation component may or may not be integrated with a power source, e.g., a battery. Illustrative activation approaches include, but are not limited to: Battery Completion, e.g., Battery activated by electrolyte addition and Battery activated by cathode or anode addition; Battery connection, e.g., Battery activated by conductor addition; Transistor-mediated Battery Connection, e.g., Battery activated by transistor gate, Geometry Modification, Detection of Geometry Modification by Resonant Structure, Pressure Detection, Resonant Structure Modification; etc. Each of these illustrative activation approaches is now reviewed in greater detail.

Battery Completion

Battery Activated by Electrolyte Addition

In these embodiments, the battery includes, when completed, a cathode, an anode, and an electrolyte. When the composition (e.g., pill) is administered, e.g., ingested, and travels through the esophagus, it proceeds to enter the stomach. The cathode and anode provided within the composition do not constitute a full battery. However, as the composition dissolves to expose the cathode and anode, the stomach fluid acts as the electrolyte component of the battery. The added component of the stomach fluid thus completes the battery. Therefore, as the composition contacts the target site, e.g., by entering the stomach and dissolving to the point of cathode and anode exposure, a power source is provided which activates the identifier, e.g., in chip configuration. The data signal is then transmitted. This configuration is described in greater detail below, e.g., in terms FIG. 4.

Battery Activated by Cathode or Anode Addition

In an extension of this approach, the system is activated by having the triggering event add a cathode or anode component, with the electrolyte being intrinsic in the partial, pre-battery configuration. The battery is completed, producing power and activating the composition, although not necessarily at the identical point of time.

Battery Connection
Battery Activated by Conductor Addition

In another embodiment of the present invention, the battery is connected to the circuitry when it enters the stomach. The battery becomes connected, and thus activates the identifier, by conductor addition. In this case, there is a physically complete battery and a complete chip. When these two components are awash in physiological fluid, such as in the stomach, they become electronically connected. This triggering event electrically connects the battery to the signaling microchip, thus activating the smart pill.

Transistor-Mediated Battery Connection
Battery Activated by Transistor Gate

Another design allowing the battery and the chip together to activate the smart pill has the feature of a transistor gate between the battery and the reporting chip. Once the transistor gate is switched on, such as by activation with the stomach, the reporting signal is transmitted.

There are numerous methods well known to the ordinary skilled artisan for turning on a transistor gate. Most of them involve activating the gate by closing a switch, which can include a transistor switch or other types of switches.

The gate can be activated by applying a small gate current. This is how, for example, transistors are typically activated. The gate current can be generated in any number of ways well known to the ordinary skilled artisan. Any circuitry which detects the presence of the pill in the environment of interest, such as the stomach, generates the gate current and turns the system on.

The gate current can be turned on by detecting a conductivity variation. For instance, a circuit can be provided that detects a small change in the conductivity of the stomach. While the stomach is conductive, the pill might not be. As a result, when the conductivity variation is detected, the transistor gate is activated, turning the smart pill on and generating a reporting signal.

The conductivity can be modulated by a change in the solution concentration. By example, the system detects a different solution concentration in the stomach in contrast to areas outside the stomach. The solution pH is detected, by a modulation of the conductivity, which turns on the gate, and turn on the pill generating a reporting signal.

The stomach contains ionic conductive fluids. Those ionic conductive fluids can be employed to modulate the conductivity of the gate and turn on the smart pill, generating a reporting signal. Individual enzymes can be detected in the stomach. For instance, a chem-FET can be employed that looks for the pepsin content in the stomach, turning the pill on, thus reporting the presence of the enzyme.

Temperature change can also be detected using the innovations of the present invention. The stomach is typically a steady 37° C. Areas outside the stomach are more typically 20° C. or less. When the pill enters the stomach and becomes heated up, the pill is so designed that this adjusts the conductivity and turn the identifier on, generating a reporting signal.

The conductivity of the transistor can be modified by a microscopic property called carrier mobility. A detection approach using this property uses the transistor itself as a detector. The carrier mobility is modulated by temperature, a well-known phenomenon. In this manner, the transistor is used as a temperature sensor by using that transistor to turn on the smart pill, generating a reporting signal.

Another approach is to change the charge on the gate of a MOSFET transistor. The gate charge can be modulated by the factors to be detected. This is again a configuration using the transistor to turn on the circuit, generating a reporting signal.

In another configuration, the gate charge is modulated by a material to be detected in the solution. A specific ion would preferentially change the gate charge. This system is modulated by a crystal potential. A crystal potential occurs when crystals generate electric fields under certain circumstances.

The electric field can change the charge on the gate, turning on the transistor and generating a reporting signal. This change may be modulated by a chemical potential, resulting from an osmotic or ionic process. This causes charge to accumulate on the gate, thereby, turning it on and generating a reporting signal.

A change in the electrical potential can also cause a reporting signal using a variety of potentials. For example, a gravitational potential can detect the change in height of the detector. In the case of a patient swallowing the pill, the change in pill height would indicate ingestion.

In another embodiment, a transistor gate has associated with it a capacitance. That capacitance is then modulated by certain properties peculiar to the target site, e.g., the stomach.

In one case, the capacitance is changed by being enveloped in the stomach. This effect on the capacitance is then detected. The gate charge is modulated by change in the carrier concentration. The carrier concentration is modulated by temperature. This approach provides a slightly different approach, but similar in concept to using the transistor as a temperature sensor as above.

Geometry Modification

A transistor structure is also provided that has a geometry that changes. Gate capacitance is determined by a change in geometry which occurs in the stomach, detecting a change in capacitance. These changes can take place in a variety of ways, for example, as further described below.

A variety of physiologic factors change the geometry. Pressure in the stomach different than pressure outside occurs with the natural squeezing during the production of chyme, as well as at other times. This changes the gate capacitance. The change is detected by having a dielectric on the gate. In this case, the gate consists of a number of layers, one of which is the dielectric.

In an additional embodiment, the enzymes of the stomach dissolve the dielectric, changing the gate capacitance, which is then detected. Various physical and chemical conditions within the stomach dissolve that gate dielectric, thereby activating the circuit.

Detection of Geometry Modification by Resonant Structure

A resonant structure on the gate is provided in other variants. In this case, a mechanical structure is provided that has a characteristic frequency. This frequency is excited by the triggering event, and measured. Various interactions with the stomach will cause a change in that resonance.

Pressure Detection

Gate capacitance and resonance with modulation source can also be utilized for detection. In this case, an excitation is provided to the resonance structure from a modulation source, such as a sound wave. The gate capacitance of that resonance structure can be used to detecting pressure waves. A resonance structure sits out in the stomach and is hooked up to a detection circuit on a transistor. In the stomach, the resonance circuit detects pressure waves.

Of pressure sound waves within the body, there are particular sounds that are characteristic, such as the heart beat and respiration. These sounds are detected and used to turn the circuit on.

Pressure waves are also detected by resonant Q factor modulation. Q factor modulation can be accomplished in a number of different manners. The resonance structure has two components, a frequency and a Q factor. The Q factor is modulated by detecting some environmental change.

Resonant Structure Modification

By example, the structure has a very different Q factor in air than it does in the fluid of the stomach. Thus, the dampening can be detected by the fluid viscosity. Additionally, the structure can be configured to be eaten away by the acid or some of the enzymes in the stomach, which changes the cue.

Degradation by stomach acid or enzymes also changes the resonant frequency. It is simple to detect the frequency shift of such a structure. The frequency is shifted as this structure is changed in the stomach. There are two approaches to modifying the structure. A catabolic process can occur where the structure gets dissolved, which is easily detectable. Also, an anabolic process would occur where an enzyme from the stomach binds to this structure, making it larger. This effect will also modify the resonance structure. The resonance modification is detected either as a frequency change or a Q factor modulation.

Battery Power Sources

As reviewed above, in certain embodiments, the activation element is a power source that is turned on upon contact of the power source with a target site, e.g., a physiological target site, such as the stomach, e.g., stomach acid. In certain embodiments, the power source is a battery that is turned on to provide power upon contact with the physiological target site, where the battery is coupled to the signal generation component such that when the battery is turned on, the signal generation component emits the identifying signal.

In certain embodiments, the battery that is employed is one that comprises two dissimilar materials which constitute the two electrodes of the battery. In certain embodiments, these two materials are shielded from the surrounding environment by an additional layer of material. When the shielding material (e.g., active agent/carrier matrix), is dissolved or eroded by the surrounding fluid, the electrode materials are exposed and come in contact with the body fluid, such as stomach acid or other types of electrolyte fluid. A potential difference, that is, a voltage, is generated between the electrodes as a result of the respective oxidation and reduction reactions incurred to the two electrode materials. A voltaic cell, or battery, can be thereby formed. Accordingly, in embodiments of the invention, such batteries are configured such that when the two dissimilar materials are exposed to the target site, e.g., the stomach, the digestive tract, etc., during the physical and chemical erosion of the composition in which the signal generation element is present, a voltage is generated. In such embodiments, the power source described above is not a "battery" in the common sense of the word, but rather as defined in the discipline of physics. The two dissimilar materials in an electrolyte are at different potentials, similar to the physics model of a 'potato battery'. As an example, copper and zinc when put into a cell have different potentials. Similarly, gold and magnesium have different potentials. As a result, a potential difference between the two dissimilar materials is generated.

Various battery-activation configurations are possible. Representative types of cell-activation approaches include, but are not limited to: activation by presence of electrolyte, activation by presence of a cathode material, activation by presence of a conductive material.

After the battery is activated, further activation configurations can be employed to activate the signal generation component. For example, the signal generation component can be activated through the activation of the gate of a metal oxide semiconductor (MOS) circuit, such as a CMOS switch. Activation of the gate of the MOS circuit can be based on one or more parameters, which include but are not limited to: gate current, gate charge, and gate capacitance.

The gate current, for activation purposes, can be a function of the conductivity of surrounding body fluids or tissues. Such conductivity can further be a function of one or more parameters, which include but are not limited to: solution concentration, solution pH value, ionic content of solution, enzymatic content of solution, temperature, and carrier mobility. Carrier mobility can also be a function of temperature.

Similarly, the gate charge can be a function of one or more parameters, which include but are not limited to: solution composition, crystal potential, electrical potential, gravitational potential, gate capacitance, and carrier concentration. The carrier concentration can also be a function of temperature.

The gate capacitance can be a function of the capacitive geometry of the gate, which can further be a function of pressure, a resonant input, or the characteristics of a dielectric material coupled to the gate. The characteristics of the dielectric material can vary with one or more parameters, which include but are not limited to: chemical contents of a digestive tract, chemical character of a physiological location, and amount of dissolution of the dielectric material in body fluids.

In certain embodiments, the battery is one that is made up of active electrode materials, electrolyte, and inactive materials, such as current collectors, packaging, etc. The active materials are any pair of materials with different electrochemical potentials. Suitable materials are not restricted to metals, and in certain embodiments the paired materials are chosen from metals and non-metals, e.g., a pair made up of a metal (such as Mg) and a salt (such as Cup. With respect to the active electrode materials, any pairing of substances—metals, salts, or intercalation compounds—with suitably different electrochemical potentials (voltage) and low interfacial resistance are suitable.

A variety of different materials may be employed as the battery electrodes. In certain embodiments, electrode materials are chosen to provide for a voltage upon contact with the target physiological site, e.g., the stomach, sufficient to drive the signal generation element of the identifier. In certain embodiments, the voltage provided by the electrode materials upon contact of the metals of the power source with the target physiological site is 0.001 V or higher, including 0.01 V or higher, such as 0.1 V or higher, e.g., 0.3 V or higher, including 0.5 volts or higher, and including 1.0 volts or higher, where in certain embodiments, the voltage ranges from about 0.001 to about 10 volts, such as from about 0.01 to about 10 V.

Materials and pairings of interest include, but are not limited to those reported in Table 1 below.

TABLE 1

|  | Anode | Cathode |
|---|---|---|
| Metals | Magnesium, Zinc Sodium (†), Lithium (†) Iron | |
| Salts | | Copper salts: iodide, chloride, bromide, sulfate, |

TABLE 1-continued

| Anode | Cathode |
|---|---|
| | formate, (other anions possible) |
| | $Fe^{3+}$ salts: e.g. orthophosphate, pyrophosphate, (other anions possible) |
| | Oxygen (††) on platinum, gold or other catalytic surfaces |
| Intercalation compounds | Graphite with Li, K, Ca, Na, Mg |
| | Vanadium oxide Manganese oxide |

†Protected anodes: certain high energy anode material such as Li, Na, and other alkali metals are unstable in their pure form in the presence of water or oxygen. These may however be used in an aqueous environment if stabilized. One example of this stabilization is the so-called "protected lithium anode" developed by Polyplus Corporation (Berkeley, CA), where a polymer film is deposited on the surface of lithium metal to protect it from rapid oxidation and allow its use in aqueous environment or air ambient. (Polyplus has IP pending on this).
††Dissolved oxygen can also serve as a cathode. In this case, the dissolved oxygen in the bodily fluids would be reduced to OH— at a suitable catalytic surface such at Pt or gold. Other catalysts are also possible.

In certain embodiments, one or both of the metals may be doped with a non-metal, e.g., to enhance the voltage output of the battery. Non-metals that may be used as doping agents in certain embodiments include, but are not limited to: sulfur, iodine and the like.

In certain embodiments, the electrode materials are copper iodine (CuI) as the anode and magnesium (Mg) as the cathode. Embodiments of the present invention use electrode materials that are not harmful to the human body.

In certain embodiments, the batteries have a small form factor. Batteries may be 10 $mm^3$ or smaller, such as 1.0 $mm^3$ or smaller, including 0.1 $mm^3$ or smaller, including 0.02 $mm^3$ or smaller. As such, in certain embodiments, the battery element is dimensioned to have a width ranging from about 0.05 mm to about 1 mm, such as from about 0.1 mm to about 0.2 mm; a length ranging from about 0.05 mm to about 1 mm, such as from about 0.1 mm to about 0.2 mm and a height ranging from about 0.1 mm to about 1 mm, such as from about 0.05 mm to about 0.3 mm, including from about 0.1 mm to about 0.2 mm.

As reviewed below, in certain embodiments the battery has a split or segmented configuration.

In certain embodiments, the battery is one which is free of packaging. As such, the electrodes are exposed and not protected by any protecting or sealing structure. As such, following removal of the active agent/carrier matrix material with which the battery may be associated, the battery per se does not itself include an protective packaging such that the electrodes are free to contact the electrolyte at the target physiological location.

Figure 4:
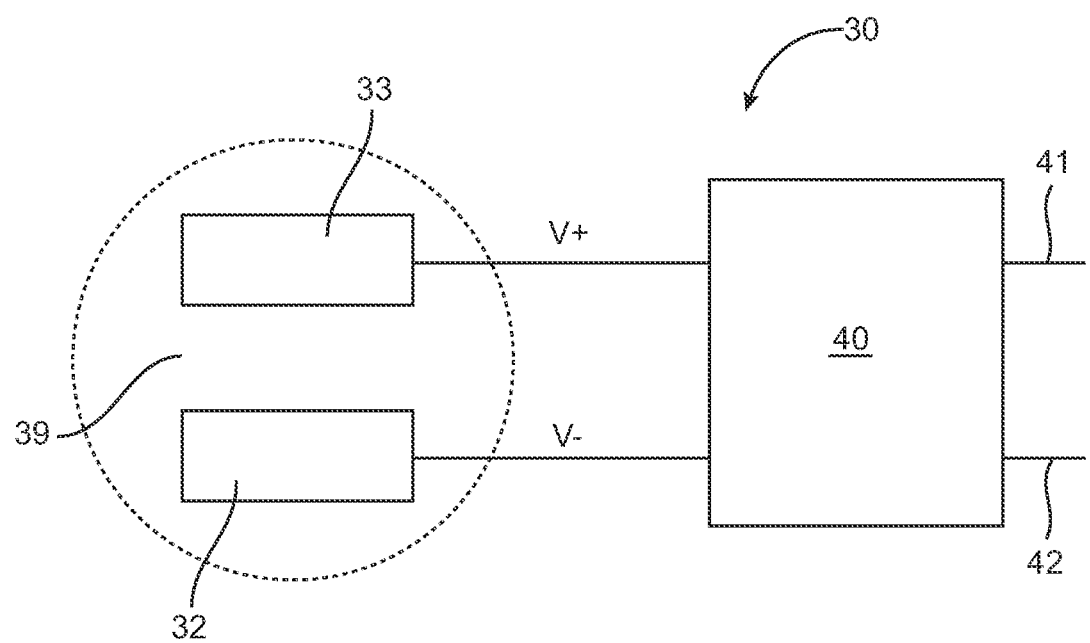
FIG. 4 shows diagrammatically the effects of the pill ingestion where some of the pill has eroded away.

In certain of these embodiments, the battery power source may be viewed as a power source that exploits reverse electrolysis in an ionic solution such as gastric fluid, blood, or other bodily fluids and some tissues. FIG. 4 illustrates an identifier 30 having a signal generation element 40 powered by reverse electrolysis. Signal generation element 40 is electrically connected to metal electrodes 32 and 33, which are made of two different materials and are electrically insulated from each other. When metal electrodes 32 and 33 are immersed in an ionic solution 39, a potential difference develops between them; for instance, electrode 33 rises to a higher potential V+ while electrode 32 falls to a lower potential V−. This potential difference can be used to power circuitry 40.

Electrodes 32 and 33 can be implemented in various ways; for instance, areas on opposing surfaces of an integrated circuit chip can be coated with two different metals, and the entire chip can be placed in the ionic solution. Alternatively, electrodes 32 and 33 may extend away from element 40 as shown. Other arrangements may also be used.

As illustrated above, electrodes 32 and 33 can be made of any two materials appropriate to the environment in which the identifier 30 will be operating. For instance, in some embodiments where ionic solution 39 comprises stomach acids, electrodes 32 and 33 may be made of a noble metal (e.g., gold, silver, platinum, palladium or the like) so that they do not corrode prematurely. Alternatively, the electrodes can be fabricated of aluminum or any other conductive material whose survival time in the applicable ionic solution is long enough to allow identifier 30 to perform its intended function.

Where the power source is a battery, the battery may be fabricated in a number of different ways. In certain embodiments, fabrication protocols which may be categorized as "planar" processing protocols are employed, as developed in greater detail below.

Additional Power Sources

Other sources, internal or external to the remote device, may also be employed in addition to or instead of those described above. For example, chemical or radioisotope batteries with a suitable form factor may be used to power some remote devices. Recently-developed fuel cells that use blood as an energy source can be miniaturized and used to provide electrical energy for a low-power microchip. Piezoelectric crystals that convert mechanical energy (e.g., compression) to electrical energy can be employed for remote devices disposed where suitable mechanical forces can be brought to bear, such as in or around the heart, stomach, joints, or other moving parts of the body. In yet other embodiments, a power source modeled on the cellular energy factory, with power being extracted from ATP in the blood so that blood, in effect, "nourishes" the identifier, is employed. In other embodiments, acoustic energy (e.g., ultrasound) can be coupled into a remote device through piezoelectric or similar converters.

In yet other embodiments, the activation element is not an on board power source, but an element that is powered from a separate power source and provides an activation signal to the signal generation component upon contact of the composition with the target site. For example, the activation element may be coupled to a power receiver which is configured to receive broadcast power and transduce the broadcast power into a form suitable for driving the signal generation element. In certain embodiments, the power receiver may be a coil. Alternatively, the activator component may be powered by a distinct power source, e.g., a sealed battery, a power element that converts mechanical energy of the pill into electrical power, e.g., a piezoelectric power element, etc. As such, the activator may or may not itself be the power source, and in those embodiments where it is not the power source, the identifier may include a distinct power source, such as receiver or power generator.

Signal Generation Component

The signal generation component of the identifier element is a structure that, upon activation by the activation component, emits a detectable signal, e.g., that can be received by a receiver, e.g., as described in greater detail below. The signal generation component of certain embodiments can be any convenient device that is capable of producing a detectable signal and/or modulating transduced broadcast power, upon activation by the activation component. Detectable signals of interest include, but are not limited to: conductive signals, acoustic signals, etc. As reviewed above, the signals emitted by the signal generator may be generic or unique signals, where representative types of signals of interest include, but are not limited to: frequency shift coded signals; amplitude modulation signals; frequency modulation signals; etc.

In certain embodiments, the signal generation element includes circuitry, as developed in more detail below, which produces or generates the signal. The type of circuitry chosen may depend, at least in part, on the driving power that is supplied by the power source of the identifier. For example, where the driving power is 1.2 volts or above, standard CMOS circuitry may be employed. In other embodiments where the driving power ranges from about 0.7 to about 1.2 V, sub-threshold circuit designs may be employed. For driving powers of about 0.7 V or less, zero-threshold transistor designs may be employed.

In certain embodiments, the signal generation component includes a voltage-controlled oscillator (VCO) that can generate a digital clock signal in response to activation by the activation component. The VCO can be controlled by a digital circuit, which is assigned an address and which can control the VCO with a control voltage. This digital control circuit can be embedded onto a chip that includes the activation component and oscillator. Using amplitude modulation or phase shift keying to encode the address, an identifying signal is transmitted.

The signal generation component may include a distinct transmitter component that serves to transmit the generated signal to a remote receiver, which may be internal or external to the patient, as reviewed in greater detail below. The transmitter component, when present, may take a number of different configurations, e.g., depending on the type of signal that is generated and is to be emitted. In certain embodiments, the transmitter component is made up of one or more electrodes. In certain embodiments, the transmitter component is made up of one or more wires, e.g., in the form of antenna(e). In certain embodiments, the transmitter component is made up of one or more coils. As such, the signal transmitter may include a variety of different transmitters, e.g., electrodes, antennas (e.g., in the form of wires) coils, etc. In certain embodiments, the signal is transmitted either by one or two electrodes or by one or two wires. A two-electrode transmitter is a dipole; a one electrode transmitter forms a monopole. In certain embodiments, the transmitter only requires one diode drop of power.

Figure 6A:
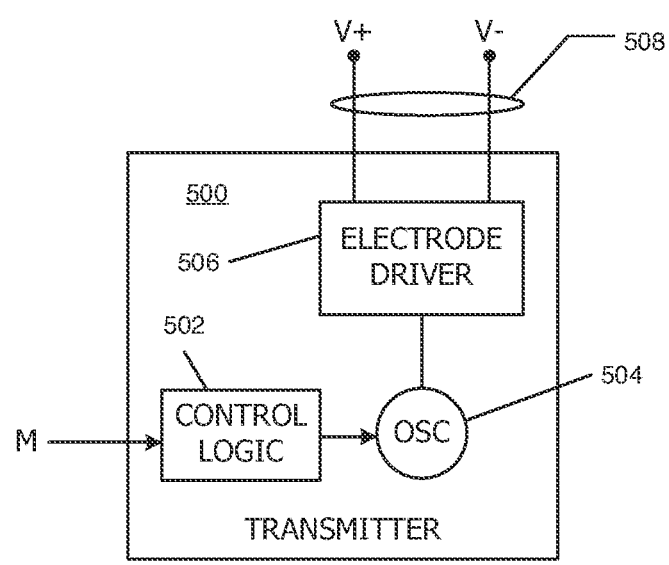
FIGS. 6A to 6D provide detail of certain implementations of electronic circuits of various embodiments of the invention.

In some embodiments, the transmitter unit uses an electric dipole or electric monopole antenna to transmit signals. FIG. 6A illustrates a dipole antenna. Oscillator 504 provides driving signals ($\phi$ and an inverted signal denoted herein as /$\phi$) to an electrode driver 506. FIG. 6C is a circuit diagram showing details of a dipole electrode driver 600 implemented using conventional CMOS driver circuits. Electrode 602 is driven to a potential $E_0$ by transistors 604, 606 in response to driving signal $\phi$ while electrode 608 is driven to a potential $E_1$ by transistors 610, 612 in response to inverted driving signal /$\phi$. Since driving signals $\phi$ and $\phi$ oscillate with opposite phase, potentials $E_0$ and $E_1$ also oscillate with opposite phase. It will be appreciated that driver 600 and all other electronic circuits described herein can be implemented using sub-micron CMOS processing technologies known in the art; thus, the size of the circuitry is not a limiting factor on the size of a remote device.

In some embodiments, a monopole antenna can be substituted for the dipole antenna of FIG. 6A. FIG. 6D illustrates a driver circuit for a monopole antenna that can be implemented in conventional CMOS integrated circuits. This antenna driver is generally similar to one half of the driver circuit of FIG. 6C, with driver transistors 702, 704 driving a single electrode 706 to a potential $E_m$ in response to driving signal 4).

In either the dipole or monopole case, the driver circuit is powered by a potential difference ($\Delta V$) between terminals V+ and V−. This potential difference, which can be constant or variable, as desired.

FIG. 6A is a block diagram of a transmitter signal generation element 500 for an identifier according to an embodiment of the present invention. In this embodiment, generation element 500 receives a signal M from the activation component which activates the signal generation element to produce and emit a signal. Signal generation element 500 includes control logic 502, an oscillator 504, an electrode driver 506, and an antenna 508 (in this instance, a pair of electrodes operated as an electric dipole antenna). In operation, oscillator 504 generates an oscillating signal (waveform) in response to signals from control logic 502. The signals from control logic 502 can start or stop the oscillator and in some embodiments can also shape one or more aspects of the oscillatory signal such as amplitude, frequency, and/or phase. Oscillator 504 provides the waveform to electrode driver 506, which drives current or voltage on antenna 508 to transmit a signal into the conductive medium of body tissues or fluids.

Depending on a given embodiment, the signal may or may not be modulated. For example, in certain embodiments the frequency of the signal may be held constant. In yet other embodiments, the signal may be modulated in some manner, e.g., via carrier based modulate schemes, ultra-wide band (or time domain based) modulation schemes, etc.

Referring again to FIG. 6A, in some embodiments, oscillator 504 operates at a constant frequency. The receipt of a constant-frequency signal in and of itself can provide useful information, e.g., that a remote device is present and operational. In some embodiments, oscillator 504 modulates its signal to encode additional information.

Information can be encoded in various ways, generally by modulating (varying) some property of the transmitted signal, such as frequency, amplitude, phase, or any combination thereof. Modulation techniques known in the art may be employed.

In general, information can be transmitted using analog or digital techniques. "Analog techniques" refers generally to instances in which the modulated property is varied in different degrees, with the degree of variation being correlated to a value representing the information to be transmitted. For instance, suppose that element 500 is transmitting a signal. Oscillator 504 can be designed to operate over some range of frequencies. "Digital techniques" refers generally to instances in which the information to be transmitted is represented as a sequence of binary digits (bits), and the signal is modulated based on the bit stream. For instance, suppose again that transmitter 500 is transmitting a signal using digital techniques. Oscillator 504 can be designed to operate at least two different frequencies, with one frequency corresponding to bit value 0 and another frequency corresponding to bit value 1. In embodiments of the present invention, either analog techniques, digital techniques, or a combination thereof can be used to transmit information. In addition, various types of modulation may be implemented.

For instance, in one embodiment, frequency modulation is used. Oscillator 504 can be a voltage-controlled oscillator (VCO), an oscillator circuit in which the oscillation frequency depends on an applied voltage. Control logic 502 supplies an appropriate voltage (e.g., reflecting the value of the measurement data, M), and the frequency of the signal indicates the value of the data. In another embodiment, amplitude modulation is used; for instance, the amplitude of the driving signals ϕ and /ϕ can be varied, or the positive and negative rails of the driver circuit (e.g., V+ and V−) can be varied to control the amplitude. In another embodiment, phase modulation is used. For instance, in digital signal transmission, one phase corresponds to bit value 0, an opposite phase corresponds to bit value 1, and the phase shifts represent transitions. Oscillator 504 can include a switch circuit that either directly connects or cross-connects the driving signals ϕ and /ϕ to the inputs of a driver circuit. Combinations of frequency modulation, amplitude modulation, and/or phase modulation may also be used as desired.

In some embodiments, the transmitter may transmit a "packet" that includes a unique identifier for the identifier, which in turn is for the composition with which the identifier is associated. The unique identifier may also provide information from the remote device (e.g., the identity of the active agent (i.e., annotation information)). Other techniques for distinguishing different signals may also be used, including: operating different transmitters in different frequency bands, allowing each transmitter to be identified by its frequency and/or configuring different transmitters to transmit at different (and known) times, allowing the transmitter to be identified by when it transmits.

Additional Components

Depending on the particular embodiment, the identifier may include a number of different additional components. Some components of interest include, but are not limited, those reviewed below.

Power Enhancers

Where the activator is a power source that is turned on upon contact with a target physiological site, in certain embodiments, circuits for enhancing or boosting voltage output of the power source, e.g., battery, are provided, e.g., charge pumping circuits, charge doublers, etc. Such voltage enhancing elements may enhance the voltage output by at about 2-fold or more, such as by about 5-fold or more.

Power Storage

In certain embodiments, the activation component includes a power storage element. For example, a duty cycle configuration may be employed, e.g., where slow energy production from a battery is stored in a power storage element, e.g., in a capacitor, which then provides a burst of power that is deployed to the signal generation component. In certain embodiments, the activation component includes a timing element which modulates, e.g., delays, delivery of power to the signal generation element, e.g., so signals from different compositions, e.g., pills, that are administered at substantially the same time are produced at different times and are therefore distinguishable.

Additional Features

In certain embodiments, the compositions are characterized by having one or more of the following features. In certain embodiments, the compositions include an identifier which employs a conductive near-field mode of communication in which the body itself is employed as a conductive medium. In such embodiments, the compositions include circuitry that, when freed from the composition upon disruption of the composition (e.g., as described above) the circuitry comes into direct contact with the body and does not remain encapsulated or protected in some manner. In these embodiments, the signal is not a magnetic signal or high frequency (RF) signal. In certain embodiments, the systems are ones that include a receiver which is stably associated with the body, e.g., implanted or topically applied to an external location, such that the systems are distinguished from those in which an external device that is not stably associated with the body is employed to collect data. In certain embodiments, the compositions do not include an imaging system, e.g., camera or other visualization or imaging element, or components thereof, e.g., CCD element, illumination element, etc. In certain embodiments, the compositions do not include a sensing element, e.g., for sensing a physiological parameter, beyond the activator which detects contact with the targeted physiological site. In certain embodiments, the compositions do not include a propulsion element. In certain embodiments, the compositions do not include a sampling element, such as a fluid retrieval element. In certain embodiments, the compositions do not include an actuatable active agent delivery element, such as an element that retains an active agent with the composition until a signal is received that causes the delivery element to release the active agent.

Identifier Fabrication

In certain embodiments of interest, the identifier element includes a semiconductor support component. Any of a variety of different protocols may be employed in manufacturing the identifier structures and components thereof. For example, molding, deposition and material removal, e.g., planar processing techniques, such as Micro-Electro-Mechanical Systems (MEMS) fabrication techniques, including surface micromachining and bulk micromachining techniques, may be employed. Deposition techniques that may be employed in certain embodiments of fabricating the structures include, but are not limited to: electroplating, cathodic arc deposition, plasma spray, sputtering, e-beam evaporation, physical vapor deposition, chemical vapor deposition, plasma enhanced chemical vapor deposition, etc. Material removal techniques included, but are not limited to: reactive ion etching, anisotropic chemical etching, isotropic chemical etching, planarization, e.g., via chemical mechanical polishing, laser ablation, electronic discharge machining (EDM), etc. Also of interest are lithographic protocols. Of interest in certain embodiments is the use of planar processing protocols, in which structures are built up and/or removed from a surface or surfaces of an initially planar substrate using a variety of different material removal and deposition protocols applied to the substrate in a sequential manner.

Figure 11A:
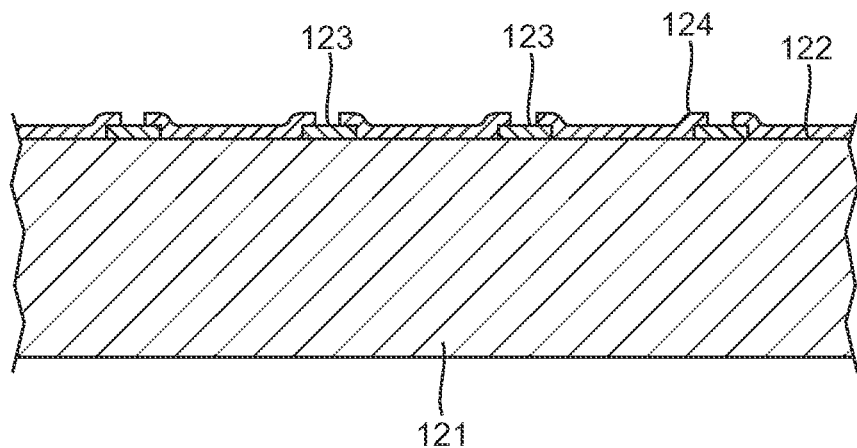
FIGS. 11A to 13B are diagrams showing a method for fabricating an identifier according to an embodiment of the invention.
Figure 11B:
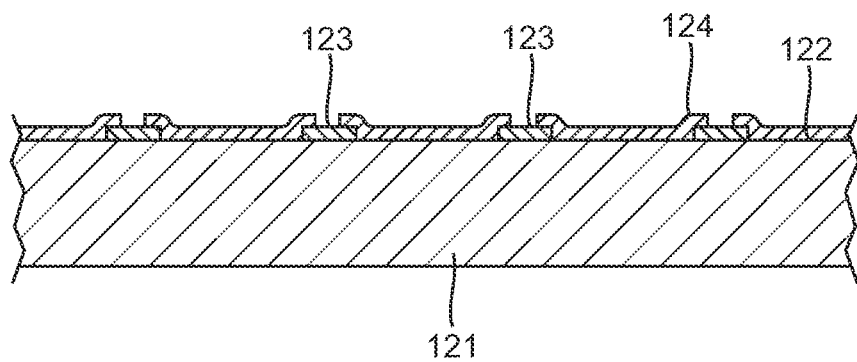

FIGS. 11A to 13B are diagrams showing a method for fabricating an identifier according to an embodiment of the invention. FIG. 11A depicts a cross-section of a semiconductor wafer, 121, processed by silicon foundry such as IBM or Taiwan Semiconductor Manufacturing Company. The top surface of the wafer, 122, contains numerous electrical contact pads, 123, and an insulating dielectric layer, 124. The contact pads can be Al but could also be Cu, Ti, or similar metal; the dielectric may be a combination of $SiO_2$ and $Si_3N_4$, but could be other insulators. In the first process step, shown in FIG. 11B, wafer 121 has been thinned from the back side via grinding or chemical/mechanical polishing to reduce thickness to a desired thickness. A final thickness might be about 300 μm but it can range from about 10 to about 1000 μm such as from about 50-about 500.

Figure 12A:
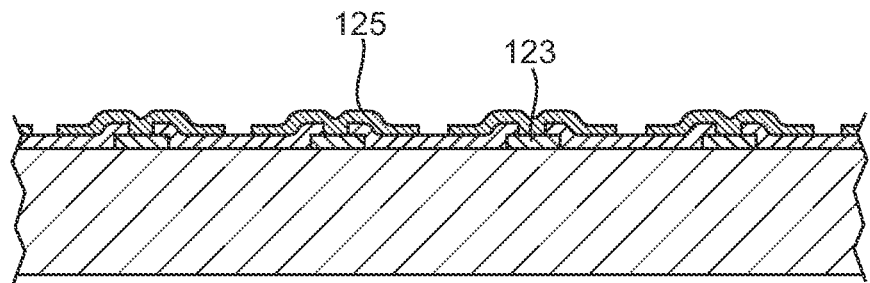

FIG. 12A shows the second process step, in which a layer of corrosion resistant metal, 125, has been added to the front side of the wafer to cover the electrical contacts, 123. The typical metal is platinum but one could also use other corrosion resistant metals such as Au, Ti, Ir, or another platinum group metal. The corrosion resistant metal may be deposited by physical vapor deposition, for example, and may be from about 0.05 to about 100 μm thick, such as from about 0.5 to about 5 μm thick. The metal 125 is formed into a desired pattern via photolithography and etching which are standard semiconductor processing techniques.

Figure 12B:
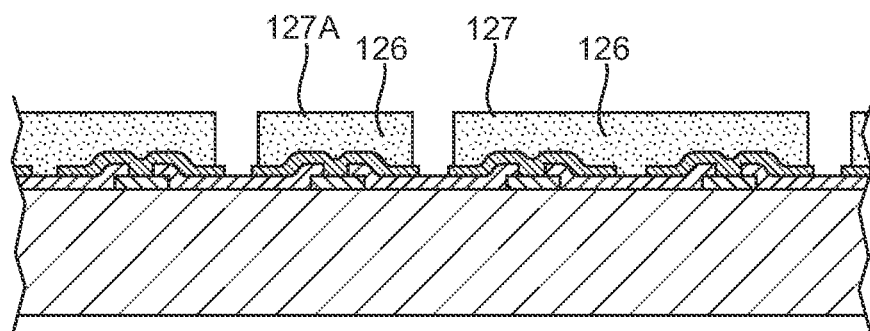

FIG. 12B shows the deposition of the cathode material 126. Cathode materials of interest include, but are not limited to: Cu or CuI, e.g., as described above. They are deposited by physical vapor deposition, electrodeposition, or plasma deposition, among other protocols. The cathode may be from about 0.05 to about 500 μm thick, such as from about 5 to about 100 μm thick. The cathode shape is controlled by shadow mask deposition, or photolithography and etching. Each chip may contain two or more regions, 127 and 127A, of cathode material as desired.

Figure 12C:
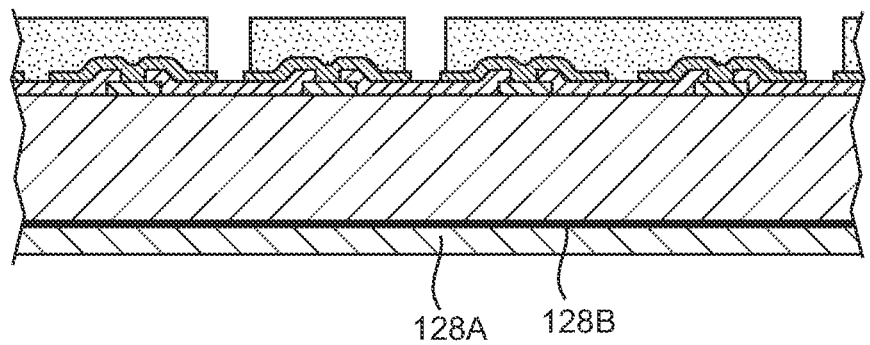

Next anode material 128A is deposited as shown in FIG. 12C. Anode materials of interest include, but are not limited: Mg, Zn, or other electronegative metals. Adhesion layer 128B may be necessary to help anode material to adhere to the silicon. Typical adhesion layers for the anode are Ti, TiW, Cr or similar material. Anode material and the adhesion layer may deposited by physical vapor deposition, electrodeposition or plasma deposition. The cathode may be from about 0.05 to about 500 μm thick, such as from about 5 to about 100 μm thick.

Figure 13A:
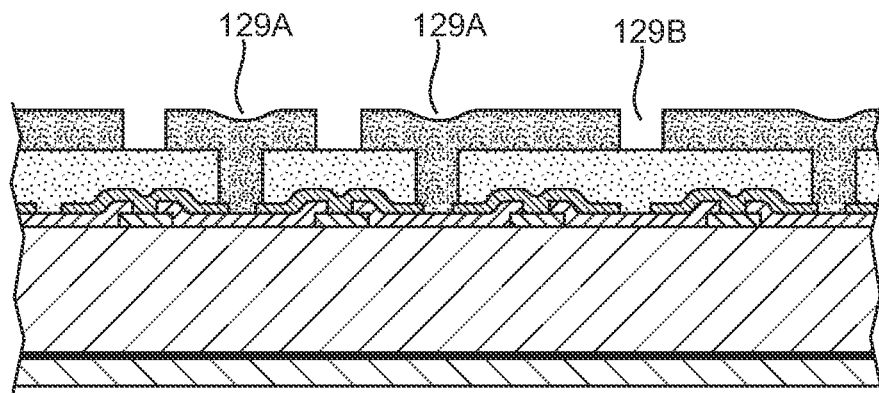

FIG. 13A shows the optional protection layer 129A which is deposited and patterned. In some applications it may be advantageous to control the rate of anode or cathode exposure to the electrolyte environment, so an insulating layer may be deposited and patterned in such a way that it has openings, 129B, of limited size. This way the solution reaches the anode or cathode material at a controlled rate. FIG. 13A illustrates the protection layer on the front (cathode) side of the wafer but it could be also deposited on backside (anode side) of wafer. Typical materials for the protection layer are polyimide, or other photo definable polymer any of which may be spin coated or spray coated. Alternatively a dielectric like $SiO_2$, SiC, or SiN may be deposited by physical vapor deposition or chemical vapor deposition.

Figure 13B:
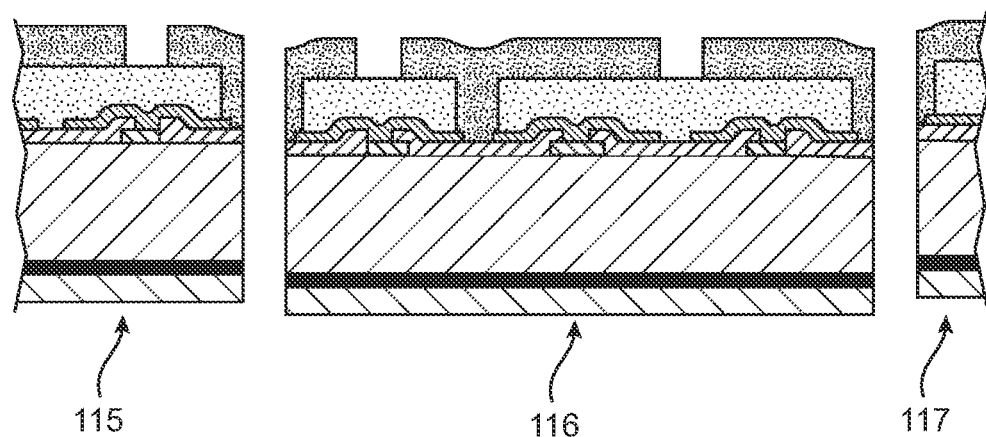

The wafer is then singulated into individual die 115, 116, 117 as shown in FIG. 13B. Dicing can be accomplished by dicing with a diamond blade saw or by reactive ion etching. These are standard silicon semiconductor processing techniques. As reviewed above, the chip dimensions may vary. As such, in certain embodiments, the chip (i.e., identifier) element is dimensioned to have a width ranging from about 0.05 mm to about 1 mm, such as from about 0.1 mm to about 0.2 mm; a length ranging from about 0.05 mm to about 1 mm, such as from about 0.1 mm to about 0.2 mm and a height ranging from about 0.1 mm to about 1 mm, such as from about 0.05 mm to about 0.3 mm, including from about 0.1 mm to about 0.2 mm.

Specific Pill Embodiments

In further describing various embodiments of the compositions of the invention, specific embodiments are now described in greater detail in view of the figures. FIG. 1 provides a diagrammatic, exemplary representation of a pill/capsule embodiment of the present invention, in which the composition is configured as an orally ingestible pharmaceutical formulation in the form of a pill or capsule. The stomach 12 of the patient 10 who ingests the composition 14 is shown. This "smart pill" is shown as it has traveled from the mouth 16 to inside 18 the patient's stomach. Upon reaching the stomach, the pill/capsule undergoes a dissolving process with both the mechanical action of the stomach and the various chemical materials in the stomach fluids, such as hydrochloric acid and other digestive agents.

Figure 2A:
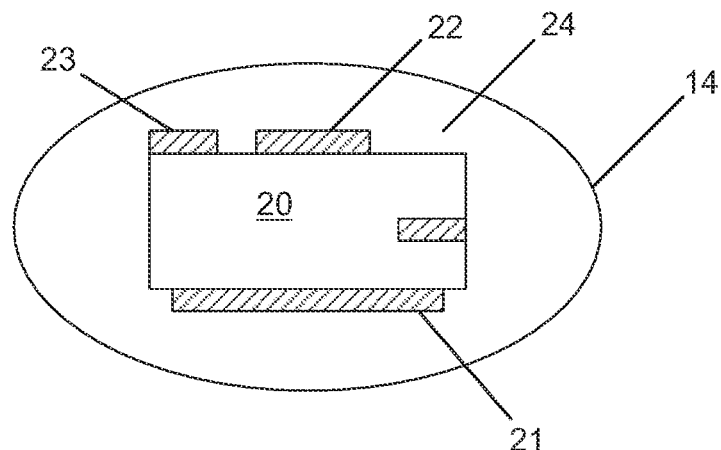
FIGS. 2A and 2B provide a more detailed view of the pill composition shown in FIG. 1
Figure 2B:
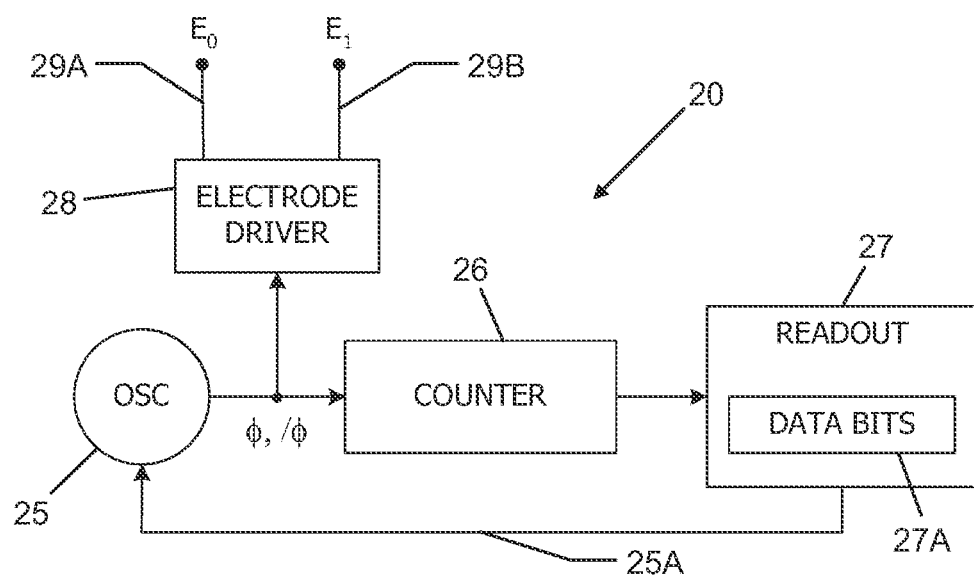

FIGS. 2A and 2B provide a more detailed view of the pill composition shown in FIG. 1. FIG. 2A illustrates an identifier 20 disposed inside a pill 14. Identifier 20 is present as an integrated circuit (IC). The backside (bottom) of circuit 20 is at least partially coated with a first metal 21, and a portion of the front (top) of circuit 20 is coated with a different metal 22, allowing circuit 20 to be powered by reverse electrolysis, e.g., as described above connection with FIG. 4. Also on the top surface are two transmitter electrodes 23, 24.

When pill 14 is fabricated, the integrated circuit 20 is surrounded by at least one external layer that may include pharmacologically active and/or inert materials in any combination. The external layer dissolves in the stomach through a combination of the mechanical action of the stomach and the action of various chemical constituents (e.g., hydrochloric acid) in stomach fluids.

As pill 14 is dissolved, areas of integrated circuit 20 become exposed to the stomach contents, which for present purposes can be regarded as an electrolyte solution. As dissolution of the pill exposes metal layers 21 and 22, power is supplied to circuit 20, which begins to operate and continues to operate until metal layers 21 and 22 or the circuit itself are sufficiently dissolved by digestive processes and acids to become non-functional. Eventually, the remains of the chip are excreted from the body.

In an alternative embodiment, the integrated circuit 20 is attached to, rather than encapsulated in, the pill 14. For instance, circuit 20 might be placed at one end of the pill as the pill is being prepared, in a soluble coating on the surface of the pill, or the like. In embodiments where circuit 20 is wholly or partially exposed, integrated circuit 20 begins to operate sooner after the pill enters the stomach rather than after the pill dissolves.

In one embodiment, circuit 20 transmits a signal identifying pill 14. The identifier may indicate the type (active ingredient(s), brand, etc.) and/or dosage of pill 14 and may also provide a lot number, serial number, or similar identifying information that would allow particular pills to be traced, e.g., as reviewed above.

FIG. 2B is a block diagram of one embodiment of electronic circuit 20. In this embodiment, circuit 20 is a transmitter unit that sequentially transmits a predetermined series of address (identifier) bits using frequency shift keying, with a first oscillation frequency corresponding to bit value 0 and a second oscillation frequency corresponding to bit value 1. As described above, metal layers 21 and 22 supply power to circuit 20. The power (not explicitly shown in FIG. 2B) is supplied to an oscillator 25, a counter 26, a readout circuit 27, and an electrode driver 28 that drives transmitter electrodes 29A, 29B to transmit the signal. Oscillator 25 may be of generally conventional design (e.g., a ring oscillator) and is advantageously configured to operate in the quasi-electrostatic frequency region as described above. Oscillator 25 generates a driving signal ϕ that oscillates between high and low voltage levels and an inverted driving signal /ϕ that is opposite in phase to driving signal ϕ. In one embodiment, oscillator 25 is a voltage-controlled oscillator (VCO) with an oscillation frequency that depends on a control voltage provided on a signal path 25A. Counter 26 counts the oscillations of driving signals ϕ and /ϕ and provides the current count to readout circuit 27. In one embodiment, counter 26 is an eight-bit counter of generally conventional design; other types of counters (including counters with different widths) may also be used. Readout circuit 27 is configured with a set of address (identifier) bits 27A that are advantageously fixed, e.g., at the time circuit 20 is fabricated. As noted above, the bits can be unique to a particular instance of pill 14 or common to a lot of pills fabricated under the same conditions or common to all pills containing a particular pharmacological agent. Address bits 14 can be stored in nonvolatile storage circuits of generally conventional design, and any number of address bits (e.g., 8, 16, 32, 48, etc.) may be provided. Readout circuit 27 generates an oscillator control signal (e.g., a voltage) on line 25A that controls the frequency of VCO 25. In one embodiment, readout circuit 27 is configured to select a current address bit, e.g., based on the current count provided by counter 26, and to generate a control signal on signal line 25A that selects a frequency corresponding to the value of that bit. After some number of cycles (as determined by counter 26), readout circuit 27 selects the next address bit and generates the corresponding control voltage on signal line 25A. Various frequencies may be used to represent the address bit values "1" and "0." In one embodiment, frequencies of 100 kHz and 200 kHz may be used to represent values "0" and "1," respectively. Other values (e.g., 1 MHz and 2 MHz or 1 kHz and 5 kHz) may also be used. The chosen frequencies advantageously are well below the absorption modes of human tissues, which are typically above 400 MHz. As described above, VCO 25 generates complementary signals ϕ, /ϕ that oscillate at a frequency determined by the control signal on signal line 25A. The signals ϕ, /ϕ are used to control an electrode driver 28, which may be implemented, e.g., as shown in FIG. 6D. It should be noted that since electrodes 21 and 22 are in contact with stomach fluids when circuit 20 is operative, the near-field component is coupled directly into the conductive medium of the patient's body and can be detected by a suitably configured data collector, e.g., as described below. In one embodiment, the collector is configured to log the received address (identifier) and the time of receipt. The data collector can also be configured to retransmit this information to an external device, either in real time or while the patient is in a medical facility. It will be appreciated that the transmitter described herein is illustrative and that variations and modifications are possible. For instance, other encoding schemes could be used to transmit the data; in one such embodiment, phase shift keying rather than frequency keying is used. In some embodiments, multiple address bits can be encoded into a single symbol that is transmitted using various keying schemes known in the art.

Figure 3A:
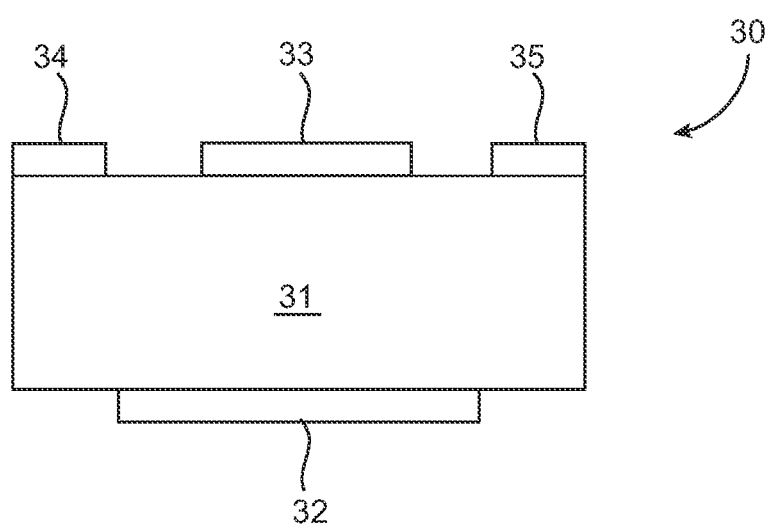
FIGS. 3A to 3E provide views of different embodiments of signal generation elements of the invention.

FIG. 3A provides a detailed depiction of an embodiment of a signal generation element 30 which labels the pharmaceutical material and is encapsulated in the center of the composition. Signal generation element 30 is in the form of IC constructed from a silicon chip where various functional elements, e.g., in the form of one or more layers of circuits, are disposed on a silicon substrate 31. The chip can be fabricated using standard integrated circuit techniques. An example of such a fabrication approach is a 0.5μ CMOS process made available by AMI Semiconductor in Idaho, USA. Shown on the backside of the substrate, the bottom of the chip 31 is metal 1 32 which functions as one battery electrode and on the topside of the chip is metal 2 33 which functions as the other battery electrode. Also on the top side of the chip 31 are electrode 1 34 and electrode 2 35, which constitute a pair of signal-transmission electrodes.

In certain embodiments, electrode 1 34 and electrode 2 35 are fabricated from a material that does not readily corrode in the stomach environment, e.g., they are fabricated from noble metals. Alternatively, in some cases the electrodes can be fabricated of a standard aluminum, such as that available from AMI Semiconductor. The criteria for electrode material selection will be readily ascertainable by the ordinary skilled artisan. That is, if the survival time of the electrode is long enough for detection, it is suitable for use. Standard aluminum metals or other lower cost metals if used for electrodes 1 and 2 (34 and 35) in appropriate applications allow a lower cost for the device. In some cases dissolution of the electrodes, and thus extinction of the reporting signal, can provide a secondary indication of the full dissolution of the pill and incorporated devices.

Metal 1 and metal 2 (32 and 33), in distinction to material selection for the electrode component of the inventive device, are two different metals. Metal 1 and metal 2 are selected so that the potential applied to the silicon is a positive voltage on the top surface and a negative voltage on the bottom surface. In this way the substrate is essentially at the same potential as the cathode, which can be the ground reference for the circuits, and the top surface, with a Sift insulation layer, is coupled to a positive voltage, referenced to that ground on the bottom side.

Figure 3B:
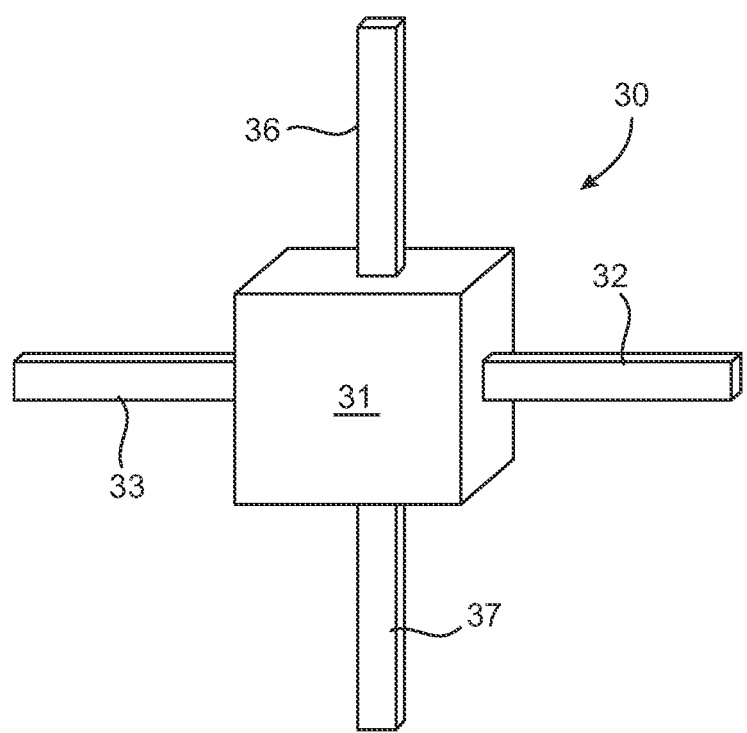
Figure 3C:
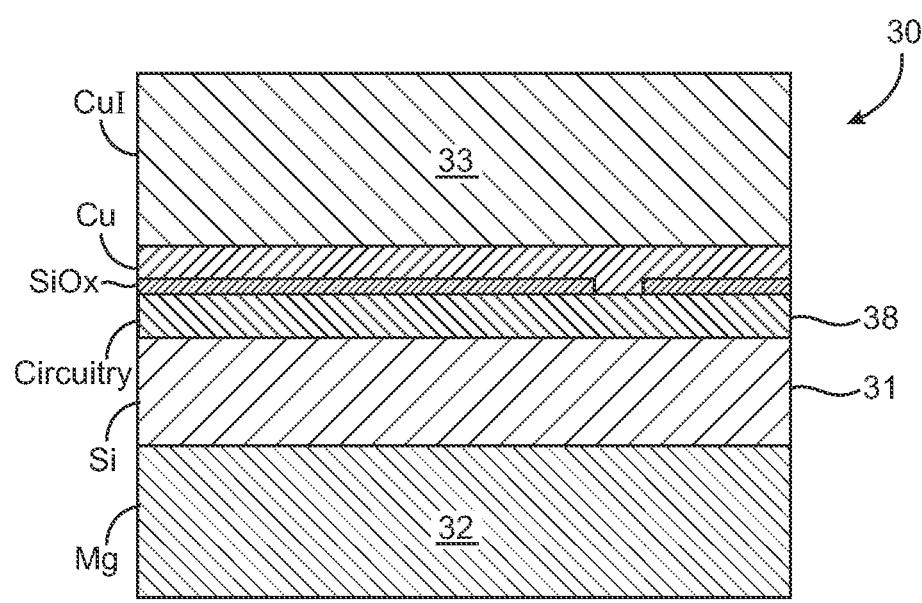

FIG. 3B provides a view of an alternative signal generation element according to an embodiment of the invention. Instead of electrodes, the signal generation element 30 depicted in FIG. 3B includes two antennae 36 and 37 attached to silicon chip 31. Also shown are metals 1 and 2 (32 and 33). The assembly 30 includes circuitry on a silicon chip 31 with either two or four metal structures (32, 33, 36 and 37) attached to it. In embodiments where two different metals are employed, the two metal structures serve as battery metals, that is metal 1 and metal 2 (32 and 33). These metal structures can be provided in a variety of forms. For instance, in one embodiment, metal 1 and metal 2 are very thick plated elements on the surface of the chip, front and back (e.g., as shown in FIG. 3C described below). In another embodiment, metal 1 and metal 2 are relatively long wires that are simply bonded to the chip at some point, e.g., as shown in FIG. 3B. Metal 1 and metal 2 in some cases are insulated. In this case, the erosion occurs at the tip and then propagates towards the chip 31. The erosion as it dissolves in the solution starts at the end of the wire and gradually work its way toward the chip 31. This configuration improves battery life. In another configuration, a metal is plated up on the front and back of the chip, and then the surface disappears. The two wires can also be employed as antennae. In one configuration, a perpendicular pair of antennae (36 and 37) is provided. In this implementation, there would be two other metal structures which are typically of the same material. This material can be selected from a variety of metals, such as platinum or gold. These metal structures are attached to the chip and extend some dimension away from the chip. Typically these structures are on the order of a millimeter to a centimeter combined length. In some configurations, a significant portion of the metal structures are insulated so that the dipole created is of maximum dimension. In other configurations, just the battery metals perform that dipole function, e.g., as described below in connection with FIG. 3C, or a separate antenna is provided.

In certain embodiments, the signal generation element does not include antennae and instead uses battery components as antennae, such as shown in FIG. 3C. In FIG. 3C, signal generation element 30 includes silicon support layer 31 positioned between metal 1 layer 32 and metal 2 layer 33. Also shown is circuitry layer 38. In such embodiments, when a switch on the chip, e.g., in the circuitry layer, is closed, a current is produced between the two metals of the battery, which is then detected. In certain embodiments, a membrane larger then chip which defines a path for the current to travel is provided.

Figure 3D:
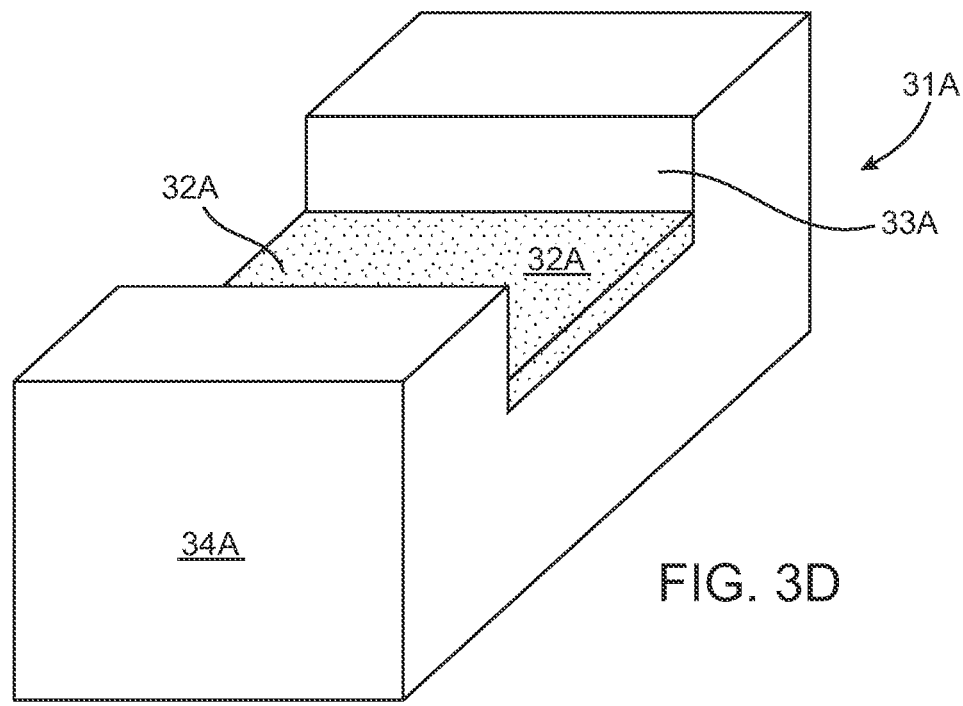
Figure 3E:
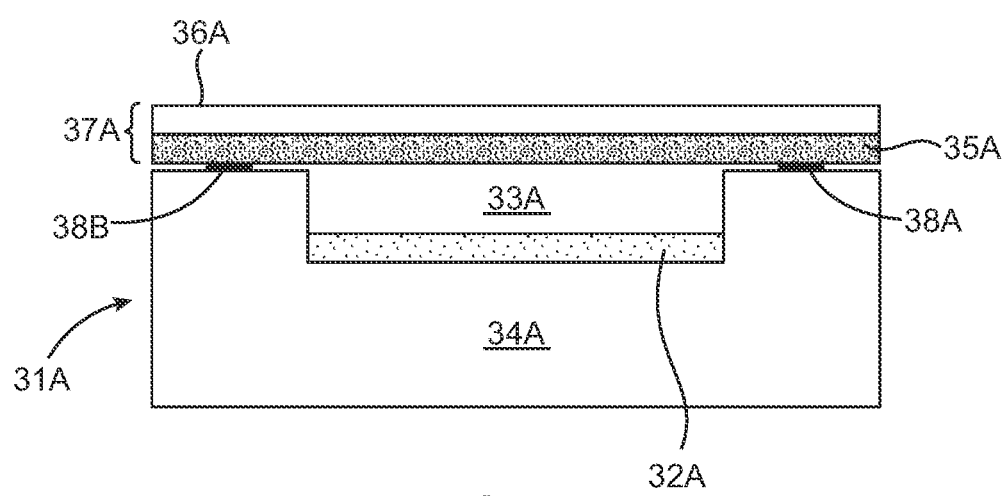

Yet another embodiment of a battery which is activated upon contact with a physiological fluid is shown in FIGS. 3D and 3E. In the structure shown in these figures, the battery comprises top and bottom portions each supporting an electrode, where the top and bottom portions can be brought together to produce a structure comprising a volume bounded by opposing first and second electrodes, where the volume may be filled with an electrolyte, e.g., physiological fluid, when active. FIG. 3D provides a representation of a bottom portion 31A of the battery in which material 1 32A is deposited into a recessed chamber 33A on top of a substrate (e.g., silicon chip) 34A. Recessed chamber 33A has one or more ends open to allow electrolyte to enter. Material 2 35A is deposited on a separate substrate 36A to produce a second portion 37A, which is then bonded, e.g. by bonds 38A and 38B, to the chip in a "flip chip" type process. All processing can be done at the wafer scale. Where desired, the openings of the recessed chamber are filled with a degradable material, e.g., with a polymer, to control how quickly the battery is activated. Substrates 34A and 36A for materials 34A and 35A can be silicon, metal, or polymer/plastic. In certain embodiments, the structure shown in FIGS. 3D and 3E is a battery where the first electrode is deposited into a recessed chamber on the top of the chip. The recessed space has one or two open ends to allow electrolyte flow. The second electrode is deposited on a separate substrate (e.g. a silicon wafer, a metal film or a polymer film), then bonded on top of the wafer with the chips on it in a "flip-chip" type process. The processing is done at a wafer scale and the cells diced as usual. The advantages of this configuration include: protection of the electrode surfaces from being blocked by components present in the stomach or the stomach lining itself; prevention of contact between any species generated on the battery (e.g., Cu) and the stomach lining that could have toxicity risks; 3) provision of uniform consumption of electrode materials across the electrode surface and more uniform current distribution between the electrodes.

FIG. 4 provides a diagrammatic representation of the events which occur when the pill is ingested and dissolved to the point that some of the pill has been chemically and/or physically eroded away. Metal 1 and metal 2 (32 and 33) are now in an ionic solution 39. This creates a low voltage (V−) and a high voltage (V+) as applied to an electronic circuit 40. The two outputs of that electronic circuit 40 are E0 41 and E1 42, which are the signal-transmission electrodes on the top surface. In an alternate embodiment no shown in FIG. 4 where the signal generation element 30 includes a single electrode, the output is E0 41.

Figure 5:
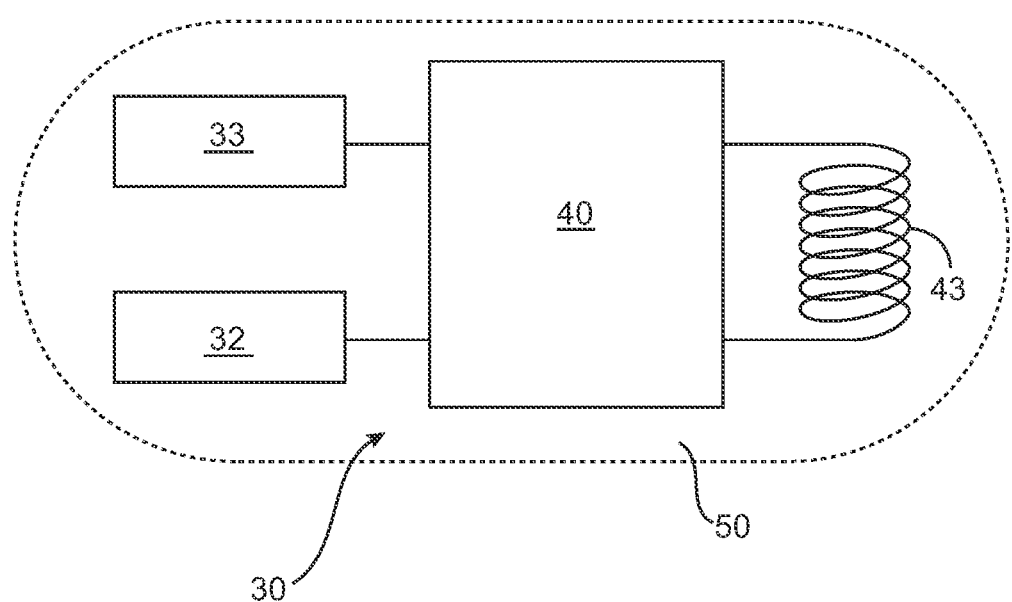
FIG. 5 provides a similar arrangement to FIG. 4, with a coil rather than two electrodes as the output.

FIG. 5 shows a similar arrangement as in FIG. 4. However, instead of having two electrodes as the output, a coil is provided. Metal 1 and metal 2 (32 and 33) are applied to the electronic circuit 40 of signal generation element 30. The outputs of the electronic circuit 40 are coupled to a coil 43. This configuration provides that a battery is created by metal 1 and metal 2 (32 and 33) when exposed to ionic solution. This battery drives the circuit 40, which creates an oscillating frequency. This oscillating current goes through the coil and generates a RF magnetic signal. Unlike near-field quasi-static electrical signals, which may suffer from significant attenuation through body tissues, the RF magnetic signal can be transmitted through body tissues with less attenuation. The RF magnetic signal is then picked up by an external or internal receiver device that has a magnetic-signal detection mechanism. If a broadcast is provided at a high enough frequency, a pager-like device that is worn by the patient will detect whenever a pill is ingested.

Figure 6B:
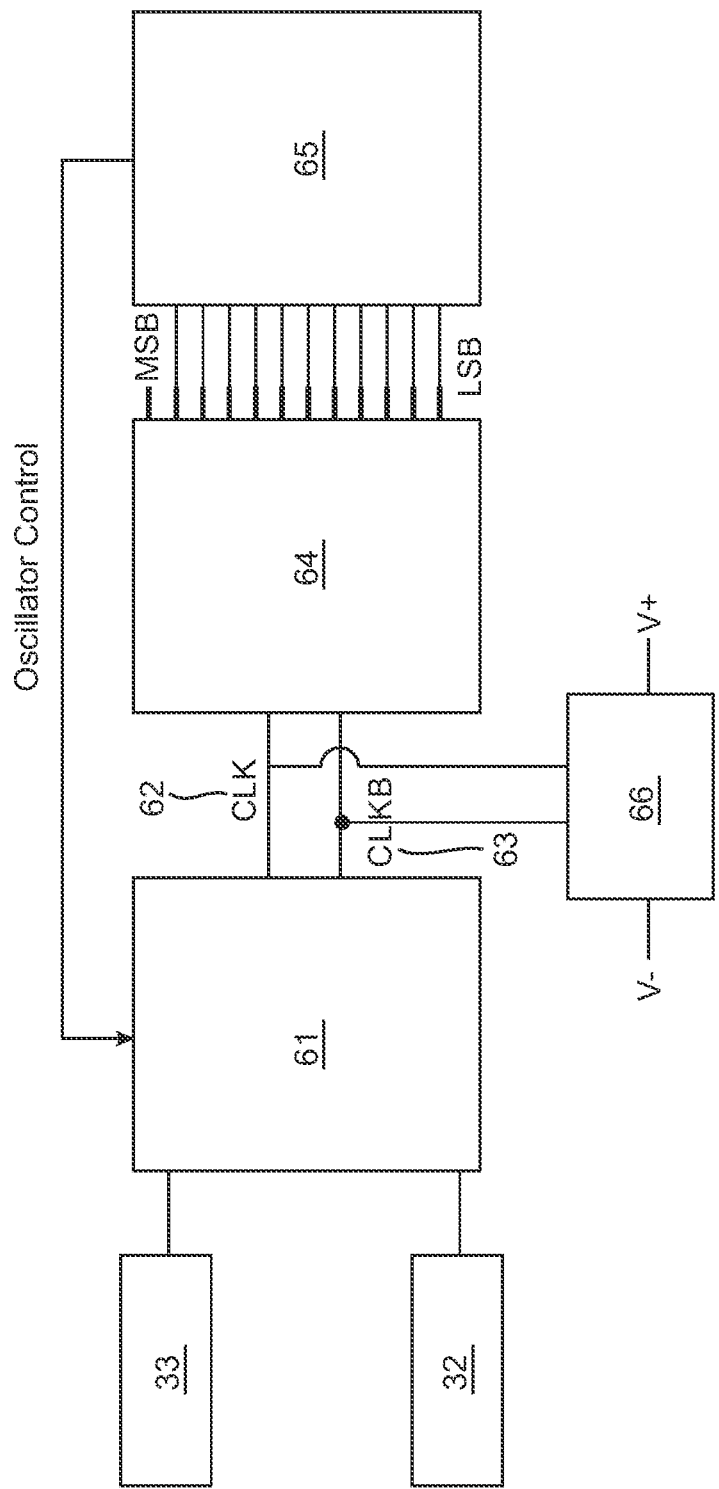
Figure 6C:
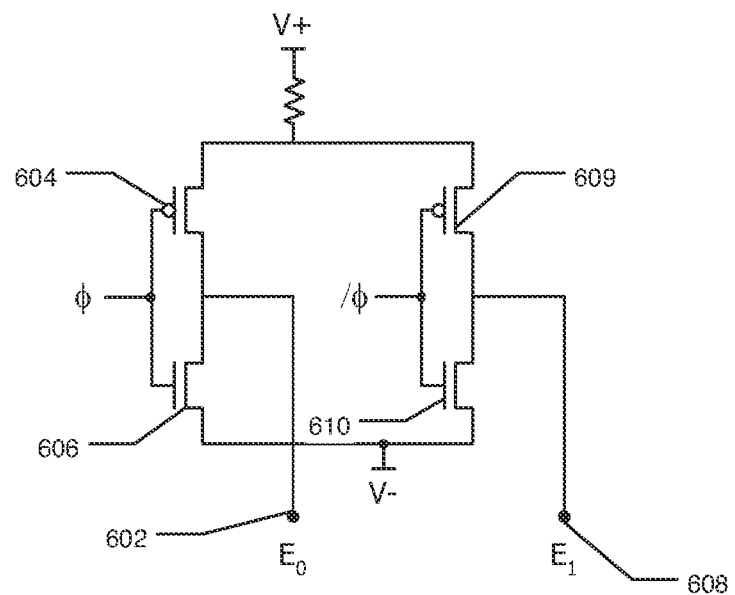
Figure 6D:
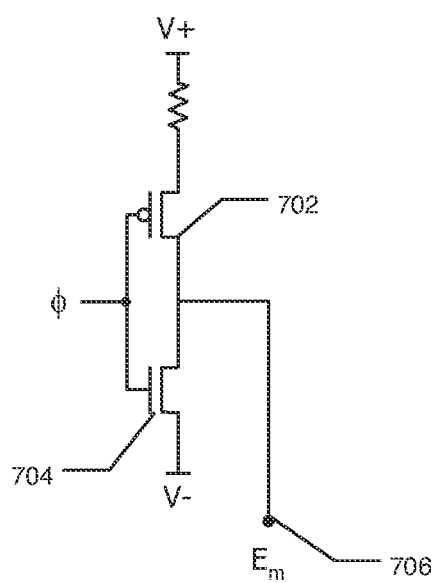

FIG. 6B shows the detail of one implementation of an electronic circuit that can be employed in a signal generation element. On the left side are the two battery electrodes, metal 1 and metal 2 (32 and 33). These metals, when in contract with an electrolyte, form a battery and provide power to an oscillator 61, in this case shown as a schematic. The metal 1 32 provides a low voltage, (ground) to the oscillator 61. Metal 2 33 provides a high voltage ($V_{high}$) to the oscillator 61. As the oscillator 61 becomes operative, it generates a clock signal 62 and an inverted clock signal 63, which are opposites of each other. These two clock signals go into the counter 64 which simply counts the number of clock cycles and stores the count in a number of registers. In the example shown here, an 8 bit counter is employed. Thus, the output of counter 64 begins with a value of "00000000," changes to "00000001" at the first clock cycle, and continues up to "11111111." The 8-bit output of counter 64 is coupled to the input of an address multiplexer (mux) 65. In one embodiment, mux 65 contains an address interpreter, which can be hard-wired in the circuit, and generates a control voltage to control the oscillator 61. Mux 65 uses the output of counter 64 to reproduce the address in a serial bit stream, which is further fed to the signal-transmission driving circuit. Mux 65 can also be used to control the duty-cycle of the signal transmission.

In one embodiment, mux 65 turns on signal transmission only one sixteenth of the time, using the clock counts generated by counter 64. Such a low duty cycle conserves power and also allows other devices to transmit without jamming their signals. The address of a given chip can be 8 bits, 16 bits or 32 bits. Typically, more than 8 bits will be used in a product because there are so many different types of pharmaceuticals. Each pharmaceutical will have its own specific address.

The present invention also allows the possibility that, where appropriate, each pharmaceutical batch can be provided with a batch specific address. This allows identification of where the pill was made, when the pill was made, and in what batch it was made. In some cases, each pill will have a unique identifier. This would be particularly useful when drugs are more likely to be subsequently stolen or used illicitly, and thus should be tracked, or where questions of contamination may arise.

According to one embodiment, mux 65 produces a control voltage, which encodes the address serially and is used to vary the output frequency of oscillator 61. By example, when the control voltage is low, that is, when the serial address bit is at a 0, a 1 megahertz signal is generated by the oscillator. When the control voltage is high, that is, when the address bit is a 1, a 2 megahertz signal is generated the oscillator. Alternately, this can be 10 megahertz and 20 megahertz, or a phase shift keying approach where the device is limited to modulating the phase. The purpose of mux 65 is to control the frequency of the oscillator or an AC alternative embodiment of the amplified signal of oscillation.

The outputs of mux 65 are coupled to electrode drive 66 which can drive the electrodes to impose a differential potential to the solution, drive an oscillating current through a coil to generate a magnetic signal, or drive a single electrode to push or pull charge to or from the solution.

In this manner, the device broadcasts the sequence of 0's and 1's which constitute the address stored in mux 65. That address would be broadcast repeatedly, and would continue broadcasting until metal 1 or metal 2 (32 and 33) is consumed and dissolved in the solution, when the battery no longer operates.

Figure 7:
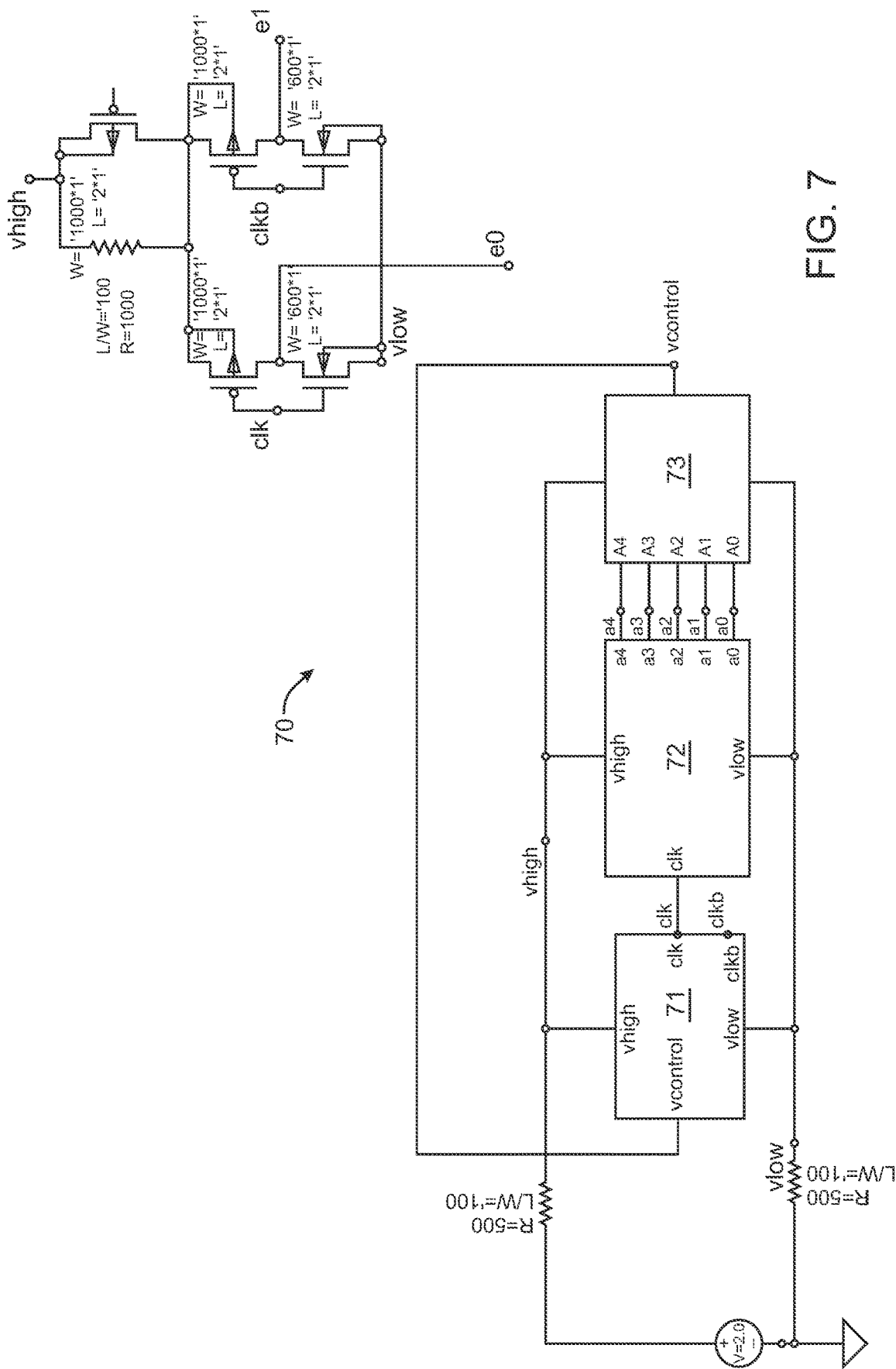
FIG. 7 provides an oscillator and a counter implementation according to an embodiment of the invention.

FIG. 7 is an alternate embodiment of the present invention. This implementation of the circuit 70 shows the oscillator 71 and a counter 72. The mux 73 takes 5 bits from counter 72 as its input. On the upper right corner of FIG. 7 is an exemplary circuit diagram for the signal-transmission electrode driver. Two CMOS invertors respectively take the clock and inverted clock signals as their inputs, and drives electrodes e0 and e1.

Figure 8:
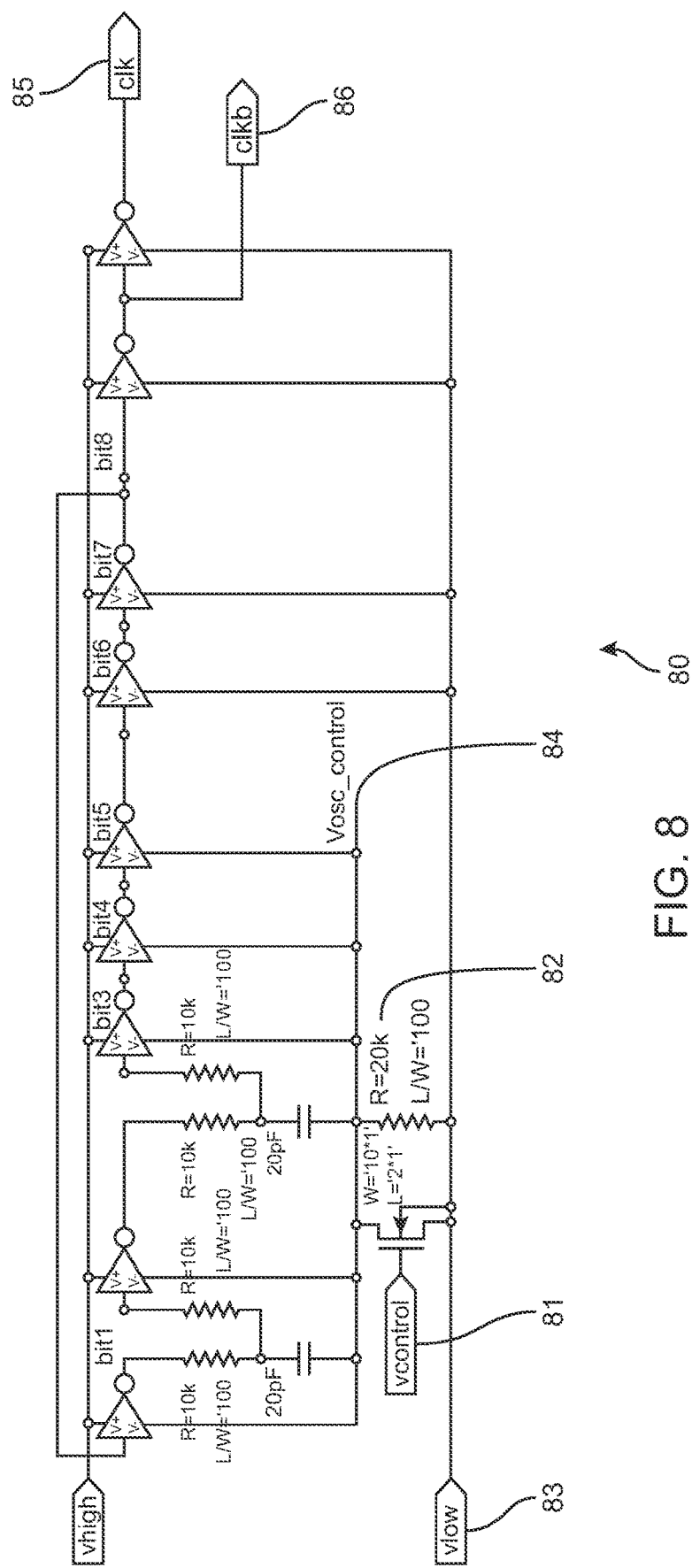
FIG. 8 is an additional embodiment of an oscillator where V control modulates the amount of voltage driving the oscillator.

FIG. 8 provides one implementation of an oscillator 80. In this case, $V_{control}$ 81 basically controls the amount of voltage driving the oscillator 80. When $V_{control}$ is low, a 20,000 ohm resistor 82 separates Vow 83, which is the low power-supply voltage, and the oscillator control line, $V_{osc}$ control 84. When $V_{control}$ is high, the $V_{osc}$ control goes to Vow, putting the maximum voltage across the oscillator circuitry and resulting in a higher frequency coming out of the clock signal and the inverted clock signal (85 and 86).

Figure 9:
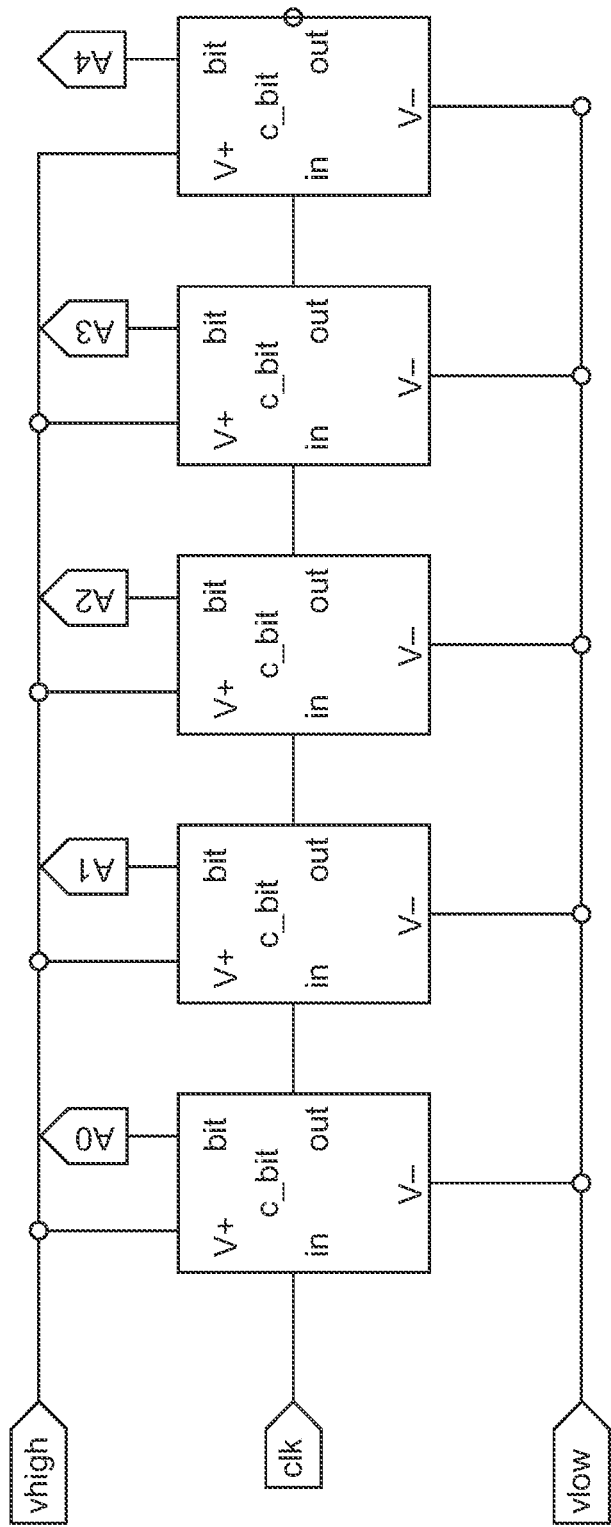
FIG. 9 is an additional embodiment with a simple trickle or asynchronous counter.

FIG. 9 shows a simple trickle or asynchronous counter which has in this case four flip flops with some simple inverters that simply count all the way up and then start over again back to zero, and start counting all the way up again. In one embodiment, a multiplexer can take AO and A1, A2, A3, as its address inputs and can compare these inputs with a stored address, and then have the stored address output as the oscillator control signal.

Figure 10:
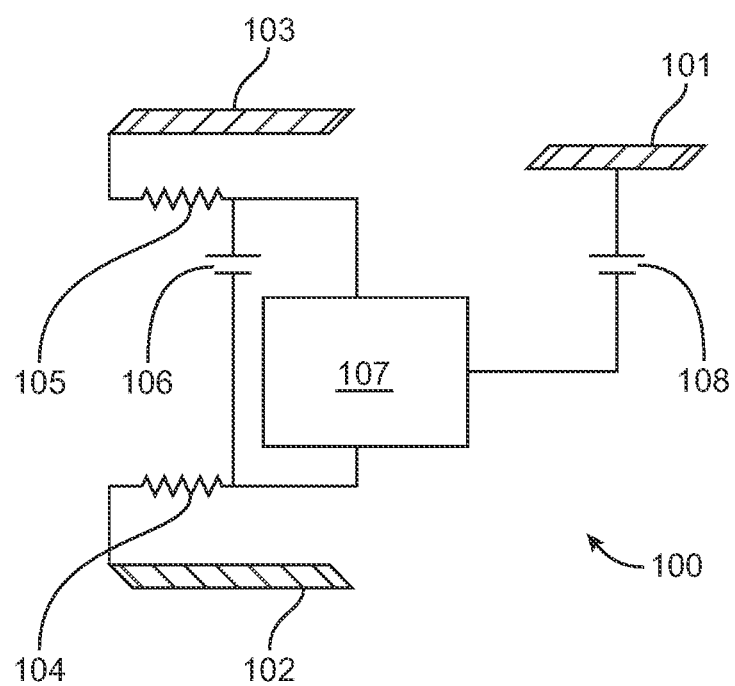
FIG. 10 provides a schematic representation of a three terminal, monopole signal generation element according to an embodiment of the invention.

As indicated above, in certain embodiments the signal generation element may include a single electrode, and therefore have a monopole configuration. In one embodiment of the present invention, as shown in FIG. 10, a three terminal, monopole signal generation element 100 is provided. In this embodiment, the signal generation element 100 of the pill has one electrode 101 which is capacitively coupled to chip 107. Two metal electrodes 103 and 102 constitute the electrodes for the battery, which provides power for the signal generation element 100. Electrodes 102 and 103 are coupled to the chip 107 through two resistors 104 and 105, and an optional storage capacitor 106. In one embodiment, electrode 102 is the ground and electrode 103 provides $V_{high}$ for the signal generation element. Electrode 101 is the output of the mono pole signal generation element. During operation, electrode 101 will push current into and out of body's fluid at a high frequency. A receiver will detect the pushing and pulling of that charge out of the body's fluids. Note that the biggest difference between this configuration and the configuration described previously is that this configuration provides a mono pole. When chip 107's output changes, capacitor 108 forces the potential on electrode 101 to change instantly, which result a corresponding change in the potential of the body. A receiver that is in contact of the body can thereby detect a large transient voltage change.

This inventive design produces an alternating current into and out of the body which is detected by a receiver (not shown). The output coupling capacitors may be optional. However, the presence of these capacitors prevents any DC currents and forces an AC signal.

Figure 14:
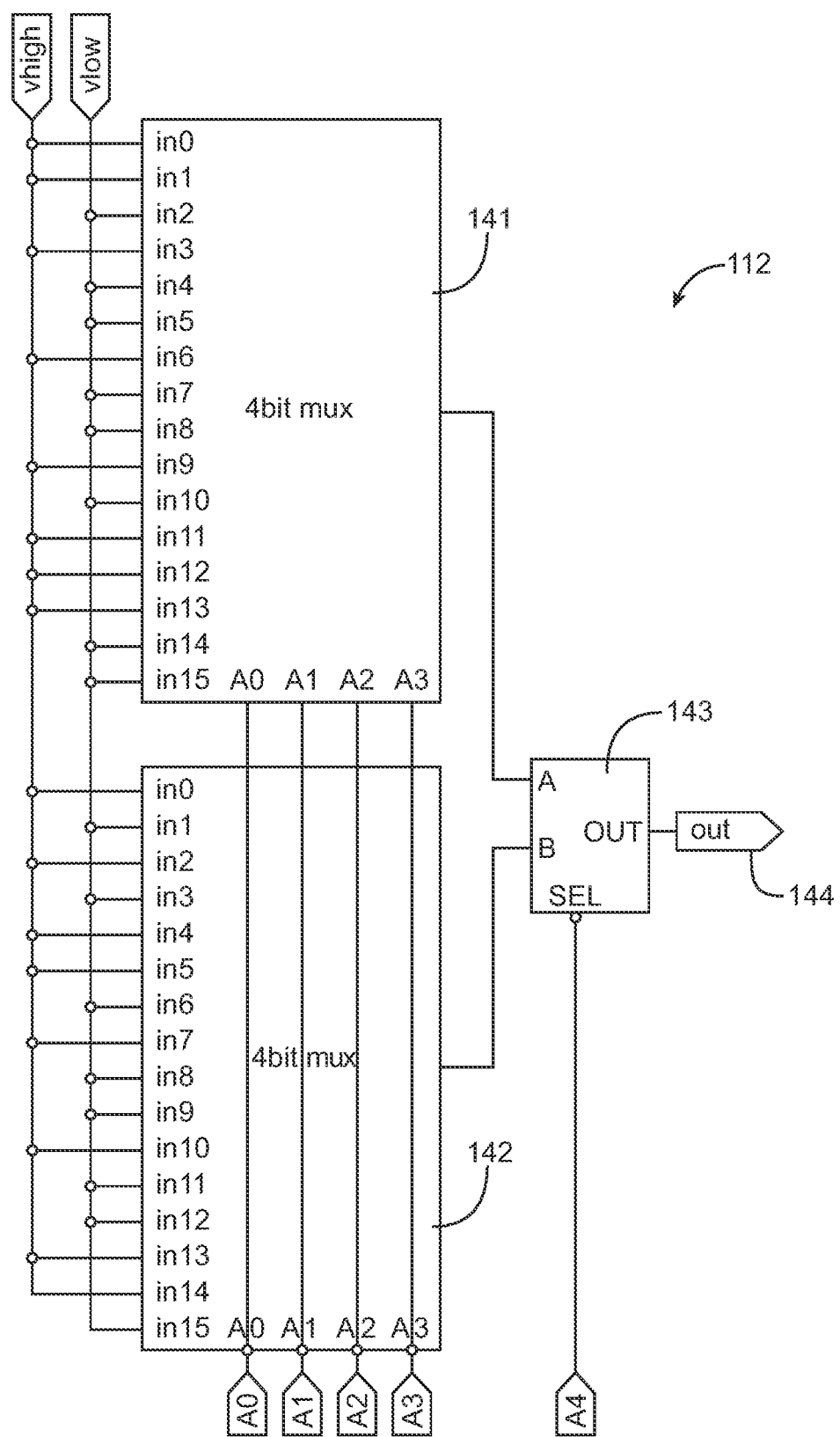
FIG. 14 shows the multiplexer and the addressing system.

FIG. 14 shows the multiplexer and the addressing system 73 of the circuitry of the signal generation element of FIG. 7. In this case, there are two 4 bit muxes (141 and 142) and a 1 bit mux 143, wherein the 1 bit mux 143 takes the outputs of the two 4 bit muxes 141 and 142 as its input. Each input port of muxes 141 and 142 is coupled to either the high voltage $V_{high}$ or the low voltage $V_{low}$. This configuration of the present invention will allow for a 32 bit number, which is hard-wired to the 32 inputs of the two muxes, to be converted to a multiplexed serial output 144. As the counter goes through the 5 bits of counting, the output of mux 144 sequentially selects the inputs of muxes 141 and 142. When the 5 bit counter reaches "11111," the sequence will start over from the beginning again. This way the 16 bit address is repeatedly sent. An alternative approach is to send 16 bits of zeros and 16 bits of address alternatively, so that the receiving circuitry can be waken up and synchronized.

Figure 15:
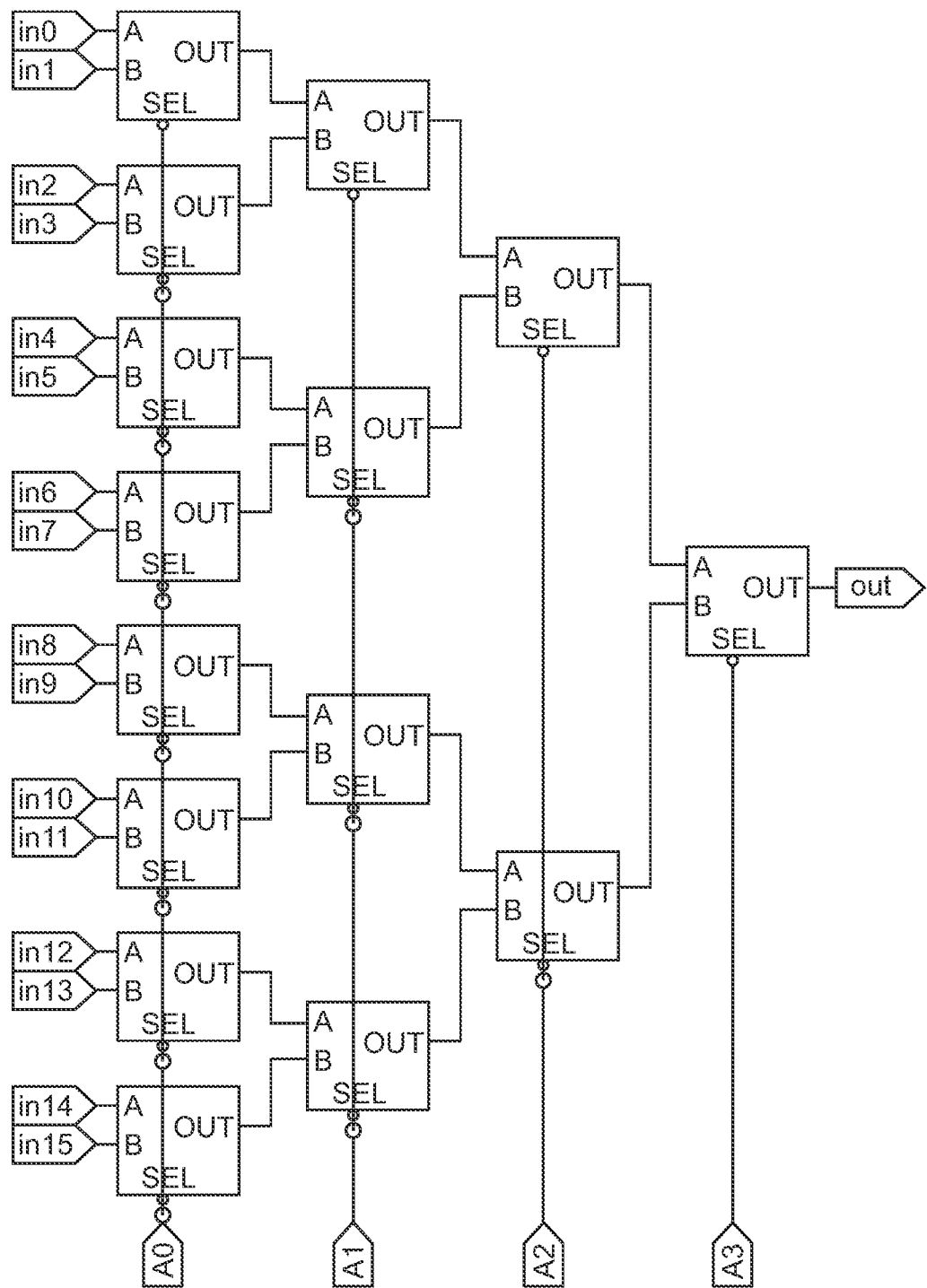
FIG. 15 shows a detail of the 4 bit mux of the system shown in FIG. 14.

FIG. 15 shows a detail of the 4 bit mux 141 of the system shown in FIG. 14. The 4 bit mux is constructed from 4 levels of 1 bit muxes.

Figure 16:
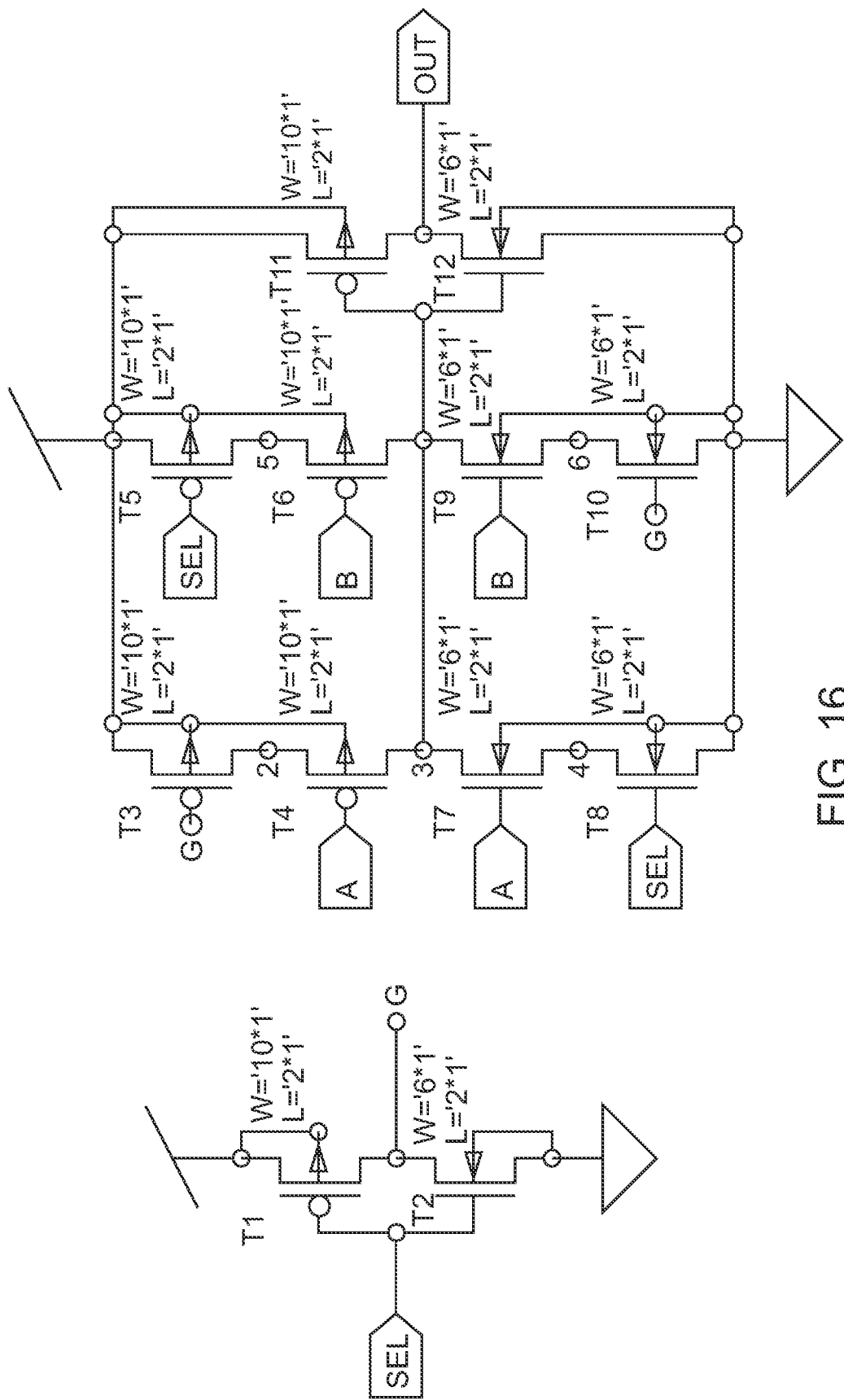
FIG. 16 shows the 1 bit mux in detail that makes up the 4 bit mux.

FIG. 16 shows the 1 bit mux in detail that makes up the 4 bit mux 141.

Figure 17:
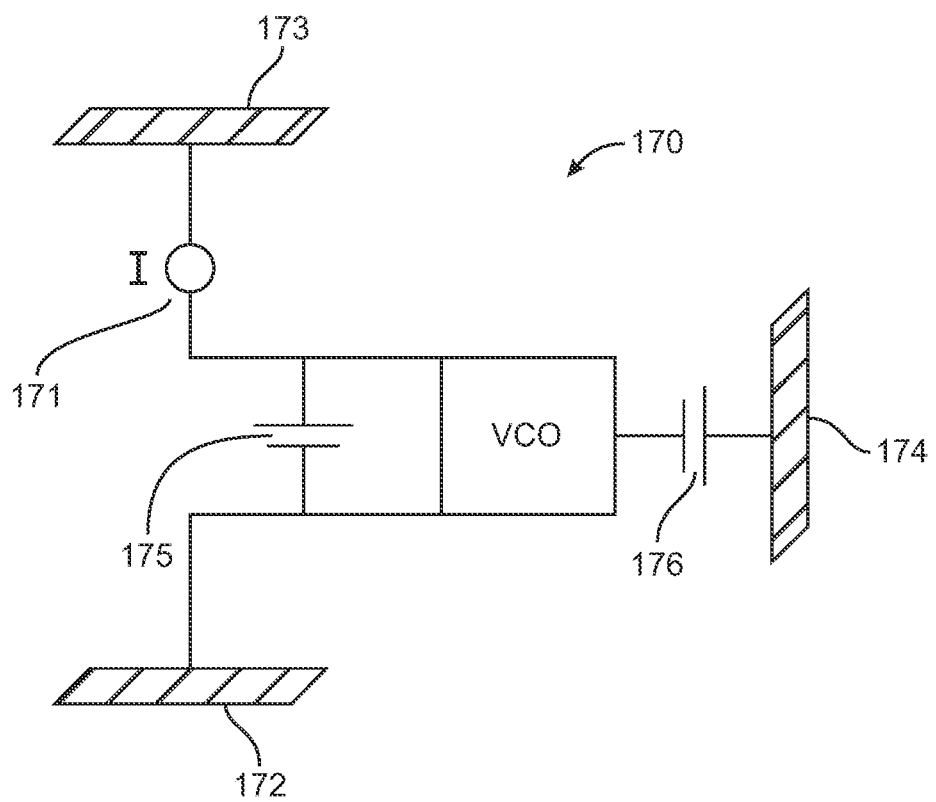
FIG. 17 is an additional monopole embodiment of a signal generation element.

FIG. 17 is an additional mono pole embodiment 170 of a signal generation element. The biggest difference from the prior described embodiments is that a current source 171 is placed in series with the power supply created by M1 172 and M2 173. This creates a DC current between M1 172 and M2 173. This DC current does not compete with the AC signal generated by the electrode 174. This DC current will then go to one or another capacitor (175 and 176) and would either charge up the electrode or charge up another capacitor. The concept behind this embodiment is to have a DC current created between M1 and M2 and an AC signal generated at the single electrode. Coupling capacitor 176 is optional.

Figure 18A:
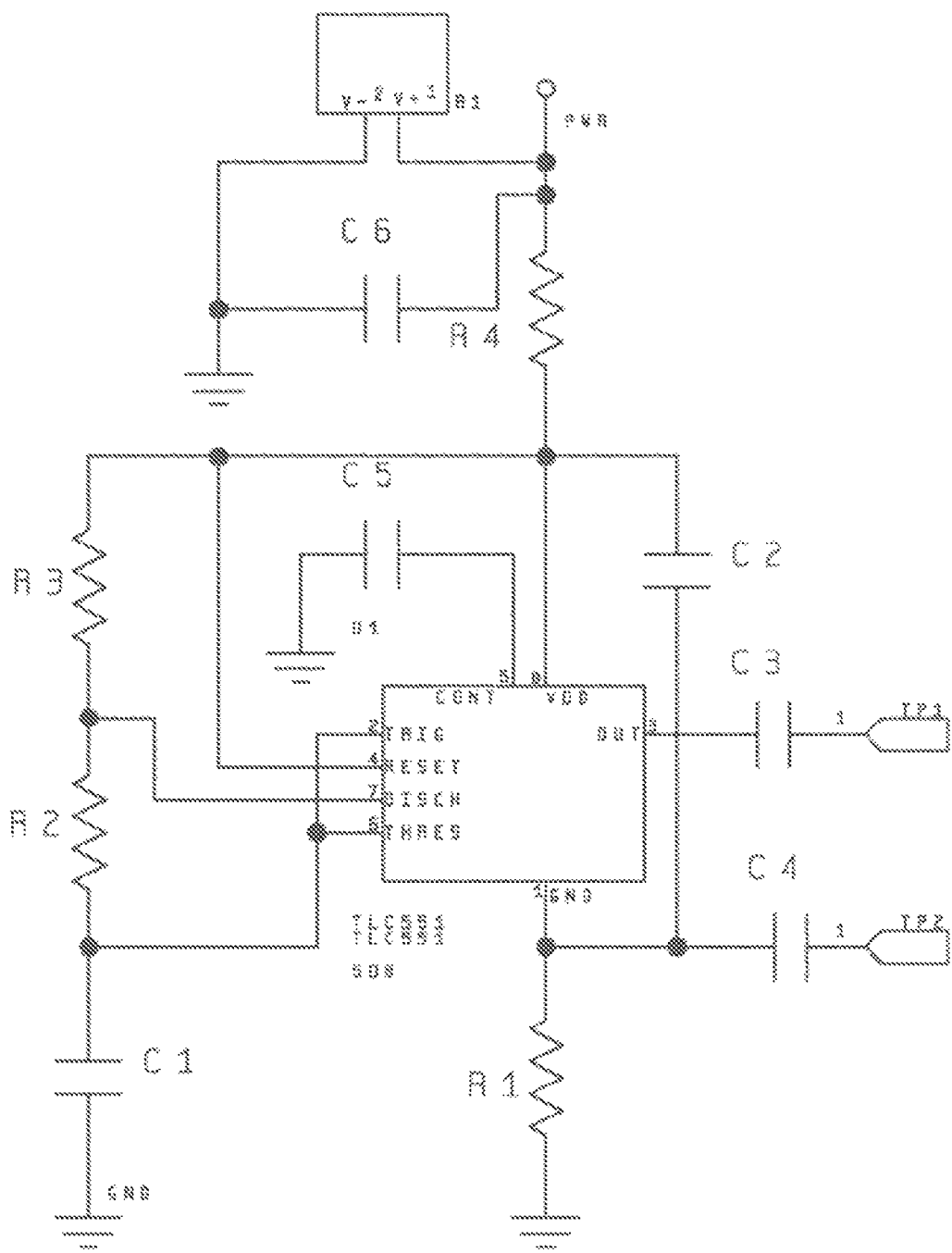
FIG. 18A is an exemplary schematic diagram of a signal-transmission driver circuit that transmits a signal at a fixed frequency, in accordance with one embodiment of the present invention.

FIG. 18A is an exemplary schematic diagram of a signal-transmission driver circuit. This circuit is based on an 8-pin 555 timer chip. As is shown on FIG. 18A, the pin designations of the 555 timer chip are as follows: pin 1 is the ground; pin 2 is the trigger, pin 3 is the output, pin 4 is reset, pin 5 is the control voltage, pin 6 is the threshold, pin 7 is discharge, and pin 8 is the power supply to the chip $V_{dd}$. The output pin and the ground pin are capacitively coupled to two transmission electrodes, respectively. During operation, this circuit transmits a signal at a fixed frequency.

FIG. 18B1 to 18B2 is an exemplary schematic diagram of a receiver circuit. Shown on the upper left portion of the diagram is a front-end amplification stage, which receives the signal through a pair of electrodes and performs differential amplification to the signal using an instrumentation amplifier. In the middle portion of the diagram is a cascaded four-stage filter. In one embodiment, the first two stages are high-pass filters with a cut-off frequency higher than 1 KHz, such as a cut-off frequency at approximately 10 KHz. The high-pass filter removes the low-frequency noises and interferences, such as the 60 Hz power-line noise. The last two stages are low-pass filters with a cut-off frequency lower than 500 KHz, such as a cut-off frequency at approximately 200 KHz. The low-pass filters can remove high-frequency noises and interferences. The filtered and amplified signal is fed to an LED, as is shown on the lower left portion of the diagram. When a signal is detected, the LED is lit indicating presence of the signal.

The device described above generally includes two circuits: one is a logic circuit that generates the address bit sequence, and one is a driver circuit that drives the transmission electrodes based on the address bit sequence. The power-consumption characteristics of these two circuits are different. Typically, the logic circuit requires a high voltage power supply, e.g., a 1.2 V power supply, to switch the CMOS circuits. However, the current drawn through the logic circuit is relatively small. For example, in one embodiment, the current drawn through the logic circuits is approximately 5 µA.

On the other hand, the driver circuit may draw a much larger current, because of the power it requires to transmit a sufficiently detectable signal. Consequently, the voltage of the power supply can be pulled down to a lower level. For example, the driver circuit can draw 100 µA and pull the battery voltage down to 0.5 V.

Because the area of the battery electrodes can be limited due to the size constraint of the device, the interference between the two circuits with regard to power supply may be significant. As a result, the driver circuit could pull the battery voltage down to a point that makes the logic circuit inoperable. One embodiment of the present invention uses a split battery configuration to decouple the power supplies for the logic and driver circuits.

Figure 19:
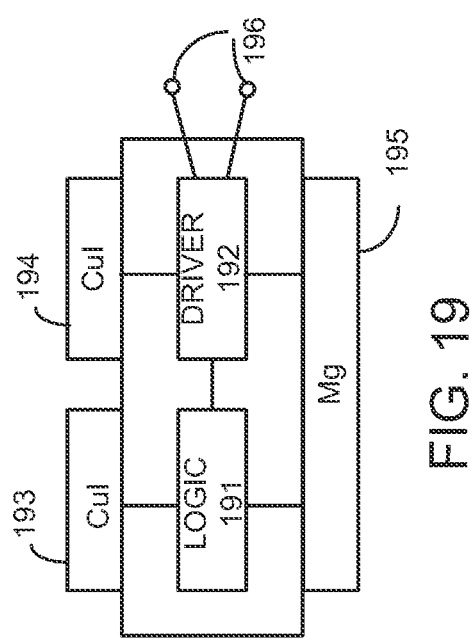
FIG. 19 shows one exemplary split (i.e., segmented) battery design, in accordance with one embodiment of the present invention.

FIG. 19 shows one exemplary split (i.e., segmented) battery design. Two battery electrodes 193 and 194, which are made from copper iodine, constitute the battery anodes for the logic circuit 191 and driver circuit 192, respectively. Effectively, electrodes 193 and 194 form two separate batteries with a shared common magnesium cathode 195. In this way, the driver circuit 192 can draw sufficient current to drive transmission electrodes 196 without significantly impairing the power supply for the logic circuit 191.

Figure 20:
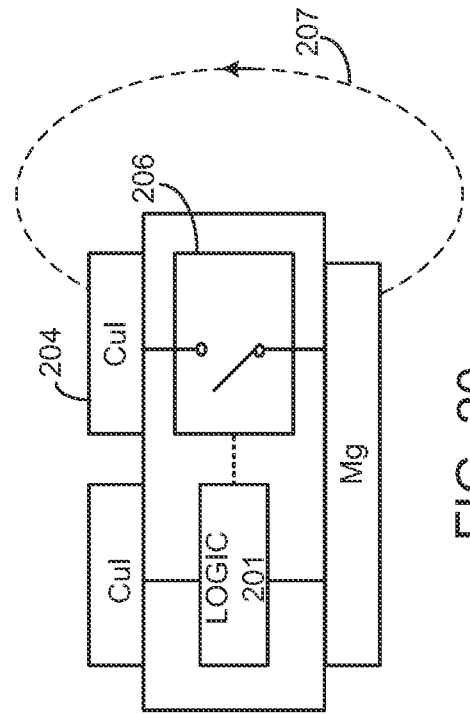
FIG. 20 shows one exemplary design of the driver circuit that uses split battery electrodes for transmission, in accordance with one embodiment of the present invention.

During operation, driver circuit 192 draws a current from the battery formed by electrodes 194 and 195, and pushes this current through transmission electrodes 196 into the body. In a further embodiment, the device can avoid the use of separate transmission electrodes by using the battery electrodes for transmission. FIG. 20 shows such a configuration. The driver circuit 206 essentially contains a switch coupled between the anode 204 and the cathode. This switch can be turned on or off by the address signal from the logic circuit 201. When the switch is turned on, the battery for the driver circuit is effectively short-circuited within the chip. Consequently, a current 207 flows through the body from the cathode to anode 204. The resistance of the body tissue can thereby generate a voltage difference, which can be readily detected by, for example, a differential amplifier.

Figure 21:
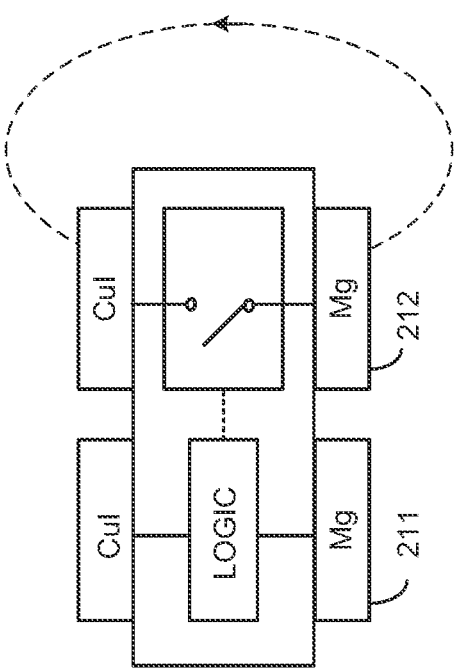
FIG. 21 shows one exemplary split battery design with a split cathode, in accordance with one embodiment of the present invention.

In some cases, the size of the cathode could be limited, resulting in coupling between the power supplies for the logic and driver circuits even with split anodes. According to one embodiment, as is shown in FIG. 21, the cathode can also be split to further decouple the two power supplies. Here, two separate magnesium electrodes 211 and 212 serve as separate cathodes for the two batteries respectively serving the logic and driver circuits. The coupling between the two circuits can thus be minimized.

Figure 22:
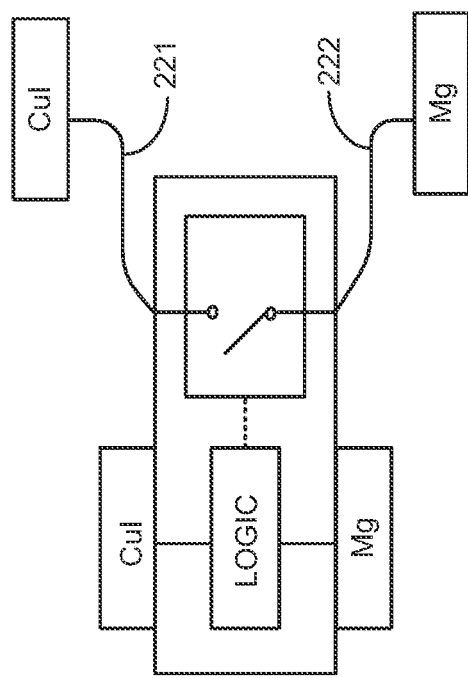
FIG. 22 shows one exemplary design where the battery electrodes for the driver circuit are coupled to the driver circuit via two external wires, in accordance with one embodiment of the present invention.

In a further embodiment, the battery electrodes for the driver circuit can be detached from the chip and coupled to the driver circuit through two external wires, as is shown in FIG. 22. The battery electrodes for the logic circuit, on the other hand, can still be deposited on the chip to provide high-voltage power supply to the logic circuit. The external wires 221 and 222, which can be approximately 1 cm long each, form a long dipole and can provide attendant signal amplification. As a result, the effectiveness of the transmission is not limited by the size of the chip. In one embodiment, the wires are initially folded within a pill and can unfold when the pill is digested.

Methods of Making Compositions

A variety of manufacturing protocols may be employed to produce compositions according to the invention. In manufacturing the subject compositions, a signal generation element is stably associated with the pharmaceutical dosage from in some manner. By stably associated is meant that the signal generation element and the dosage form to do separate from each other, at least until administered to the subject in need thereof, e.g., by ingestion. The signal generation element may be stably associated with the pharmaceutical carrier/active agent component of the composition in a number of different ways. In certain embodiments, where the carrier/active agent component is a solid structure, e.g., such as a tablet or pill, the carrier/active agent component is produced in a manner that provides a cavity for the signal generation element. The signal generation element is then placed into the cavity and the cavity sealed, e.g., with a biocompatible material, to produce the final composition. For example, in certain embodiments a tablet is produced with a die that includes a feature which produces a cavity in the resultant compressed tablet. The signal generation element is placed into the cavity and the cavity sealed to produce the final tablet. In a variation of this embodiment, the tablet is compressed with a removable element, e.g., in the shape of a rod or other convenient shape. The removable element is then removed to produce a cavity in the tablet. The signal generation element is placed into the cavity and the cavity sealed to produce the final tablet. In another variation of this embodiment, a tablet without any cavity is first produced and then a cavity is produced in the tablet, e.g., by laser drilling. The signal generation element is placed into the cavity and the cavity sealed to produce the final tablet. In yet other embodiments, a tablet is produced by combining the signal generation element with subparts of the tablet, where the subparts may be pre-made subparts or manufactured sequentially. For example, in certain embodiments tablets are produced by first making a bottom half of the tablet, placing the signal generation element on a location of the bottom half of the tablet, and then placing top portion of the tablet over the bottom half and signal generation element to produce the final desired composition. In certain embodiments, a tablet is produced around a signal generation element such that the signal generation element is located inside of the produced tablet. For example, a signal generation element, which may or may not be encapsulated in a biocompatible compliant material, e.g., gelatin (to protect the signal generation element), is combined with carrier/active agent precursor, e.g., powder, and compressed or molded into a tablet in a manner such that the signal generation element is located at an internal position of the tablet. Instead of molding or compressing, the carrier/active agent component is, in certain embodiments, sprayed onto the signal generation element in a manner that builds up the tablet structure. In yet another embodiment, the active agent/carrier component precursor may be a liquid formulation which is combined with the signal generation element and then solidified to produce the final composition. In yet other embodiments, pre-made tablets may be fitted with the signal generation element by stably attaching the signal generation element to the tablet. Of interest are protocols that do not alter the properties of the tablet, e.g., dissolution etc. For example, a gelatin element that snap fits onto one end of a tablet and has the chip integrated with it is employed in certain embodiments. The gelatin element is colored in certain embodiments to readily identify tablets that have been fitted with the signal generation element. Where the composition has a active agent/carrier composition filled capsule configuration, e.g., such as a gelatin capsule filled configuration, the signal generation element may be integrated with a capsule component, e.g., top or bottom capsule, and the capsule filled with the active agent/carrier composition to produce the final composition. The above reviewed methods of manufacture are merely illustrative of the variety of different ways in which the compositions of the invention may be manufactured.

Systems

Also provided are systems that include the subject compositions. Systems of the subject invention include, in certain embodiments, one or more active agent containing compositions, e.g., as reviewed above, as well as a signal detection component, e.g., in the form of a receiver. The signal detection component may vary significantly depending on the nature of the signal that is generated by the signal generation element of the composition, e.g., as reviewed above.

In certain embodiments, the signal detection component is an implantable component. By implantable component is meant that the signal detection component is designed, i.e., configured, for implantation into a subject, e.g., on a semi-permanent or permanent basis. In these embodiments, the signal detection component is in vivo during use. In yet other embodiments, the signal detection component is ex vivo, by which is meant that the detection component is present outside of the body during use. In certain of these embodiments, as developed in greater detail below, either separate from or integrated with the ex vivo detection component may be a dosage dispenser element, e.g., for dispensing dosages of the compositions based on signal detected from the signal generation element of the detector. Such features may also be present in implantable detection components, e.g., to provide a closed loop administration system that administers a subsequent dosage based on input about ingestion of a previous dosage.

As reviewed above, in certain embodiments the signal generation element of the composition is activated upon contact with a target body site. In certain of these embodiments, the signal detection component is activated upon detection of a signal from the signal generation element. In certain of these embodiments, the composition generates an intermittent signal. In certain of these embodiments, the detection element is capable of simultaneously detecting multiple compositions.

The signal detection component may include a variety of different types of signal receiver elements, where the nature of the receiver element necessarily varies depending on the nature of the signal produced by the signal generation element. In certain embodiments, the signal detection component may include one or more electrodes for detecting signal emitted by the signal generation element. In certain embodiments, the receiver device will be provided with two electrodes that are dispersed at some distance. This distance allows the electrodes to detect a differential voltage. In certain embodiments, the first electrode is in contact with an electrically conductive body element, e.g., blood, and the second electrode is in contact with an electrically insulative body element relative to said conductive body element, e.g., adipose tissue (fat). In an alternative embodiment, a receiver that utilizes a single electrode is employed. In certain embodiments, the signal detection component may include one or more coils for detecting signal emitted by the signal generation element. In certain embodiments, the signal detection component includes an acoustic detection element for detecting signal emitted by the signal generation element.

For those embodiments where the signal generated by the identifier is a near-field conductive signal, e.g., as reviewed above, the receiver of the present systems may also be viewed as "data collectors." As used herein, a "data collector" is any device equipped with receiving antenna to detect the potential differences created in the body by a transmitter as described above, thus receiving the information transmitted. A data collector may handle received data in various ways. In some embodiments, the collector simply retransmits the data to an external device (e.g., using conventional RF communication). In other embodiments, the data collector processes the received data to determine whether to take some action such as operating an effector that is under its control, activating a visible or audible alarm, transmitting a control signal to an effector located elsewhere in the body, or the like. In still other embodiments, the data collector stores the received data for subsequent retransmission to an external device or for use in processing of subsequent data (e.g., detecting a change in some parameter over time). It is to be understood that data collectors may perform any combination of these and/or other operations using received data.

While the receiving antenna is advantageously inside the patient or in contact with the patient's skin, it is not required that data collector be entirely internal to the patient. For instance, a watch or belt worn externally and equipped with suitable receiving electrodes can be used as a data collector in accordance with one embodiment of the present invention. The data collector may provide a further communication path via which collected data can be extracted by a patient or health care practitioner. For instance, an implanted collector may include conventional RF circuitry (operating, e.g., in the 405-MHz medical device band) with which a practitioner can communicate, e.g., using a data retrieval device, such as a wand as is known in the art. Where the data collector includes an external component, that component may have output devices for providing, e.g., audio and/or visual feedback; examples include audible alarms, LEDs, display screens, or the like. The external component may also include an interface port via which the component can be connected to a computer for reading out data stored therein.

In some embodiments, the data collector is implanted. For instance, as noted above, pacemaker leads provide a suitably sized receiving antenna. Typical pacemakers include a control unit (referred to as a "can") that incorporates logic circuits configured to perform various data collection and processing operations. The can is also connected to RF transmitter/receiver circuitry that allows communication between the pacemaker and an external wand operated by a health care practitioner. Thus, where the patient has a pacemaker, leveraging the existing unit as a data collector may be an efficient choice.

In certain embodiments, the system further includes an element for storing data, i.e., a data storage element. Typically, the data storage element is a computer readable medium. The term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer. With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

In certain embodiments, the data that is recorded on the data storage element includes at least one of, if not all of, time, date, and an identifier of each composition administered to a patient, where the identifier may be the common name of the composition or a coded version thereof. In certain embodiments, the data of interest includes hemodynamic measurements. In certain embodiments, the data of interest includes cardiac tissue properties. In certain embodiments, the data of interest includes pressure or volume measurements.

The invention also provides computer executable instructions (i.e., programming) for performing the above methods. The computer executable instructions are present on a computer readable medium. Accordingly, the invention provides a computer readable medium containing programming for use in detecting and processing a signal generated by a composition of the invention, e.g., as reviewed above.

As such, in certain embodiments the systems include one or more of: a data storage element, a data processing element, a data display element, data transmission element, a notification mechanism, and a user interface. These additional elements may be incorporated into the receiver and/or present on an external device, e.g., a device configured for processing data and making decisions, forwarding data to a remote location which provides such activities, etc.

In certain embodiments, the signal detection component includes a cardiac monitoring element, such as shown in the system of FIG. 1. FIG. 1 shows a human 10 who has an implanted cardiovascular device "can" 8 and a lead 6, which components are employed to monitor and detect the signal emitted from pill 14. The monitoring device can be positioned in other locations as well, such as subcutaneously, in the heart, or in the waist near the stomach, for example. Positioning may be suggested by a particular application.

The inventive monitoring system can also be positioned as an external device. By example, it could be positioned by a harness that is worn outside the body and has one or more electrodes that attach to the skin at different locations. The inventive construct can be linked to a portable device, for example a watch that has one or two electrodes dispersed on the wrist. There are many places where such a receiving electrode system could be placed and created such as, hearing aids that beep, necklace, belt, shoes (PZT-powered), or earrings.

As indicated above, in certain embodiments the systems include an external device which is distinct from the receiver (which may be implanted or topically applied in certain embodiments), where this external device provides a number of functionalities. Such an apparatus can include the capacity to provide feedback and appropriate clinical regulation to the patient. Such a device can take any of a number of forms. By example, the device can be configured to sit on the bed next to the patient. The device can read out the information described in more detail in other sections of the subject patent application, both from pharmaceutical ingestion reporting and from psychological sensing devices, such as is produced internally by a pacemaker device or a dedicated implant for detection of the pill. The purpose of the external apparatus is to get the data out of the patient and into an external device. One feature of external apparatus is its ability to provide pharmacologic and physiologic information in a form that can be transmitted through a transmission medium, such as a telephone line, to a remote location such as a clinician or to a central monitoring agency.

In certain embodiments, the cardiac monitoring element includes a conduction velocity measurement element. In certain embodiments, the cardiac monitoring element includes a pressure sensor. In certain embodiments, the cardiac monitoring element includes a dimension sensor.

Additional physiological sensors with various designs have been described in additional applications by some of the present inventors. These sensors can by used jointly with the present inventive systems. In addition, other applications by some of the present inventors describe multiplexing systems with which the present invention can be very usefully employed in an interactive, synergistic manner.

This prior work by some of the present inventors describes the use of dimension sensors to determine heart parameters in order to facilitate appropriate therapy intervention, such as resynchronization therapy. Using the present invention to determining the time of blood-stream absorption of cardiac treatment pharmaceutical and correlating this with changes produced in heart function sensed by those devices provides highly valuable information for the clinician in titrating medications and providing synergy between pharmacological and electrophysiological treatment.

Embodiments of the present invention can be used in various systems. Such systems may include various types of sensors. Such sensors and systems have been described in various applications by some of the present inventors. These applications also describe multiplexing systems previously developed by some of the present inventors with which the present invention can be employed. These applications include: U.S. patent application Ser. No. 10/734,490 published as 20040193021 titled: "Method And System For Monitoring And Treating Hemodynamic Parameters"; U.S. patent application Ser. No. 11/219,305 published as 20060058588 titled: "Methods And Apparatus For Tissue Activation And Monitoring"; International Application No. PCT/US2005/046815 titled: "Implantable Addressable Segmented Electrodes"; U.S. patent application Ser. No. 11/324, 196 titled "Implantable Accelerometer-Based Cardiac Wall Position Detector; U.S. patent application Ser. No. 10/764, 429, entitled "Method and Apparatus for Enhancing Cardiac Pacing," U.S. patent application Ser. No. 10/764,127, entitled "Methods and Systems for Measuring Cardiac Parameters," U.S. patent application Ser. No. 10/764,125, entitled "Method and System for Remote Hemodynamic Monitoring"; International Application No. PCT/US2005/ 046815 titled: "Implantable Hermetically Sealed Structures"; U.S. application Ser. No. 11/368,259 titled: "Fiberoptic Tissue Motion Sensor"; International Application No. PCT/US2004/041430 titled: "Implantable Pressure Sensors"; U.S. patent application Ser. No. 11/249,152 entitled "Implantable Doppler Tomography System," and claiming priority to: U.S. Provisional Patent Application No. 60/617, 618; International Application Serial No. PCT/US05/39535 titled "Cardiac Motion Characterization by Strain Gauge". These applications are incorporated in their entirety by reference herein.

Some of the present inventors have developed a variety of display and software tools to coordinate multiple sources of sensor information. Examples of these can be seen in PCT application serial no. PCT/US2006/12246 titled: "Automated Optimization of Multi-Electrode Pacing for Cardiac Resynchronization" and filed on Mar. 31, 2006 and claiming priority to U.S. Provisional patent applications "Automated Timing Combination Selection" and "Automated Timing Combination Selection Using Electromechanical Delay", both filed Mar. 31, 2005. These applications are incorporated in their entirety by reference herein.

The above described systems are reviewed in terms of communication between an identifier on a pharmaceutical composition and a receiver. However, the systems are not so limited. In a broader sense, the systems are composed of two or more different modules that communicate with each other, e.g., using the transmitter/receiver functionalities as reviewed above, e.g., using the monopole transmitter (e.g., antenna) structures as described above. As such, the above identifier elements may be incorporated into any of a plurality of different devices, e.g., to provide a communications system between two self-powered devices in the body, where the self-powered devices may be sensors, data receivers and storage elements, effectors, etc. In an exemplary system, one of these devices may be a sensor and the other may be a communication hub for communication to the outside world. This inventive embodiment may take a number of forms. There can be many sensors, many senders and one receiver. They can be transceivers so both of these can take turns sending and receiving according to known communication protocols. In certain embodiments, the means of communication between the two or more individual devices is the mono polar system, e.g., as described above. In these embodiments, each of these senders may be configured to take turns sending a high frequency signal into the body using a monopole pulling charge into and out of the body which is a large capacitor and a conductor. The receiver, a monopole receiver is detecting at that frequency the charge going into and out of the body and decoding an encrypted signal such as an amplitude modulated signal or frequency modulated signal. This embodiment of the present invention has broad uses. For example, multiple sensors can be placed and implanted on various parts of the body that measure position or acceleration. Without having wires connecting to a central hub, they can communicate that information through a communication medium.

Methods

In the methods of the subject invention, an effective amount of a composition of the invention is administered to a subject in need of the active agent present in the composition, where "effective amount" means a dosage sufficient to produce the desired result, e.g. an improvement in a disease condition or the symptoms associated therewith, the accomplishment of a desired physiological change, etc. The amount that is administered may also be viewed as a therapeutically effective amount. A "therapeutically effective amount" means the amount that, when administered to an subject for treating a disease, is sufficient to effect treatment for that disease.

The composition may be administered to the subject using any convenient means capable of producing the desired result, where the administration route depends, at least in part, on the particular format of the composition, e.g., as reviewed above. As reviewed above, the compositions can be formatted into a variety of formulations for therapeutic administration, including but not limited to solid, semi solid or liquid, such as tablets, capsules, powders, granules, ointments, solutions, suppositories and injections. As such, administration of the compositions can be achieved in various ways, including, but not limited to: oral, buccal, rectal, parenteral, intraperitoneal, intradermal, transdermal, intracheal, etc., administration. In pharmaceutical dosage forms, a given composition may be administered alone or in combination with other pharmaceutically active compounds, e.g., which may also be compositions having signal generation elements stably associated therewith.

The subject methods find use in the treatment of a variety of different conditions, including disease conditions. The specific disease conditions treatable by with the subject compositions are as varied as the types of active agents that can be present in the subject compositions. Thus, disease conditions include, but are not limited to: cardiovascular diseases, cellular proliferative diseases, such as neoplastic diseases, autoimmune diseases, hormonal abnormality diseases, infectious diseases, pain management, and the like.

By treatment is meant at least an amelioration of the symptoms associated with the disease condition afflicting the subject, where amelioration is used in a broad sense to refer to at least a reduction in the magnitude of a parameter, e.g. symptom, associated with the pathological condition being treated. As such, treatment also includes situations where the pathological condition, or at least symptoms associated therewith, are completely inhibited, e.g. prevented from happening, or stopped, e.g. terminated, such that the subject no longer suffers from the pathological condition, or at least the symptoms that characterize the pathological condition. Accordingly, "treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). For the purposes of this invention, a "disease" includes pain.

A variety of subjects are treatable according to the present methods. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In representative embodiments, the subjects will be humans.

In certain embodiments, the subject methods, as described above, are methods of managing a disease condition, e.g., over an extended period of time, such as 1 week or longer, 1 month or longer, 6 months or longer, 1 year or longer, 2 years or longer, 5 years or longer, etc. The subject methods may be employed in conjunction with one or more additional disease management protocols, e.g., electrostimulation based protocols in cardiovascular disease management, such as pacing protocols, cardiac resynchronization protocols, etc.; lifestyle, such a diet and/or exercise regimens for a variety of different disease conditions; etc.

In certain embodiments, the methods include modulating a therapeutic regimen based data obtained from the compositions. For example, data may be obtained which includes information about patient compliance with a prescribed therapeutic regimen. This data, with or without additional physiological data, e.g., obtained using one or more sensors, such as the sensor devices described above, may be employed, e.g., with appropriate decision tools as desired, to make determinations of whether a given treatment regimen should be maintained or modified in some way, e.g., by modification of a medication regimen and/or implant activity regimen. As such, methods of invention include methods in which a therapeutic regimen is modified based on signals obtained from the composition(s).

In certain embodiments, also provided are methods of determining the history of a composition of the invention, where the composition includes an active agent, an identifier element and a pharmaceutically acceptable carrier. In certain embodiments where the identifier emits a signal in response to an interrogation, the identifier is interrogate, e.g., by a wand or other suitable interrogation device, to obtain a signal. The obtained signal is then employed to determine historical information about the composition, e.g., source, chain of custody, etc.

In yet other embodiments where the identifier is one that survives digestion, the methods generally include obtaining the signal generation element of the composition, e.g., by retrieving it from a subject that has ingested the composition, and then determining the history of the composition from obtained signal generation element. For example, where the signal generation element includes an engraved identifier, e.g., barcode or other type of identifier, the engraved identifier may be retrieved from a subject that has ingested the composition and then read to identify at least some aspect of the history of the composition, such as last known purchaser, additional purchasers in the chain of custody of the composition, manufacturer, handling history, etc. In certain embodiments, this determining step may include accessing a database or analogous compilation of stored history for the composition.

Utility

The present invention provides the clinician an important new tool in their therapeutic armamentarium: automatic detection and identification of pharmaceutical agents actually delivered into the body. The applications of this new information device and system are multi-fold. Applications include, but are not limited to: (1) monitoring patient compliance with prescribed therapeutic regimens; (2) tailoring therapeutic regimens based on patient compliance; (3) monitoring patient compliance in clinical trials; (4) monitoring usage of controlled substances; and the like. Each of these different illustrative applications is now reviewed in greater detail below.

Monitoring Patient Compliance with Prescribed Therapeutic Regimens

As summarized above, one type of application in which the subject compositions and systems find use is in monitoring patient compliance with prescribed therapeutic regimens. By monitoring patient compliance is meant tracking whether a patient is actually taking medication in the manner prescribed to the patient. As such, the present invention provides accurate data of when a pill has been taken and which pill has been taken. This allows the precise determination of which pill was taken at a specific point in time. Such monitoring capability assures patients are taking the prescribed medication correctly. This information avoids the potential for over prescription of medications that are not actually being taken. By example, if pain killers are intended to be administered to a patient, it is possible to verify with the present invention that the patient did in fact take those pain killers in a certain period of time. This knowledge is an important tool in limiting the illicit sale of unconsumed drugs to an unintended party. In the case of cardio vascular pills, the clinician or care giver is able to verify that the amount of the drug was taken has been taken at approximately the right point and time. Thus, the true efficacy of the drug can be accurately evaluated. Proper administration and patient compliance is especially critical in Alzheimer's, psychiatric, and alcohol aversion drugs, and in the treatment of rest home residents. In the case of accidental and other overdoses situations, the intervening clinician will be able to discern how far the ingestion has proceeded, and how many pills are involved.

In more complex embodiments of the present invention, correct, timely ingestion of the drugs will automatically trigger a prescription refill signal which is forwarded to a pharmacy data system, and in some cases the refill will be automatically delivered directly to the patient's home, or released by a device in the patient's home some period of time later. This feature is particularly valuable in patients with compromised mental capacity and/or limited physical mobility.

The invention is particularly useful in complex administration regimens, such as when multiple pharmaceuticals are being taken, and confusion is more likely to occur. The inventive pills can have multiple external layers, with only correct dosage allowing dissolution and absorption of the pharmaceutical component. Specific indicators, such as electrical conduction velocity in the heart or electrolytic levels in the blood in response to pharmaceutical can also be titrated.

In certain embodiments, a patient can be alerted when the patient is in some way non-compliant with a given treatment regimen. For example, by a sound, visual, or computer reminder, if the pharmacological regimen is not being accurately adhered to, a reminder is provided. If that reminder is not accurately responded to, the system can provide an alert to family members, caregivers, or clinicians in order to remedy the gap in treatment or overdose. The device may also automatically modify the dosage and timing of the regimen to compensate for prior non-standard dosing.

Tailoring Therapeutic Regimens Based on Patient Compliance

As summarized above, one type of application in which the subject compositions and systems find use is in tailoring therapeutic regimens based on patient compliance. In such applications, data obtained about whether a patient has or has not taken a particular dosage is employed to determine future dosages and/or timing of such dosages. In certain embodiments, data concerning patient compliance is combined with additional data, e.g., sensed physiological data, to make customized changes or modifications to a given therapeutic regimen. By example, when data about dosage compliance obtained according to the invention is used in concert with other medical sensing devices, correlation between drug delivery, batch and dosage can be correlated to a physiological response. In this manner, optimal pharmatherapeutic regimens may be formulated by the clinician. By example, cardiac stimulating drugs can be titrated to the most appropriate dosages, minimizing side effects such as cardiac muscle exhaustion and rebound effects among others, and optimizing both dosage and timing for each individual patient.

Assessment of a range of alternate medications is made possible by the present invention without resort to awaiting overt clinical sequel of treatment, many of which can be seriously adverse. By example, positive effects would be quickly ascertainable without being obscured by more random factors. Negative responses, such as changes in blood pressure, would become clearly evident as drug related or independent above background physiologic variation.

In one clinical arena, the present invention allows, in concert with other sensing devices developed by some of the present inventors, the measurement and assessment of the cardiac response to those medications. These co-employed sensing devices can be those enumerated below, among others. Other sensing technology, e.g., as mentioned above, developed by some of the present inventors allows measurement of heart health and cardiac efficiency. Using these tools in concert with the present inventive device, the clinician will be able to compare the response of the heart and body to the administered pharmaceutical. The data provided by the present invention can optionally be recorded over time. The recording system records synchrony or conduction velocity of a signal going through cardiac tissue and how that is mediated by the presence of a certain medication. This unique data is made possible by the present invention since it can determine electronically exactly when the pill or other medication was being absorbed into the body.

In more standard clinical environments, this unique data allows careful selection and titration of drug administration without resort to more overt physical symptoms to ascertain contraindications, efficacy, and optimal dosage levels The present invention provides a record for emergency room technicians or doctors when a patient is admitted to a hospital so that the patient's status can be accurately ascertained. Dosage events within the last hour or day prior to admission, and the identity of the last medication, will be immediately available. As such, future therapeutic regimens can be made based on accurate records of patient drug medication history.

In certain embodiments, the clinician obtains this information through simple interrogation of the implanted or portable device. This device would tell them without any uncertainty what pills have been taken. As the inventive technology becomes more wide spread, this data will become more regularly available. The present inventive microchips are sufficiently inexpensive such that when they are put into standard production, most or all pharmaceuticals will be fitted with them as a matter of course.

The patient monitoring capacity of the external reporting apparatus is an importation function which the inventive device can provide. When coordinated with internal or external physiologic sensing data, the device can read out the physiological response of the patient to the ingestion of medication, and then transmit this information back to the clinician. The clinician can then modify therapy to optimal effectiveness, as indicated by the new data in response to the modified therapy, and so forth.

In more sophisticated embodiments of the present invention, the dosage adjustment function, within certain parameters, can be performed by an intelligence circuit in the apparatus. By example, for a blood pressure medication, the patient takes their blood pressure pill. 20 minutes later, the internal monitoring circuitry in the implantable device registers a drop in blood pressure. The circuitry quantifies this drop, and transmits it to this bedside apparatus. The apparatus then can adjust the dosage of the pill to optimally treat the patient. Similarly, when the patient is connected to an IV, the dosage can be dispensed directly into the IV fluid. In certain embodiments, the closed-loop system is provided as a fully implantable device.

Current clinical practice for drug treatment optimization is considerably more limited than that which is available by use of the present inventive device. Currently, blood pressure medication treatment is set at so many pills per day. Such a blunt dosage regime takes a long time to optimize appropriately because the feedback loop is very slow. By contrast, with the present invention, the feedback loop of physiologic response to pharmaceutical dosage is very rapid and very efficient. Ultimately, the present invention allows tailoring the drug dosages day to day, or even more finely, to account for change in activity, change in physiological conditions in the patient, and other dosage parameter.

In more sophisticated embodiments of the present invention, physiological reactions to specific dosages and time intervals would also be continually monitored. In some embodiments, the level of drug in the blood stream is monitored, allowing for individual and time of day variations in drug metabolism.

This aspect of the present invention effectively minimizes underdosing or overdosing the controlled substances, in some cases addressing these changes before they produce external symptoms apparent to the patient or clinician. The drug dosage can be automatically titrated so that, by example, the smallest appropriate level to quell anxiety due to pain, other physiologic reactions to pain, or provide steady or gradually diminishing blood levels of the drug would be dispensed. This feature of the present invention provides an automatic, appropriately gradual, weaning off of the drug, lessening the chance of serious addiction or severe, adverse withdrawal reactions.

Clinical Trial Applications

An important application of the invention is to provide immediate feedback of physiological data response to administration of a pharmaceutical agent in clinical drug trails. A current challenge is that the experimental drug is administered broadly to a population without a comprehensive foreknowledge of which sub-groups within this population are most likely to benefit from the treatment. Another challenge is monitoring patient compliance with the treatment regimen, by determining if the tests subjects are taking the medicine as indicated. The later challenge is addressed in the sections above. Both patient non-compliance levels and actual response to drug ingestion can thus be determined. As such, compliance intervention can then be addressed early in the study.

In certain embodiments of the present invention, clinical researchers are provided with immediate access to physiological data. The clinical researchers are able to identify the subset for which the drug is most likely effective from within the original test population of possible participants in the trial. The example above of a patient receiving blood pressure medication and getting feedback immediately demonstrates how effectiveness of a novel medicine can be quickly determined.

Upon administration of the first doses of medication to initial test subjects, the clinical researchers are likely to find that some subjects in the population respond to the medication and others do not. This immediate feedback allows the administrator of the trail to exclude those patients who do not respond to the medication and target only that subgroup for which there is clear efficacy. This culling process allows the overall results of the trail to get a much higher effective percentage, because one is able to target the drug to the group for whom it is effective. It also avoids side effect challenges for subjects who would not have a benefit balance to such risks.

As such, from this innovative data, the present invention provides the clinician an accurate dose response curve showing the response to that medication and the timing of the digestion of the pill. Such innovative data has many applications. For instance, the clinician now has the ability to determine which patients have no response to the medicine in the pill. In a study situation, such patients can be removed from a study or a test of the clinical utility of a certain medication. This ability provides that only people who have a beneficial response to a certain medication are retained in the trail. This feature will improve the efficacy of medications and to reduce the amount of medications that people take that are not being useful. It may also be used in trials to determine which patients actually consumed the medicine, and which did not.

The present invention allows identification of physiological proxies for the efficacy of a drug. By example, for a drug which has a long term administration prior to the development of overt clinical changes, there are typically certain short term physiological factors which appear immediately after ingestion of the drug. By example, cancer medication which requires many months to show an effect, can have shorter term indicia of its efficacy in one or a constellation of physiologic factors. Changes, both local or throughout the whole body, in blood pressure, body temperature, internal chemical enzymes or other factors will serve as proxies for the longer term desired effects. A precise correlation of these factors with the time of the pills ingestion enhances the ability to find meaningful indicia.

With the very closely timed correlated response to the ingestion of the pill provided for the first time by the present innovation, demonstrating that a physiologic response is a result of the drug ingestion rather than any of the other possibility confounding factors, is much more likely. This capacity of the present invention can serve as a partial or complete proxy for clinical trials.

The invention provides a way to determine very quickly whether a patient should be taking the medication or not, whether it will be effective or not, and allow its appropriate titration. Synergies between medications, both helpful and adverse, will also become more readily apparent.

Monitoring Usage of Controlled Substances

As reviewed above, in other embodiments of the inventive microchips, the identifiers can be fitted with coils, susceptible of interrogation without being dissolved in the body. This is accomplished by transmitting RF energy into the coil in such a way that the inquirer will be apprised of the presence and identity of a pill before it is ingested.

In an additional embodiment of the present invention, a "smart box" is provided that can interrogate each pill and ascertain its address. The box can write a distinctive product number or product code so that every single pill ever made is provided with a unique identifier. Fuses, for example, may be selectively destroyed so the addresses may be detected electrically or optically. Particularly in the case of controlled substances, such as a narcotic, this will be important in limiting the illegal used of previously legitimate medicines. The present invention makes it possible to identify precisely who bought such a pill from the authorized pharmacist. This use of the present invention will rein in the number of illicit uses of controlled substances on the market place.

An important application for the external apparatus aspect of the present invention is in monitoring and regulating the use of controlled pharmaceutical substances. A serious risk when patients are prescribed heavy narcotics for pain control is the possibility of addiction. In its simplest analysis, addiction occurs from the ingestion of too much of the controlled medication by inadvertent overdosing, purposeful misuse, or through inexact dosage prescription. Additionally, as described above, individual serial number are provided on such pharmaceuticals to track the legitimate distribution of the drug before the illicit distribution of such drugs.

In one application of the present invention, a means for locking and regulating the dosage of a potential addictive drug is provided. An example of this capacity of the present invention is when a patient takes their narcotic pill, in which the ingestion of the medication is registered by the internal device. This information is then automatically transmitted to the external apparatus.

The inventive apparatus is so configured that only after the patient has taken the pill and at the appropriate time has elapsed does this accessory apparatus dispense a further pill. In this manner, the addiction rate for the drug is dramatically lowered by limiting legal drug availability by dispensing exactly the prescribed dosage at precisely the appropriate time interval.

The external apparatus can also be effectively employed in mandatory medication forensic applications. For example, in the case of a convicted criminal, the criminal can be required to take court ordered medication as a condition of release from jail. Using the present invention, the court or probation officer has access to a real-time record of the administration of this drug as this information is fed back through the accessory apparatus to the appropriate official. There is a current trend towards court mandated psychotropic or chemical sterilization drug maintenance for sex offenders which would be addressed by this aspect of the present invention. This use of the present invention is analogous to house arrests where physical position monitoring bands are worn on the ankle of the offender.

Kits

Also provided are kits for practicing the subject methods. Kits may include one or more compositions of the invention, as described above. The dosage amount of the one or more pharmacological agents provided in a kit may be sufficient for a single application or for multiple applications. Accordingly, in certain embodiments of the subject kits a single dosage amount of a pharmacological agent is present and in certain other embodiments multiple dosage amounts of a pharmacological agent may be present in a kit. In those embodiments having multiple dosage amounts of pharmacological agent, such may be packaged in a single container, e.g., a single tube, bottle, vial, and the like, or one or more dosage amounts may be individually packaged such that certain kits may have more than one container of a pharmacological agent.

Suitable means for delivering one or more pharmacological agents to a subject may also be provided in a subject kit. The particular delivery means provided in a kit is dictated by the particular pharmacological agent employed, as described above, e.g., the particular form of the agent such as whether the pharmacological agent is formulated into preparations in solid, semi solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intraperitoneal, intradermal, transdermal, intracheal, etc. Accordingly, certain systems may include a suppository applicator, syringe, I.V. bag and tubing, electrode, etc.

In certain embodiments the kits may also include a signal receiving element, as reviewed above. In certain embodiments, the kits may also include an external monitor device, e.g., as described above, which may provide for communication with a remote location, e.g., a doctor's office, a central facility etc., which obtains and processes data obtained about the usage of the composition.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

The following example is offered by way of illustration and not by way of limitation.

EXPERIMENTAL

Example 1

In the following experiment, a transmitter (Tx) and receiver (Rx), each powered by batteries and encased in a water-tight Rubbermaid™ container, are employed. The Tx and Rx float in a bath of saline, and an LED glows on the Rx when the Tx is placed in the bath. Both Tx and Rx are completely isolated from the outside world.

The Tx, representing the compositions of the present application, e.g., a pill composition having an active agent and signal generation element, is an oscillator circuit based on a CMOS timer chip. It produces a square wave at about 80 kHz of 3V amplitude from a Lithium battery. A tightly twisted pair of wires extends from the circuit, out of the container, and into the bath. At the end of the twisted pair, the wires are striped of insulation by about 1 mm and separated to form a dipole antenna. The signal amplitude was found to scale linearly with the separation distance characterizing this dipole. The signal was easily detectable with this setup when the dipole was 5 mm in extent.

The Rx is a filtered amplifier circuit with outputs to detect the transmitted signal. A square of copper, 10 cm on a side, was attached to the bottom of the outside of the container and attached to the negative differential input of the circuit; this represents the pacing can. A bipolar pacing lead, about 40 cm long, was attached to the positive differential input of the circuit; the ring electrode was selected for the input. The differential signal was coupled into the inputs of a gain 100 instrumentation amplifier through 0.1 uF series capacitors. The output of the instrumentation amplifier was fed into a 4-pole high-pass filter, with gain of 100 and cutoff frequency 5 kHz. This output was fed into a 2-pole low-pass filter with gain 20 and cutoff frequency 100 kHz. Thus, the overall gain of the circuit is 200,000. This output signal is applied across an LED and resistor in series, which glows when the output signal exceeds a few volts.

When not in the bath, the Rx LED was on all the time as it picked up interference and power line noise from the environment. When the pacing lead was shorted to the mock can the LED turned off.

When placed in solution, the LED turned off. When the Tx was also placed in solution, the Rx LED turned on and the dependence on position and orientation was investigated. The intensity of the LED was found to depend on the cosine of the angle between the Rx and Tx dipole, with a null for perpendicular orientation and sign inversion as the sense of the dipole was reversed, as observed with an external oscilloscope. The intensity of the LED was found to vary directly with position, with a bright, saturated glow observed for spacing less than 5 cm and a dim, diffuse glow observed for the maximum spacing allowed by the bath, about 50 cm.

The key to making the detection robust is differentiating the desired signal from spurious interference. Such was accomplished in this experiment by restricting the frequency band of sensitivity to between 5 and 100 kHz. To the extent this band can be narrowed, the more robust the system will be. The challenge here is to match the frequency of the Tx and Rx circuits, in light of the fact that the Tx frequency may vary by 30% due to manufacturing variation. The Rx circuit can be very narrow through the use of a narrow bandpass or by using demodulation techniques from the radio. The Rx circuit can be swept across a tuning frequency range to detect the presence of the pill. The presence of the pill can be confirmed by encoding an unlikely bit sequence in the digital information transmitted by the pill.

Two problems with this approach are that it consumes power from the Rx circuit while it scans frequencies, and that synchronization with multiple pills, which may burst the transmission of their codes, is difficult. If the frequency of the Tx is known ab initio, as is possible with circuit trimming or advanced manufacturing processes, an elegant solution to both these problems is presented. At the input to the Rx circuit, a tuned LC oscillator matched to the Tx frequency will "ring up" when the desired signal is present. This power can be detected by a simple diode circuit, which serves as a trigger to turn the detection circuit on, greatly reducing the time it must draw current. This tuned input also serves to narrow the bandwidth and reject spurious signals.

This above experiment demonstrates the ability to transmit and detect signals through a synthetic biological medium. The Tx may be readily powered off a chemical battery, such as a Pt/Mg system. Furthermore, digital information is readily encoded in the signal using a variety of encoding techniques to eliminate errors and improve the overall reliability of the system.

Example 2

A transmitter according to the subject invention was set up as follows. The circuit was powered off a 9V battery and floated on a bath of saline. The circuit was an oscillator based on the TLC551 chip, a CMOS version of the popular 555 timer. The oscillator was run at ~7 kHz, with a duty cycle of perhaps 15%. The outputs of the oscillator were each capacitively coupled through 7 uF to a twisted pair, which was terminated in a small "Y" shaped dipole, with the arms separated by ~1 mm, and ~2 mm of bare wire exposed to the saline bath.

The signal was received through two Cu electrodes, each with ~1 $cm^2$ exposed to the bath. This was routed to the input of a Stanford pre-amp operated off batteries, set to a gain of 1000 with a pass band between 3 kHz and 30 kHz. The output of the pre-amp was observed on a battery powered oscilloscope.

A maximum signal of ~200 μV referenced to the amplifier input was observed for an Rx electrode separation of ~20 cm. A dipolar coupling strength was observed, displaying a sinusoidal angular dependence, with a null in received signal for perpendicular orientation; phase inversion was seen between parallel and anti-parallel orientations. The received signal strength was seen to scale linearly with separation of the Rx electrodes.

The above demonstrates that the signal is clearly detectable with proper amplification and filtering. Furthermore, a capacitor on the input of the Rx amplifier is not necessary; as the same results were obtained using DC coupling on the input with a high-pass filter later in the signal chain.

The above results also verified that the Tx can run off an Mg/Pt potato battery.

Example 3

A prototype smart pill microchip, which broadcasts a fixed code using frequency shift keying, was first powered by a 1.5V AA battery. The conductive signal was applied to a physiological saline bath with a twisted pair T-shaped dipole, approximately 1 cm across with 1 mm of conductor exposed on each arm of the T. The signal was detected by two copper electrodes, spaced approximately 10 cm apart, which feed into a battery powered, isolated differential pre-amp. The signal was observed on an oscilloscope. An oscillatory signal, clearly representative of the transmitted data, was observed with a frequency of about 300 kHz and an input-referenced amplitude of about 10 mV.

Furthermore, a dependence of the received signal strength on the cosine of the angle between the transmit and receive conductors, as is characteristic of a dipolar interaction, was observed.

A Mg—CuI water-activated battery, with each electrode having an exposed surface area of ~1 mm$^2$ was constructed. The Mg electrode was formed by simply potting commercial grade Mg ribbon in epoxy and polishing the end flat with sandpaper. The CuI electrode was produced by first polishing the end of Cu wire potted in epoxy.

Approximately 100 µm of Cu was then electroplated on the end of the Cu wire using standard techniques, with the parameters chosen to give a large roughness coefficient, increasing the effective area of the electrode. The surface of this plated Cu was then transformed electrochemically to CuI by applying a potential corresponding to the potential of the Cu+ ion in a solution of I− ions. In approximately 15 min 40 mC of CuI was produced. The battery was demonstrated to have an open cell voltage of ~1.05V in a pH 2 solution, corresponding to the acidity of a typical stomach.

The CuI—Mg battery was connected to the power terminals of the chip, and the output terminals were connected to the dipole conductor described above in a physiological saline bath. The battery was activated by dropping the electrodes in the bath, and a signal of amplitude ~2 mV at a frequency of 20 kHz was observed for at least a minute.

Finally, the output terminals of the chip were shorted together, effectively configuring the chip for the 2-terminal operation described above. An output signal was observed, but its amplitude was much weaker, probably because of the decreased effective transmitter dipole length in this configuration. That is, in the 4-terminal configuration, the effective transmit conductor size is determined by the spacing between the battery and dipolar T, which was several centimeters; in the 2-terminal mode, the effective dipole length is reduced to the separation between the Mg and CuI electrodes, which was less than 1 cm. The observed signal was perhaps a few hundred µV, and could be quantified using averaging to overcome an interfering signal amplified by the broadband receiver. More sophisticated detection schemes will have little problem detecting such a signal reliably.

Example 4

A pill composition as described above prior to ingestion may be composed of two main components, an address generating logic circuit and a signal transmission circuit. The address generation circuit is powered with low current adequate to the required tasks. However, if the voltage supplied to the address generation circuit changes, the frequency of the oscillator therein will also change. This may produce changes in signal transmission, introduce noise into the transmission, and cause other undesired effects.

For design purposes, it is simpler to power the address generation circuit with a constant voltage. However, in certain embodiments a more complex configuration may be desired. By example, when the transmission starts, the transmitter consumes considerable energy. As a result, the voltage will drop because as more energy is consumed, the voltage of the power source drops. The change in voltage will result in a change of frequency in the oscillator within the address generation circuit.

An example of this challenge in a different area of engineering is when a remote control device is made from a receiver and servos. By contrast, the receiver works permanently, and consumes low current in proportion to the servo which consumes a very large current. The servos work only when a signal is transmitted to the remote site. In that case, the whole system consumes a relatively large amount of power when the servos start to work. When the servo starts to work, the voltage drops, and produces some noise. As a result, the stability of signal transmission is compromised.

In order to avoid this problem, embodiments of the system are powered with two voltage sources. The receivers are powered with one battery, and the servos are powered with another battery. With this configuration, whatever occurs in the servo does not affect the receiver. As such, a more stable remote control results, thereby improving the performance of the complete system.

In one embodiment, a common cathode is provided. There are also two positive electrodes, A1 and A2. In this case, with the battery divided into two parts, one part of the battery will power the address generation circuit, and the other will power the transmission circuit. This configuration provides a stable voltage to the address generation circuit. When the transmitter section of the device is turned on, only the voltage on the transmitter will change, but no change of voltage will occur in the address generation section of the device. Hence, the changes will typically cause a change in signal amplitude, but not in the frequency. As a result, the transition will be more stable, and the frequency of RF transmission will be unaffected, or minimally effected.

The above phenomena are not of concern if there is a big area of battery electrode, because the voltage of the system as a whole will not change. However, in the case of a small battery electrode, the transmitter can potentially lower the voltage of the battery, and there will be a change in voltage over the entire circuitry. If the battery is divided into two parts, the voltage of one battery can be changed while the other will continue to power the address generation circuit with a constant voltage.

Figure 23:
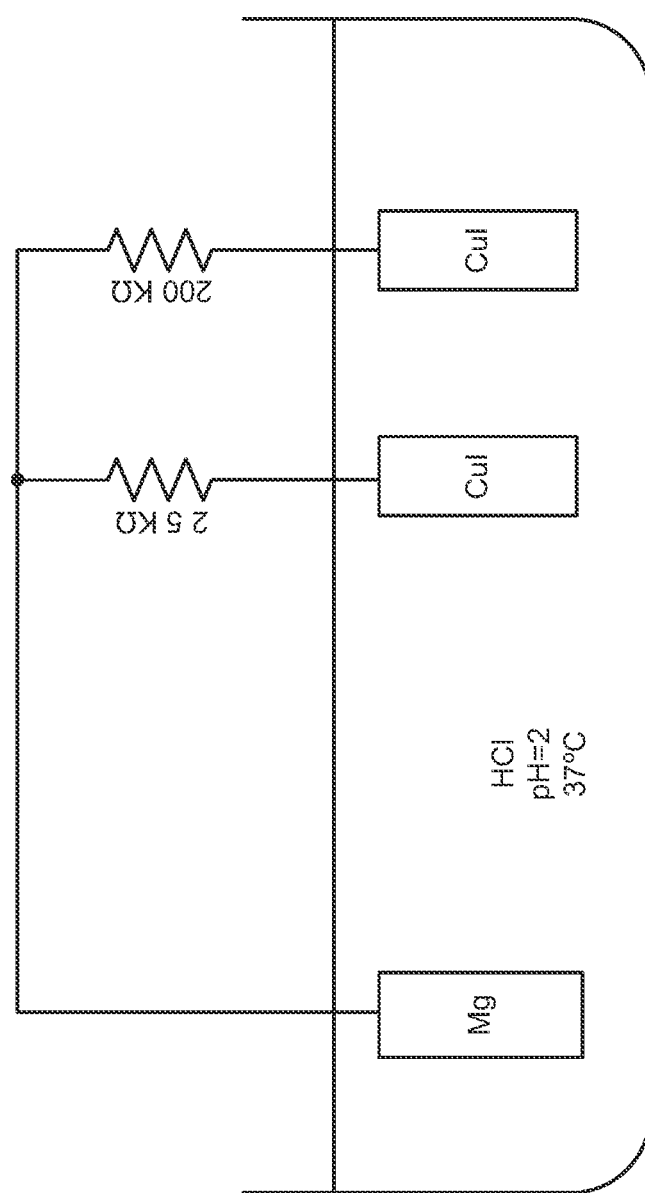
FIG. 23 shows the principle of an experiment with a split battery configuration.
Figure 24:
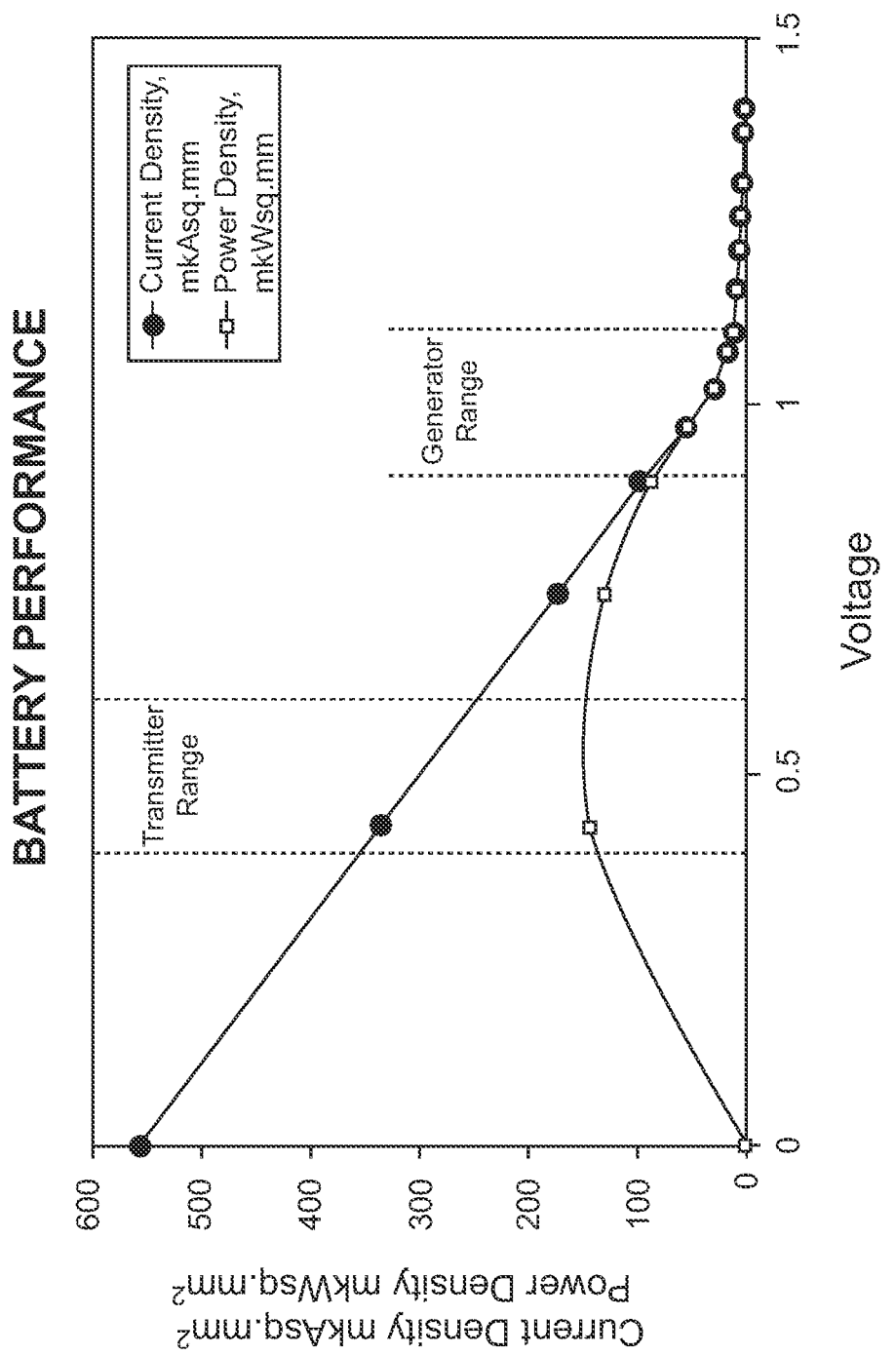
FIG. 24 shows the performance of a pair of split batteries.

A consideration in the design development is how one battery will affect the other. Experiments conducted by some of the present inventors show that a change of load on one battery does not affect the other; i.e., they worked independently. In this experiment, as is shown in FIG. 23, two copper iodine anode electrodes were provided with a magnesium electrode as a common cathode. These were connected to a zero-resistance ammeter, and performance was measured. One copper iodine electrode was connected through a 2.5 KΩ resistor, and the other through a 200 KΩ resistor. All the electrodes are submerged in a pH 2 HCl solution at about 37° C. The data derived from this experiment is shown in FIG. 24. The two copper iodine electrodes work independently of each other.

An ordinary skilled artesian will easily identify different materials and configurations for the above device. The chemistry of this copper iodine and various manners of preparation will be understood or quickly developed.

The surface preparation before the copper iodine is forming is of interest. One approach is to use copper wire embedded in epoxy. This can be plated with electrolytic copper. After the copper is polarized in solution of potassium iodide, copper iodine is formed on the tip of the electrode. Copper iodine can also be formed by chemically deposition. Other means are also available.

10 μm is a typical range for thickness of copper iodide to produce an adequate amount of electricity to accomplish the activity of the device for a 15 minute period. If less thickness is employed, the transmission will last a shorter time. Thus, the thickness of copper iodide is determined by the time required to produce electricity to provide the results needed for a particular application. For several seconds of transmission, less than 1 μm of copper iodide would be adequate. For one microsecond of transmission, a few nanometers of copper iodine thickness, such as in the range of about 10-100 nanometers, more specifically, about 20-50 nanometers is sufficient.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A system for communicating information within a body of a patient, the system comprising:
    a first device comprising:
        a support;
        circuitry associated with the support;
        an electric dipole antenna comprising:
            a first electrode comprising a first material electrically coupled to the circuitry and associated with the support;
            a second electrode comprising a second material electrically coupled to the circuitry and associated with the support, wherein the first electrode is electrically isolated from the second electrode when not in contact with an electrically conductive fluid, wherein the first and second materials are selected to provide a voltage potential difference when in contact with the electrically conductive fluid;
        the circuitry configured to:
            modulate current flow through the electrically conductive fluid and between the first and second electrodes to generate a quasi-electrostatic signal; and encode information in the quasi-electrostatic signal;
the electric dipole antenna configured to transmit the quasi-electrostatic signal using electrically conductive fluid in the body of the patient as a conducting medium; and a second device comprising a receiver configured to:
receive the transmitted quasi-electrostatic signal; and
decode the encoded information from the quasi-electrostatic signal, wherein the receiver is configured to couple to the body of the patient.

2. The system of claim 1, further comprising at least one third device, wherein the at least one third device is configured to receive the transmitted quasi-electrostatic signal via a quasi-electrostatic coupling to the body of the patient, wherein the quasi-electrostatic signal is received by the at least one third device within the body of the patient.

3. The system of claim 1, wherein the quasi-electrostatic signal comprises an identifier of the first device.

4. The system of claim 1, wherein the first device comprises a signal generating circuit coupled to a power supply, and wherein the signal generating circuit is configured to generate the quasi-electrostatic signal.

5. The system of claim 1, wherein the electric dipole antenna is configured to oscillate at a frequency such that a radiation field generated by the antenna has a wavelength more than 10 times longer than a largest dimension of the body.

6. The system of claim 5, wherein the electric dipole antenna is configured to oscillate at a frequency of about 10 MHz or less.

7. The system of claim 1, wherein the first device is an ingestible medical device.

8. The system of claim 1, wherein the first device is a pharmaceutical delivery device.

9. The system of claim 1, wherein the first device comprises a power source.

10. The system of claim 1, wherein the second device is configured to transmit a control signal to an effector located in the body.

11. A communications device comprising:
a support;
a power supply;
a signal generating circuit coupled to the power supply and configured to generate a signal; and
an electric dipole antenna coupled to the signal generating circuit and comprising:
a first electrode comprising a first material electrically coupled to the circuitry and associated with the support;
a second electrode comprising a second material electrically coupled to the circuitry and associated with the support, wherein the first electrode is electrically isolated from the second electrode when not in contact with an electrically conductive fluid, wherein the first and second materials are selected to provide a voltage potential difference when in contact with the electrically conductive fluid; and
circuitry coupled to the support and configured to:
modulate current flow through the electrically conductive fluid and between the first and second electrodes to generate a quasi-electrostatic signal; and
encode information in the quasi-electrostatic signal;
wherein the electric dipole antenna is configured to transmit the signal via the quasi-electrostatic coupling to a patient's body.

12. The communications device of claim 11, wherein the power supply comprises a battery.

13. The communications device of claim 11, wherein the power supply comprises: the electric dipole antenna further configured to receive energy from the first and second electrodes via a quasi-electrostatic coupling to the body; and
a converter circuit configured to convert the received energy to electrical power.

14. The communications device of claim 11, wherein the electric dipole antenna is configured to oscillate at a frequency of about 10 MHz or less.

* * * * *